(12) United States Patent
Kordasiewicz et al.

(10) Patent No.: US 11,492,615 B2
(45) Date of Patent: Nov. 8, 2022

(54) ANTISENSE COMPOUNDS AND USES THEREOF

(71) Applicant: Ionis Pharmaceuticals, Inc., Carlsbad, CA (US)

(72) Inventors: Holly Kordasiewicz, San Diego, CA (US); Curt Mazur, San Diego, CA (US); Punit P. Seth, Carlsbad, CA (US); Eric E. Swayze, Encinitas, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 274 days.

(21) Appl. No.: 16/167,299

(22) Filed: Oct. 22, 2018

(65) Prior Publication Data

US 2019/0270990 A1   Sep. 5, 2019

Related U.S. Application Data

(63) Continuation of application No. 14/435,069, filed as application No. PCT/US2013/064643 on Oct. 11, 2013, now abandoned.

(60) Provisional application No. 61/760,593, filed on Feb. 4, 2013, provisional application No. 61/713,466, filed on Oct. 12, 2012.

(51) Int. Cl.
| | | |
|---|---|---|
| *C12N 15/11* | (2006.01) | |
| *C12N 15/113* | (2010.01) | |
| *C07H 21/00* | (2006.01) | |

(52) U.S. Cl.
CPC .......... *C12N 15/113* (2013.01); *C07H 21/00* (2013.01); *C12N 2310/11* (2013.01); *C12N 2310/315* (2013.01); *C12N 2310/321* (2013.01); *C12N 2310/322* (2013.01); *C12N 2310/323* (2013.01); *C12N 2310/341* (2013.01); *C12N 2310/346* (2013.01)

(58) Field of Classification Search
CPC ............ C12N 15/113; C12N 2310/321; C12N 2310/11; C12N 2310/315; C12N 2310/341
See application file for complete search history.

(56) References Cited

FOREIGN PATENT DOCUMENTS

| WO | WO-9950409 A1 | * | 10/1999 | .......... C12N 15/113 |
| WO | WO-2011097644 A2 | * | 8/2011 | .............. A61P 25/28 |
| WO | WO-2013022990 A1 | * | 2/2013 | .......... C12N 15/113 |

* cited by examiner

*Primary Examiner* — Ekaterina Poliakova-Georgantas
(74) *Attorney, Agent, or Firm* — McNeill Baur PLLC

(57) ABSTRACT

The present disclosure provides oligomeric compounds. Certain such oligomeric compounds are useful for hybridizing to a complementary nucleic acid, including but not limited, to nucleic acids in a cell. In certain embodiments, hybridization results in modulation of the amount activity or expression of the target nucleic acid in a cell.

15 Claims, No Drawings
Specification includes a Sequence Listing.

SEQUENCE LISTING

<160> NUMBER OF SEQ ID NOS: 11

<210> SEQ ID NO 1
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: 1, 2, 3, 4, 5, 13, 14, 15
<223> OTHER INFORMATION: Bases at these positions are RNA
<220> FEATURE:
<221> NAME/KEY: misc_feature
<222> LOCATION: (1)..(15)
<223> OTHER INFORMATION: n is a, c, g, t or u

<400> SEQUENCE: 1
nnnnnnnnnn nnnnn                                                    15

<210> SEQ ID NO 2
<211> LENGTH: 17
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: 1, 2, 3, 4, 5, 6, 14, 15, 16, 17
<223> OTHER INFORMATION: Bases at these positions are RNA
<220> FEATURE:
<221> NAME/KEY: misc_feature
<222> LOCATION: (1)..(17)
<223> OTHER INFORMATION: n is a, c, g, t or u

```
<400> SEQUENCE: 2
nnnnnnnnnn nnnnnn                                                   17

<210> SEQ ID NO 3
<211> LENGTH: 17
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: 1, 2, 3, 4, 5, 13, 14, 15, 16, 17
<223> OTHER INFORMATION: Bases at these positions are RNA
<220> FEATURE:
<221> NAME/KEY: misc_feature
<222> LOCATION: (1)..(17)
<223> OTHER INFORMATION: n is a, c, g, t or u

<400> SEQUENCE: 3
nnnnnnnnnn nnnnnn                                                   17

<210> SEQ ID NO 4
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: 1, 2, 3, 5, 13, 14, 15
<223> OTHER INFORMATION: Bases at these positions are RNA
<220> FEATURE:
<221> NAME/KEY: misc_feature
<222> LOCATION: (1)..(15)
<223> OTHER INFORMATION: n is a, c, g, t or u

<400> SEQUENCE: 4
nnnnnnnnnn nnnnn                                                    15

<210> SEQ ID NO 5
<211> LENGTH: 19
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: 1, 2, 3, 4, 5, 15, 16, 17, 18, 19
<223> OTHER INFORMATION: Bases at these positions are RNA
<220> FEATURE:
<221> NAME/KEY: misc_feature
<222> LOCATION: (1)..(19)
<223> OTHER INFORMATION: n is a, c, g, t or u

<400> SEQUENCE: 5
nnnnnnnnnn nnnnnnnnn                                                19

<210> SEQ ID NO 6
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: 1, 2, 12, 13, 14, 15
<223> OTHER INFORMATION: Bases at these positions are RNA
<220> FEATURE:
<221> NAME/KEY: misc_feature
<222> LOCATION: (1)..(15)
<223> OTHER INFORMATION: n is a, c, g, t or u
```

```
<400> SEQUENCE: 6
nnnnnnnnnn nnnnn                                                    15

<210> SEQ ID NO 7
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: 1, 2, 3, 4, 14, 15
<223> OTHER INFORMATION: Bases at these positions are RNA
<220> FEATURE:
<221> NAME/KEY: misc_feature
<222> LOCATION: (1)..(15)
<223> OTHER INFORMATION: n is a, c, g, t or u

<400> SEQUENCE: 7
nnnnnnnnnn nnnnn                                                    15

<210> SEQ ID NO 8
<211> LENGTH: 17
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: 1, 2, 3, 4, 14, 15, 16, 17
<223> OTHER INFORMATION: Bases at these positions are RNA
<220> FEATURE:
<221> NAME/KEY: misc_feature
<222> LOCATION: (1)..(17)
<223> OTHER INFORMATION: n is a, c, g, t or u

<400> SEQUENCE: 8
nnnnnnnnnn nnnnnnn                                                  17

<210> SEQ ID NO 9
<211> LENGTH: 17
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: 1, 2, 3, 4, 6, 14, 15, 16, 17
<223> OTHER INFORMATION: Bases at these positions are RNA
<220> FEATURE:
<221> NAME/KEY: misc_feature
<222> LOCATION: (1)..(17)
<223> OTHER INFORMATION: n is a, c, g, t or u

<400> SEQUENCE: 9
nnnnnnnnnn nnnnnnn                                                  17

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: 1, 2, 3, 4, 5, 16, 17, 18, 19, 20
<223> OTHER INFORMATION: Bases at these positions are RNA
<220> FEATURE:
<221> NAME/KEY: misc_feature
<222> LOCATION: (1)..(20)
<223> OTHER INFORMATION: n is a, c, g, t or u
```

```
<400> SEQUENCE: 10
nnnnnnnnnn nnnnnnnnnn                                           20

<210> SEQ ID NO 11
<211> LENGTH: 17
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: 1, 2, 3, 4, 13, 14, 15, 16, 17
<223> OTHER INFORMATION: Bases at these positions are RNA
<220> FEATURE:
<221> NAME/KEY: misc_feature
<222> LOCATION: (1)..(17)
<223> OTHER INFORMATION: n is a, c, g, t or u

<400> SEQUENCE: 11
nnnnnnnnnn nnnnnnn                                              17
```

ANTISENSE COMPOUNDS AND USES THEREOF

SEQUENCE LISTING

The present application is being filed along with a Sequence Listing in electronic format. The Sequence Listing is provided as a file entitled CORE0110USC1SEQ_ST25.txt, created Oct. 18, 2018, which is 4 Kb in size. The information in the electronic format of the sequence listing is incorporated herein by reference in its entirety.

BACKGROUND

Antisense compounds have been used to modulate target nucleic acids. Antisense compounds comprising a variety of chemical modifications and motifs have been reported. In certain instances, such compounds are useful as research tools, diagnostic reagents, and as therapeutic agents. In certain instances antisense compounds have been shown to modulate protein expression by binding to a target messenger RNA (mRNA) encoding the protein. In certain instances, such binding of an antisense compound to its target mRNA results in cleavage of the mRNA. Antisense compounds that modulate processing of a pre-mRNA have also been reported. Such antisense compounds alter splicing, interfere with polyadenlyation or prevent formation of the 5'-cap of a pre-mRNA.

SUMMARY

In certain embodiments, the present invention provides oligomeric compounds comprising oligonucleotides. In certain embodiments, such oligonucleotides comprise a region having a gapmer motif. In certain embodiments, such oligonucleotides consist of a region having a gapmer motif.

The present invention includes, but is not limited to the following numbered embodiments:

Embodiment 1. A oligomeric compound comprising a modified oligonucleotide consisting of 10 to 30 linked nucleosides, wherein the modified oligonucleotide has a sugar motif comprising:
  a 5'-region consisting of 2-8 linked 5'-region nucleosides, each independently selected from among a modified nucleoside and an unmodified deoxynucleoside, provided that at least one 5'-region nucleoside is a modified nucleoside and wherein the 3'-most 5'-region nucleoside is a modified nucleoside;
  a 3'-region consisting of 2-8 linked 3'-region nucleosides, each independently selected from among a modified nucleoside and an unmodified deoxynucleoside, provided that at least one 3'-region nucleoside is a modified nucleoside and wherein the 5'-most 3'-region nucleoside is a modified nucleoside; and
  a central region between the 5'-region and the 3'-region consisting of 5-10 linked central region nucleosides, each independently selected from among: a modified nucleoside and an unmodified deoxynucleoside, wherein the 5'-most central region nucleoside is an unmodified deoxynucleoside and the 3'-most central region nucleoside is an unmodified deoxynucleoside, and wherein the oligomeric compound comprises one or more phosphodiester internucleoside linkages and one or more phosphorothioate internucleoside linkages.

Embodiment 2. The oligomeric compound of embodiment 1, wherein the 5'-region consists of 8 linked 5'-region nucleosides.

Embodiment 3. The oligomeric compound of embodiment 1, wherein the 5'-region consists of 7 linked 5'-region nucleosides.

Embodiment 4. The oligomeric compound of embodiment 1, wherein the 5'-region consists of 6 linked 5'-region nucleosides.

Embodiment 5. The oligomeric compound of embodiment 1, wherein the 5'-region consists of 5 linked 5'-region nucleosides.

Embodiment 6. The oligomeric compound of embodiment 1, wherein the 5'-region consists of 4 linked 5'-region nucleosides.

Embodiment 7. The oligomeric compound of embodiment 1, wherein the 5'-region consists of 3 linked 5'-region nucleosides.

Embodiment 8. The oligomeric compound of embodiment 1, wherein the 5'-region consists of 2 linked 5'-region nucleosides.

Embodiment 9. The oligomeric compound of embodiment 1, wherein the 5'-region consists of 8 linked 5'-region nucleosides.

Embodiment 10. The oligomeric compound of any of embodiments 1 to 9, wherein the 3'-region consists of 8 linked 3'-region nucleosides.

Embodiment 11. The oligomeric compound of any of embodiments 1 to 9, wherein the 3'-region consists of 7 linked 3'-region nucleosides.

Embodiment 12. The oligomeric compound of any of embodiments 1 to 9, wherein the 3'-region consists of 6 linked 3'-region nucleosides.

Embodiment 13. The oligomeric compound of any of embodiments 1 to 9, wherein the 3'-region consists of 5 linked 3'-region nucleosides.

Embodiment 14. The oligomeric compound of any of embodiments 1 to 9, wherein the 3'-region consists of 4 linked 3'-region nucleosides.

Embodiment 15. The oligomeric compound of any of embodiments 1 to 9, wherein the 3'-region consists of 3 linked 3'-region nucleosides.

Embodiment 16. The oligomeric compound of any of embodiments 1 to 9, wherein the 3'-region consists of 2 linked 3'-region nucleosides.

Embodiment 17. The oligomeric compound of any of embodiments 1 to 16, wherein the central region consists of 10 linked central region nucleosides.

Embodiment 18. The oligomeric compound of any of embodiments 1 to 16, wherein the central region consists of 9 linked central region nucleosides.

Embodiment 19. The oligomeric compound of any of embodiments 1 to 16, wherein the central region consists of 8 linked central region nucleosides.

Embodiment 20. The oligomeric compound of any of embodiments 1 to 16, wherein the central region consists of 7 linked central region nucleosides.

Embodiment 21. The oligomeric compound of any of embodiments 1 to 16, wherein the central region consists of 6 linked central region nucleosides.

Embodiment 22. The oligomeric compound of any of embodiments 1 to 16, wherein the central region consists of 5 linked central region nucleosides.

Embodiment 23. The oligomeric compound of any of embodiments 1 to 22, wherein each central region nucleoside is an unmodified deoxynucleoside.

Embodiment 24. The oligomeric compound of any of embodiments 1 to 22, wherein at least one central region nucleoside is a modified nucleoside.

Embodiment 25. The oligomeric compound of embodiment 24, wherein one central region nucleoside is a modified nucleoside and each of the other central region nucleosides is an unmodified deoxynucleoside.

Embodiment 26. The oligomeric compound of embodiment 24, wherein two central region nucleosides are modified nucleosides and each of the other central region nucleosides is an unmodified deoxynucleoside.

Embodiment 27. The oligomeric compound of any of embodiments 24 to 26 wherein at least one modified central region nucleoside is an RNA-like nucleoside.

Embodiment 28. The oligomeric compound of any of embodiments 24 to 26 comprising at least one modified central region nucleoside comprising a modified sugar moiety.

Embodiment 29. The oligomeric compound of any of embodiments 24 to 28 comprising at least one modified central region nucleoside comprising a 5'-methyl-2'-deoxy sugar moiety.

Embodiment 30. The oligomeric compound of any of embodiments 24 to 28 comprising at least one modified central region nucleoside comprising a bicyclic sugar moiety.

Embodiment 31. The oligomeric compound of any of embodiments 24 to 30 comprising at least one modified central region nucleoside comprising a cEt sugar moiety.

Embodiment 32. The oligomeric compound of any of embodiments 24 to 31 comprising at least one modified central region nucleoside comprising an LNA sugar moiety.

Embodiment 33. The oligomeric compound of any of embodiments 24 to 32 comprising at least one modified central region nucleoside comprising an α-LNA sugar moiety.

Embodiment 34. The oligomeric compound of any of embodiments 24 to 32 comprising at least one modified central region nucleoside comprising a 2'-substituted sugar moiety.

Embodiment 35. The oligomeric compound of embodiment 34 wherein at least one modified central region nucleoside comprises a 2'-substituted sugar moiety comprising a 2' substituent selected from among: halogen, optionally substituted allyl, optionally substituted amino, azido, optionally substituted SH, CN, OCN, CF3, OCF3, O, S, or N(Rm)-alkyl; O, S, or N(Rm)-alkenyl; O, S or N(Rm)-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, O(CH2)2SCH3, O—(CH2)2-O—N(Rm)(Rn) or O—CH2-C(=O)—N(Rm)(Rn), where each Rm and Rn is, independently, H, an amino protecting group or substituted or unsubstituted $C_1$-$C_{10}$ alkyl;
wherein each optionally substituted group is optionally substituted with a substituent group independently selected from among: hydroxyl, amino, alkoxy, carboxy, benzyl, phenyl, nitro ($NO_2$), thiol, thioalkoxy (S-alkyl), halogen, alkyl, aryl, alkenyl and alkynyl.

Embodiment 36. The oligomeric compound of embodiment 35 wherein at least one modified central region nucleoside comprises a 2'-substituted sugar moiety comprising a 2' substituent selected from among: a halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—$CH=CH_2$, $O(CH_2)_2$—$OCH_3$, $O(CH_2)_2$—$SCH_3$, $O(CH_2)_2$—$OCF_3$, $O(CH_2)_3$—$N(R_1)(R_2)$, $O(CH_2)_2$—$ON(R_1)(R_2)$, $O(CH_2)_2$—$O(CH_2)_2$—$N(R_1)(R_2)$, $OCH_2C(=O)$—$N(R_1)(R_2)$, $OCH_2C(=O)$—$N(R_3)$—$(CH_2)_2$—$N(R_1)(R_2)$, and $O(CH_2)_2$—$N(R_3)$—$C(=NR_4)[N(R_1)(R_2)]$; wherein $R_1$, $R_2$, $R_3$ and $R_4$ are each, independently, H or $C_1$-$C_6$ alkyl.

Embodiment 37. The oligomeric compound of embodiment 36 wherein the 2' substituent is selected from among: a halogen, $OCH_3$, $OCF_3$, $OCH_2CH_3$, $OCH_2CF_3$, $OCH_2$—$CH=CH_2$, $O(CH_2)_2$—$OCH_3$ (MOE), $O(CH_2)_2$—$O(CH_2)_2$—$N(CH_3)_2$, $OCH_2C(=O)$—$N(H)CH_3$, $OCH_2C(=O)$—$N(H)$—$(CH_2)_2$—$N(CH_3)_2$, and $OCH_2$—$N(H)$—$C(=NH)NH_2$.

Embodiment 38. The oligomeric compound of any of embodiments 24 to 37 comprising at least one modified central region nucleoside comprising a 2'-MOE sugar moiety.

Embodiment 39. The oligomeric compound of any of embodiments 24 to 38 comprising at least one modified central region nucleoside comprising a 2'-OMe sugar moiety.

Embodiment 40. The oligomeric compound of any of embodiments 24 to 39 comprising at least one modified central region nucleoside comprising a 2'-F sugar moiety.

Embodiment 41. The oligomeric compound of any of embodiments 24 to 40 comprising at least one modified central region nucleoside comprising a 2'-(ara)-F sugar moiety.

Embodiment 42. The oligomeric compound of any of embodiments 21 to 38 comprising at least one modified central region nucleoside comprising a sugar surrogate.

Embodiment 43. The oligomeric compound of embodiment 42 comprising at least one modified central region nucleoside comprising an F-HNA sugar moiety.

Embodiment 44. The oligomeric compound of embodiment 42 or 43 comprising at least one modified central region nucleoside comprising an HNA sugar moiety.

Embodiment 45. The oligomeric compound of any of embodiments 24 to 44 comprising at least one modified central region nucleoside comprising a modified nucleobase.

Embodiment 46. The oligomeric compound of embodiment 45 comprising at least one modified central region nucleoside comprising a modified nucleobase selected from a 2-thio pyrimidine and a 5-propyne pyrimidine.

Embodiment 47. The oligomeric compound of any of embodiments 24 to 46, wherein the $2^{nd}$ nucleoside from the 5'-end of the central region is a modified nucleoside.

Embodiment 48. The oligomeric compound of any of embodiments 24 to 47, wherein the $3^{rd}$ nucleoside from the 5'-end of the central region is a modified nucleoside.

Embodiment 49. The oligomeric compound of any of embodiments 24 to 48, wherein the $4^{th}$ nucleoside from the 5'-end of the central region is a modified nucleoside.

Embodiment 50. The oligomeric compound of any of embodiments 24 to 49, wherein the $5^{th}$ nucleoside from the 5'-end of the central region is a modified nucleoside.

Embodiment 51. The oligomeric compound of any of embodiments 24 to 50, wherein the 6$^{th}$ nucleoside from the 5'-end of the central region is a modified nucleoside.

Embodiment 52. The oligomeric compound of any of embodiments 24 to 51, wherein the 8$^{th}$ nucleoside from the 3'-end of the central region is a modified nucleoside.

Embodiment 53. The oligomeric compound of any of embodiments 24 to 52, wherein the 7$^{th}$ nucleoside from the 3'-end of the central region is a modified nucleoside.

Embodiment 54. The oligomeric compound of any of embodiments 24 to 53, wherein the 6$^{th}$ nucleoside from the 3'-end of the central region is a modified nucleoside.

Embodiment 55. The oligomeric compound of any of embodiments 24 to 54, wherein the 5$^{th}$ nucleoside from the 3'-end of the central region is a modified nucleoside.

Embodiment 56. The oligomeric compound of any of embodiments 24 to 55, wherein the 4$^{th}$ nucleoside from the 3'-end of the central region is a modified nucleoside.

Embodiment 57. The oligomeric compound of any of embodiments 24 to 56, wherein the 3$^{rd}$ nucleoside from the 3'-end of the central region is a modified nucleoside.

Embodiment 58. The oligomeric compound of any of embodiments 24 to 57, wherein the 2$^{nd}$ nucleoside from the 3'-end of the central region is a modified nucleoside.

Embodiment 59. The oligomeric compound of any of embodiments 24 to 58, wherein the modified nucleoside is a 5'-methyl-2'-deoxy sugar moiety.

Embodiment 60. The oligomeric compound of any of embodiments 24 to 59, wherein the modified nucleoside is a 2-thio pyrimidine.

Embodiment 61. The oligomeric compound of any of embodiments 24 to 58, wherein the central region comprises no region having more than 4 contiguous unmodified deoxynucleosides.

Embodiment 62. The oligomeric compound of any of embodiments 24 to 58, wherein the central region comprises no region having more than 5 contiguous unmodified deoxynucleosides.

Embodiment 63. The oligomeric compound of any of embodiments 24 to 58, wherein the central region comprises no region having more than 6 contiguous unmodified deoxynucleosides.

Embodiment 64. The oligomeric compound of any of embodiments 24 to 58, wherein the central region comprises no region having more than 7 contiguous unmodified deoxynucleosides.

Embodiment 65. The oligomeric compound of any of embodiments 1 to 17 or 22 to 64, wherein the central region has a nucleoside motif selected from among: DDDDDDDDDD, DDDDXDDDDD; DDDDDXDDDDD; DDDXDDDDD; DDDDXDDDDD; DDDDXDDDD; DDXDDDDDD; DDDXDDDDDD; DXDDDDDDD; DDXDDDDDDD; DDXDDDDD; DDXDDDXDDD; DDDXDDDXDDD; DXDDDXDDD; DDXDDDXDD; DDXDDDDXDDD; DDXDDDDXDD; DXDDDDXDDD; DDDDXDDD; DDDXDDD; DXDDDDDDD; DDDDXXDDD; and DXXDXXDXX; wherein
each D is an unmodified deoxynucleoside; and each X is a modified nucleoside.

Embodiment 66. The oligomeric compound of any of embodiments 1 to 18 or 22 to 64, wherein the central region has a nucleoside motif selected from among: DDDDDDDDD; DXDDDDDDD; DDXDDDDDD; DDDXDDDDD; DDDDXDDDD; DDDDDXDDD; DDDDDDXDD; DDDDDDDXD; DXXDDDDDD; DDDDDDXXD; DDXXDDDDD; DDDXXDDDD; DDDDXXDDD; DDDDDXXDD; DXDDDDDXD; DXDDDDXDD; DXDDDXDDD; DXDDXDDDD; DXDXDDDDD; DDXDDDDXD; DDXDDDXDD; DDXDDXDDD; DDXDXDDDD; DDDXDDDXD; DDDXDDXDD; DDDXDXDDD; DDDDXDDXD; DDDDXDXDD; DDDDDXDXD; and DDDDDXDXD wherein each D is an unmodified deoxynucleoside; and each X is a modified nucleoside.

Embodiment 67. The oligomeric compound of any of embodiments 1 to 18 or 22 to 64, wherein the central region has a nucleoside motif selected from among: DDDDDDDD, DDDDXDDDD, DXDDDDDDD, DXXDDDDDD, DDXDDDDDD, DDDXDDDDD, DDDDXDDDD, DDDDDXDDD, DDDDDDXDD, and DDDDDDDXD.

Embodiment 68. The oligomeric compound of any of embodiments 1 to 19 or 22 to 64, wherein the central region has a nucleoside motif selected from among: DDDDDDDD, DXDDDDDD, DDXDDDDD, DDDXDDDD, DDDDXDDD, DDDDDXDD, DDDDDDXD, DXDDDXD, DXDDDXDD, DXDDXDDD, DXDXDDDD, DXXDDDDD, DDXXDDDD, DDXDXDDD, DDXDDXDD, DDXDDDXD, DDDXDDXD, DDDXDXDD, DDDDXXDD, DDDDXDXD, and DDDDDXXDD.

Embodiment 69. The oligomeric compound of any of embodiments 1 to 20 or 22 to 64, wherein the central region has a nucleoside motif selected from among: DDDDDDD, DXDDDDD, DDXDDDD, DDDXDDD, DDDDXDD, DDDDDXD, DXDDXDD, DXDDXDD, DXDXDDD, DXXDDDD, DDXXDDD, DDXDXDD, DDXDDXD, DDDXXDD, DDDXDXD, and DDDDXXD.

Embodiment 70. The oligomeric compound of any of embodiments 1 to 21 or 22 to 64, wherein the central region has a nucleoside motif selected from among: DDDDDD, DXDDDD, DDXDDD, DDDXDD, DDDDXD, DXXDDD, DXDXDD, DXDDXD, DDXXDD, DDXDXD, DDDXXD, DDDDD, DXDDD, DDXDD, DDDXD, DXXDD, DXDXD, and DDXXD.

Embodiment 71. The oligomeric compound of any of embodiments 1 to 21 or 22 to 64, wherein the central region has a nucleoside motif selected from among: DDDDDD, DDDDDDD, DDDDDDDD, DDDDDDDDD, DDDDDDDDDD, DXDDDD, DDXDDD, DDDXDD, DDDDXD, DXDDDDD, DDXDDDD, DDDXDDD, DDDDXDD, DDDDDXD, DXDDDDDD, DDXDDDDD, DDDXDDDD, DDDDXDDD, DDDDDXDD, DDDDDDXD, DXDDDDDDD, DDXDDDDDD, DDDXDDDDD, DDDDXDDDD, DDDDDXDDD, DDDDDDXDD, DDDDDDDXD, DXDDDDDDDD, DDXDDDDDDD, DDDXDDDDDD, DDDDXDDDDD, DDDDDXDDDD, DDDDDDXDDD, DDDDDDDXDD, and DDDDDDDDXD.

Embodiment 72. The oligomeric compound of embodiments 65 to 71, wherein each X comprises a modified nucleobase.

Embodiment 73. The oligomeric compound of embodiments 65 to 71, wherein each X comprises a modified sugar moiety.

Embodiment 74. The oligomeric compound of embodiments 65 to 71, wherein each X comprises 2-thio-thymidine.

Embodiment 75. The oligomeric compound of embodiments 65 to 71, wherein each X nucleoside comprises an F-HNA sugar moiety.

Embodiment 76. The oligomeric compound of embodiments 65 to 71, wherein the nucleobase sequence of the target region of the target nucleic acid differs from the nucleobase sequence of at least one non-target nucleic acid by a single differentiating nucleobase, and wherein the location of the single differentiating nucleobase is represented by X.

Embodiment 77. The oligomeric compound of embodiment 76, wherein the target nucleic acid and the non-target nucleic acid are alleles of the same gene.

Embodiment 78. The oligomeric compound of embodiment 76, wherein the single differentiating nucleobase is a single-nucleotide polymorphism.

Embodiment 79. The oligomeric compound of any of embodiments 1-79, wherein at least one 5'-region nucleoside is an unmodified deoxynucleoside.

Embodiment 80. The oligomeric compound of any of embodiments 1-79, wherein each 5'-region nucleoside is a modified nucleoside.

Embodiment 81. The oligomeric compound of any of embodiments 1-79, wherein at least one 5'-region nucleoside is an RNA-like nucleoside.

Embodiment 82. The oligomeric compound of any of embodiments 1-79, wherein each 5'-region nucleoside is an RNA-like nucleoside.

Embodiment 83. The oligomeric compound of any of embodiments 1-79, comprising at least one modified 5'-region nucleoside comprising a modified sugar.

Embodiment 84. The oligomeric compound of embodiment 1-79, comprising at least one modified 5'-region nucleoside comprising a bicyclic sugar moiety.

Embodiment 85. The oligomeric compound of embodiment 1-79, comprising at least one modified 5'-region nucleoside comprising a cEt sugar moiety.

Embodiment 86. The oligomeric compound of embodiment 1-79, comprising at least one modified 5'-region nucleoside comprising an LNA sugar moiety.

Embodiment 87. The oligomeric compound of any of embodiments 1-79, comprising of at least one modified 5'-region nucleoside comprising a 2'-substituted sugar moiety.

Embodiment 88. The oligomeric compound of embodiment 1-79, wherein at least one modified 5'-region nucleoside comprises a 2'-substituted sugar moiety comprising a 2' substituent selected from among: halogen, optionally substituted allyl, optionally substituted amino, azido, optionally substituted SH, CN, OCN, $CF_3$, $OCF_3$, O, S, or $N(R_m)$-alkyl; O, S, or $N(R_m)$-alkenyl; O, S or $N(R_m)$-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, $O(CH_2)_2SCH_3$, $O—(CH_2)_2—O—N(R_m)(R_n)$ or $O—CH_2—C(=O)—N(R_m)(R_n)$, where each $R_m$ and $R_n$ is, independently, H, an amino protecting group or substituted or unsubstituted $C_1$-$C_{10}$ alkyl;

wherein each optionally substituted group is optionally substituted with a substituent group independently selected from among: hydroxyl, amino, alkoxy, carboxy, benzyl, phenyl, nitro ($NO_2$), thiol, thioalkoxy (S-alkyl), halogen, alkyl, aryl, alkenyl and alkynyl.

Embodiment 89. The oligomeric compound of embodiment 1-79, wherein at least one modified 5'-region nucleoside comprises a 2'-substituted sugar moiety comprising a 2'-substituent selected from among: a halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2—CH=CH_2$, $O(CH_2)_2—OCH_3$ (MOE), $O(CH_2)_2—SCH_3$, $O(CH_2)_2—OCF_3$, $O(CH_2)_3—N(R_1)(R_2)$, $O(CH_2)_2—ON(R_1)(R_2)$, $O(CH_2)_2—O(CH_2)_2—N(R_1)(R_2)$, $OCH_2C(=O)—N(R_1)(R_2)$, $OCH_2C(=O)—N(R_3)—(CH_2)_2—N(R_1)(R_2)$, and $O(CH_2)_2—N(R_3)—C(=NR_4)[N(R_1)(R_2)]$; wherein $R_1$, $R_2$, $R_3$ and $R_4$ are each, independently, H or $C_1$-$C_6$ alkyl.

Embodiment 90. The oligomeric compound of embodiment 89, wherein the 2'-substituent is selected from among: a halogen, $OCH_3$, $OCF_3$, $OCH_2CH_3$, $OCH_2CF_3$, $OCH_2—CH=CH_2$, $O(CH_2)_2—OCH_3$, $O(CH_2)_2—O(CH_2)_2—N(CH_3)_2$, $OCH_2C(=O)—N(H)CH_3$, $OCH_2C(=O)—N(H)—(CH_2)_2—N(CH_3)_2$, and $OCH_2—N(H)—C(=NH)NH_2$.

Embodiment 91. The oligomeric compound of any of embodiments 1-79, comprising at least one modified 5'-region nucleoside comprising a 2'-MOE sugar moiety.

Embodiment 92. The oligomeric compound of any of embodiments 1-79, comprising at least one modified 5'-region nucleoside comprising a 2'-OMe sugar moiety.

Embodiment 93. The oligomeric compound of any of embodiments 1-79, comprising at least one modified 5'-region nucleoside comprising a 2'-F sugar moiety.

Embodiment 94. The oligomeric compound of any of embodiments 1-79, comprising at least one modified 5'-region nucleoside comprising a 2'-(ara)-F sugar moiety.

Embodiment 95. The oligomeric compound of any of embodiments 1-79, comprising of at least one modified 5'-region nucleoside comprising a sugar surrogate.

Embodiment 96. The oligomeric compound of embodiment 1-79, comprising at least one modified 5'-region nucleoside comprising an F-HNA sugar moiety.

Embodiment 97. The oligomeric compound of embodiment 1-79, comprising at least one modified 5'-region nucleoside comprising an HNA sugar moiety.

Embodiment 98. The oligomeric compound of any of embodiments 1-97, comprising at least one modified 5'-region nucleoside comprising a modified nucleobase.

Embodiment 99. The oligomeric compound of embodiment 98, wherein the modified nucleoside comprises 2-thio-thymidine.

Embodiment 100. The oligomeric compound of any of embodiments 1-99, wherein the 5'-region has a motif selected from among:

ADDA; ABDAA; ABBA; ABB; ABAA; AABAA; AAABAA; AAAABAA; AAAAABAA; AAABAA; AABAA; ABAB; ABADB; ABADDB; AAABB; AAAAA; ABBDC; ABDDC; ABBDCC; ABBDDC; ABBDCC; ABBC; AA; AAA; AAAA; AAAAB; AAAAAAA; AAAAAAAA; ABBB; AB; ABAB; AAAAB; AABBB; AAAAB; and AABBB, wherein each A is a modified nucleoside of a first type, each B is a modified nucleoside of a second type, each C is a modified nucleoside of a third type, and each D is an unmodified deoxynucleoside.

Embodiment 101. The oligomeric compound of any of embodiments 1-100, wherein the 5'-region has a motif selected from among:
AB, ABB, AAA, BBB, BBBAA, AAB, BAA, BBAA, AABB, AAAB, ABBW, ABBWW, ABBB, ABBBB, ABAB, ABABAB, ABABBB, ABABAA, AAABB, AAAABB, AABB, AAAAB, AABBB, ABBBB, BBBBB, AAABW, AAAAA, BBBBAA, and AAABW wherein each A is a modified nucleoside of a first type, each B is a modified nucleoside of a second type, and each W is a modified nucleoside of a third type.

Embodiment 102. The oligomeric compound of any of embodiments 1-100, wherein the 5'-region has a motif selected from among: ABB; ABAA; AABAA; AAA-BAA; ABAB; ABADB; AAABB; AAAAA; AA; AAA; AAAA; AAAAB; ABBB; AB; and ABAB, wherein each A is a modified nucleoside of a first type, each B is a modified nucleoside of a second type, and each W is a modified nucleoside of a third type.

Embodiment 103. The oligomeric compound of embodiments 100-102, wherein each A nucleoside comprises a 2'-substituted sugar moiety.

Embodiment 104. The oligomeric compound of embodiment 100-103, wherein each A nucleoside comprises a 2'-substituted sugar moiety comprising a 2'-substituent selected from among: a halogen, $OCH_3$, $OCF_3$, $OCH_2CH_3$, $OCH_2CF_3$, $OCH_2—CH=CH_2$, $O(CH_2)_2—OCH_3$, $O(CH_2)_2—O(CH_2)_2—N(CH_3)_2$, $OCH_2C(=O)—N(H)CH_3$, $OCH_2C(=O)—N(H)—(CH_2)_2—N(CH_3)_2$, and $OCH_2—N(H)—C(=NH)NH_2$.

Embodiment 105. The oligomeric compound of embodiment 104, wherein each A nucleoside comprises a 2'-substituted sugar moiety comprising a 2'-substituent selected from among: F, $OCH_3$, $O(CH_2)_2—OCH_3$.

Embodiment 106. The oligomeric compound of embodiments 100-103, wherein each A nucleoside comprises a bicyclic sugar moiety.

Embodiment 107. The oligomeric compound of embodiment 106, wherein each A nucleoside comprises a bicyclic sugar moiety selected from among: cEt, cMOE, LNA, α-LNA, ENA and 2'-thio LNA.

Embodiment 108. The oligomeric compound of any of embodiments 100-107, wherein each A comprises a modified nucleobase.

Embodiment 109. The oligomeric compound of embodiment 108, wherein each A comprises a modified nucleobase selected from among a 2-thio pyrimidine and a 5-propyne pyrimidine.

Embodiment 110. The oligomeric compound of embodiment 109, wherein each A comprises 2-thio-thymidine.

Embodiment 111. The oligomeric compound of embodiment 100-103, wherein each A nucleoside comprises an unmodified 2'-deoxyfuranose sugar moiety.

Embodiment 112. The oligomeric compound of embodiment 100-103, wherein each A nucleoside comprises an F-HNA sugar moiety.

Embodiment 113. The oligomeric compound of any of embodiments 100-112, wherein each B nucleoside comprises a 2'-substituted sugar moiety.

Embodiment 114. The oligomeric compound of embodiment 113, wherein at least one central region nucleoside comprises a 2'-substituted sugar moiety comprising a 2' substituent selected from among: halogen, optionally substituted allyl, optionally substituted amino, azido, optionally substituted SH, CN, OCN, $CF_3$, $OCF_3$, O, S, or $N(R_m)$-alkyl; O, S, or $N(R_m)$-alkenyl; O, S or $N(R_m)$-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, $O(CH_2)_2SCH_3$, $O—(CH_2)_2—O—N(R_m)(R_n)$ or $O—CH_2—C(=O)—N(R_m)(R_n)$, where each $R_m$ and $R_n$ is, independently, H, an amino protecting group or substituted or unsubstituted $C_1$-$C_{10}$ alkyl; wherein each optionally substituted group is optionally substituted with a substituent group independently selected from among: hydroxyl, amino, alkoxy, carboxy, benzyl, phenyl, nitro ($NO_2$), thiol, thioalkoxy (S-alkyl), halogen, alkyl, aryl, alkenyl and alkynyl.

Embodiment 115. The oligomeric compound of embodiment 114, wherein each B nucleoside comprises a 2'-substituted sugar moiety comprising a 2'-substituent selected from among: a halogen, $OCH_3$, $OCF_3$, $OCH_2CH_3$, $OCH_2CF_3$, $OCH_2—CH=CH_2$, $O(CH_2)_2—OCH_3O(CH_2)_2—O(CH_2)_2—N(CH_3)_2$, $OCH_2C(=O)—N(H)CH_3$, $OCH_2C(=O)—N(H)—(CH_2)_2—N(CH_3)_2$, and $OCH_2—N(H)—C(=NH)NH_2$.

Embodiment 116. The oligomeric compound of embodiment 115, wherein each B nucleoside comprises a 2'-substituted sugar moiety comprising a 2'-substituent selected from among: F, $OCH_3$, $O(CH_2)_2—OCH_3$.

Embodiment 117. The oligomeric compound of any of embodiments 100-112, wherein each B nucleoside comprises a bicyclic sugar moiety.

Embodiment 118. The oligomeric compound of embodiment 117, wherein each B nucleoside comprises a bicyclic sugar moiety selected from among: cEt, cMOE, LNA, α-LNA, ENA and 2'-thio LNA.

Embodiment 119. The oligomeric compound of any of embodiments 100-112, wherein each B comprises a modified nucleobase.

Embodiment 120. The oligomeric compound of embodiment 119, wherein each B comprises a modified nucleobase selected from among a 2-thio pyrimidine and a 5-propyne pyrimidine.

Embodiment 121. The oligomeric compound of embodiment 120, wherein each B comprises 2-thio-thymidine.

Embodiment 122. The oligomeric compound of embodiment 100-103, wherein each B nucleoside comprises an unmodified 2'-deoxyfuranose sugar moiety.

Embodiment 123. The oligomeric compound of embodiment 100-112, wherein each B nucleoside comprises an F-HNA sugar moiety.

Embodiment 124. The oligomeric compound of any of embodiments 100-123, wherein each C nucleoside comprises a 2'-substituted sugar moiety.

Embodiment 125. The oligomeric compound of embodiment 124, wherein at least one 5'-region nucleoside comprises a 2'-substituted sugar moiety comprising a 2' substituent selected from among: halogen, optionally substituted allyl, optionally substituted amino, azido, optionally substituted SH, CN, OCN, $CF_3$, $OCF_3$, O, S, or $N(R_m)$-alkyl; O, S, or $N(R_m)$-alkenyl; O, S or $N(R_m)$-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, $O(CH_2)_2SCH_3$, $O—(CH_2)_2—O—N(R_m)(R_n)$ or $O—CH_2—C(=O)—N(R_m)(R_n)$, where each $R_m$ and $R_n$ is, independently, H, an amino protecting group or substituted or unsubstituted $C_1$-$C_{10}$ alkyl; wherein each optionally substituted group is optionally substituted with a substituent group independently selected from among: hydroxyl, amino, alkoxy, carboxy, benzyl, phenyl, nitro ($NO_2$), thiol, thioalkoxy (S-alkyl), halogen, alkyl, aryl, alkenyl and alkynyl.

Embodiment 126. The oligomeric compound of embodiment 125, wherein each C nucleoside comprises a 2'-substituted sugar moiety comprising a 2'-substituent selected from among: a halogen, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C(=O)$—$N(H)CH_3$, $OCH_2C(=O)$—N(H)—$(CH_2)_2$—$N(CH_3)_2$, and $OCH_2$—N(H)—$C(=NH)NH_2$.

Embodiment 127. The oligomeric compound of embodiment 126, wherein each C nucleoside comprises a 2'-substituted sugar moiety comprising a 2'-substituent selected from among: F, $OCH_3$, $O(CH_2)_2$—$OCH_3$.

Embodiment 128. The oligomeric compound of any of embodiments 100-123, wherein each C nucleoside comprises a bicyclic sugar moiety.

Embodiment 129. The oligomeric compound of embodiment 128, wherein each C nucleoside comprises a bicyclic sugar moiety selected from among: cEt, cMOE, LNA, α-LNA, ENA and 2'-thio LNA.

Embodiment 130. The oligomeric compound of any of embodiments 100-123, wherein each C comprises a modified nucleobase.

Embodiment 131. The oligomeric compound of embodiment 130, wherein each C comprises a modified nucleobase selected from among a 2-thio pyrimidine and a 5-propyne pyrimidine.

Embodiment 132. The oligomeric compound of embodiment 131, wherein each C comprises 2-thio-thymidine.

Embodiment 133. The oligomeric compound of embodiment 100-123, wherein each C comprises an F-HNA sugar moiety.

Embodiment 134. The oligomeric compound of embodiment 100-123, wherein each C nucleoside comprises an unmodified 2'-deoxyfuranose sugar moiety.

Embodiment 135. The oligomeric compound of any of embodiments 100-135, wherein each W nucleoside comprises a 2'-substituted sugar moiety.

Embodiment 136. The oligomeric compound of embodiment 135, wherein each W nucleoside comprises a 2'-substituted sugar moiety comprising a 2'-substituent selected from among: a halogen, $OCH_3$, $OCF_3$, $OCH_2CH_3$, $OCH_2CF_3$, $OCH_2$CH=$CH_2$, $O(CH_2)_2$—$OCH_3O(CH_2)_2$—$O(CH_2)_2$—$N(CH_3)_2$, $OCH_2C(=O)$—$N(H)CH_3$, $OCH_2C(=O)$—N(H)—$(CH_2)_2$—$N(CH_3)_2$, and $OCH_2$—N(H)—$C(=NH)NH_2$.

Embodiment 137. The oligomeric compound of embodiment 135, wherein each W nucleoside comprises a 2'-substituted sugar moiety comprising a 2'-substituent selected from among: F, $OCH_3$, $O(CH_2)_2$—$OCH_3$.

Embodiment 138. The oligomeric compound of any of embodiments 100-135, wherein each W nucleoside comprises a bicyclic sugar moiety.

Embodiment 139. The oligomeric compound of embodiment 138, wherein each W nucleoside comprises a bicyclic sugar moiety selected from among: cEt, cMOE, LNA, α-LNA, ENA and 2'-thio LNA.

Embodiment 140. The oligomeric compound of any of embodiments 100-135, wherein each W comprises a modified nucleobase.

Embodiment 141. The oligomeric compound of embodiment 140, wherein each W comprises a modified nucleobase selected from among a 2-thio pyrimidine and a 5-propyne pyrimidine.

Embodiment 142. The oligomeric compound of embodiment 141, wherein each W comprises 2-thio-thymidine.

Embodiment 143. The oligomeric compound of embodiment 100-135, wherein each W comprises an F-HNA sugar moiety.

Embodiment 144. The oligomeric compound of embodiment 100-135, wherein each W nucleoside comprises an unmodified 2'-deoxyfuranose sugar moiety.

Embodiment 145. The oligomeric compound of any of embodiments 1-144, wherein at least one 3'-region nucleoside is an unmodified deoxynucleoside.

Embodiment 146. The oligomeric compound of any of embodiments 1-145, wherein each 3'-region nucleoside is a modified nucleoside.

Embodiment 147. The oligomeric compound of any of embodiments 1-144, wherein at least one 3'-region nucleoside is an RNA-like nucleoside.

Embodiment 148. The oligomeric compound of any of embodiments 1-145, wherein each 3'-region nucleoside is an RNA-like nucleoside.

Embodiment 149. The oligomeric compound of any of embodiments 1-144, comprising at least one modified 3'-region nucleoside comprising a modified sugar.

Embodiment 150. The oligomeric compound of embodiment 149, comprising at least one modified 3'-region nucleoside comprising a bicyclic sugar moiety.

Embodiment 151. The oligomeric compound of embodiment 148, comprising at least one modified 3'-region nucleoside comprising a cEt sugar moiety.

Embodiment 152. The oligomeric compound of embodiment 150, comprising at least one modified 3'-region nucleoside comprising an LNA sugar moiety.

Embodiment 153. The oligomeric compound of any of embodiments 1-153 comprising of at least one modified 3'-region nucleoside comprising a 2'-substituted sugar moiety.

Embodiment 154. The oligomeric compound of embodiment 153 wherein at least one modified 3'-region nucleoside comprises a 2'-substituted sugar moiety comprising a 2'-substituent selected from among: a halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$ (MOE), $O(CH_2)_2$—$SCH_3$, $O(CH_2)_2$—$OCF_3$, $O(CH_2)_3$—$N(R_1)(R_2)$, $O(CH_2)_2$—$ON(R_1)(R_2)$, $O(CH_2)_2$—$O(CH_2)_2$—$N(R_1)(R_2)$, $OCH_2C(=O)$—$N(R_1)(R_2)$, $OCH_2C(=O)$—N($R_3$)—$(CH_2)_2$—$N(R_1)(R_2)$, and $O(CH_2)_2$—$N(R_3)$—$C(=NR_4)[N(R_1)(R_2)]$; wherein $R_1$, $R_2$, $R_3$ and $R_4$ are each, independently, H or $C_1$-$C_6$ alkyl.

Embodiment 155. The oligomeric compound of embodiment 154, wherein the 2'-substituent is selected from among: a halogen, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C(=O)$—$N(H)CH_3$, $OCH_2C(=O)$—N(H)—$(CH_2)_2$—$N(CH_3)_2$, and $OCH_2$—N(H)—$C(=NH)NH_2$.

Embodiment 156. The oligomeric compound of any of embodiments 152-155 comprising at least one modified 3'-region nucleoside comprising a 2'-MOE sugar moiety.

Embodiment 157. The oligomeric compound of any of embodiments 152-156 comprising at least one modified 3'-region nucleoside comprising a 2'-OMe sugar moiety.

Embodiment 158. The oligomeric compound of any of embodiments 152-157 comprising at least one modified 3'-region nucleoside comprising a 2'-F sugar moiety.

Embodiment 159. The oligomeric compound of any of embodiments 152-158 comprising at least one modified 3'-region nucleoside comprising a 2'-(ara)-F sugar moiety.

Embodiment 160. The oligomeric compound of any of embodiments 152-159 comprising of at least one modified 3'-region nucleoside comprising a sugar surrogate.

Embodiment 161. The oligomeric compound of embodiment 160 comprising at least one modified 3'-region nucleoside comprising an F-HNA sugar moiety.

Embodiment 162. The oligomeric compound of embodiment 160 comprising at least one modified 3'-region nucleoside comprising an HNA sugar moiety.

Embodiment 163. The oligomeric compound of any of embodiments 1-162 comprising at least one modified 3'-region nucleoside comprising a modified nucleobase.

Embodiment 164. The oligomeric compound of any of embodiments 1-163, wherein each A comprises a 2'-substituted sugar moiety comprising a 2'-substituent selected from among: F, $OCH_3$, $O(CH_2)_2$—$OCH_3$, and each B comprises a bicylic sugar moiety selected from among: LNA and cEt.

Embodiment 165. The oligomeric compound of embodiment 164, wherein each A comprises $O(CH_2)_2$—$OCH_3$ and each B comprises cEt.

Embodiment 166. The oligomeric compound of any of embodiments 1-165, wherein the 3'-region has a motif selected from among: ABB, ABAA, AAABAA, AAAAABAA, AABAA, AAAABAA, AAABAA, ABAB, AAAAA, AAABB, AAAAAAAA, AAAAAAA, AAAAAA, AAAAB, AAAA, AAA, AA, AB, ABBB, ABAB, AABBB, wherein each A is a modified nucleoside of a first type, each B is a modified nucleoside of a second type.

Embodiment 167. The oligomeric compound of embodiments 1-165, wherein the 3'-region has a motif selected from among: ABB; AAABAA; AABAA; AAAABAA; AAAAA; AAABB; AAAAAAAA; AAAAAAA; AAAAAA; AAAAB; AB; ABBB; and ABAB, wherein each A is a modified nucleoside of a first type, each B is a modified nucleoside of a second type.

Embodiment 168. The oligomeric compound of embodiments 1-165, wherein the 3'-region has a motif selected from among: BBA, AAB, AAA, BBB, BBAA, AABB, WBBA, WAAB, BBBA, BBBBA, BBBB, BBBBBA, ABBBBB, BBAAA, AABBB, BBBAA, BBBBA, BBBBB, BABA, AAAAA, BBAAAA, AABBBB, BAAAA, and ABBBB, wherein each A is a modified nucleoside of a first type, each B is a modified nucleoside of a second type, and each W is a modified nucleoside of a first type, a second type, or a third type.

Embodiment 169. The oligomeric compound of embodiments 166-168, wherein each A nucleoside comprises a 2'-substituted sugar moiety.

Embodiment 170. The oligomeric compound of embodiments 166-168, wherein at least one central region nucleoside comprises a 2'-substituted sugar moiety comprising a 2' substituent selected from among: halogen, optionally substituted allyl, optionally substituted amino, azido, optionally substituted SH, CN, OCN, $CF_3$, $OCF_3$, O, S, or $N(R_m)$-alkyl; O, S, or $N(R_m)$-alkenyl; O, S or $N(R_m)$-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, $O(CH_2)_2SCH_3$, O—$(CH_2)_2$—O—$N(R_m)(R_n)$ or O—$CH_2$—C(=O)—$N(R_m)(R_n)$, where each $R_m$ and $R_n$ is, independently, H, an amino protecting group or substituted or unsubstituted $C_1$-$C_{10}$ alkyl;
wherein each optionally substituted group is optionally substituted with a substituent group independently selected from among: hydroxyl, amino, alkoxy, carboxy, benzyl, phenyl, nitro ($NO_2$), thiol, thioalkoxy (S-alkyl), halogen, alkyl, aryl, alkenyl and alkynyl.

Embodiment 171. The oligomeric compound of embodiment 170, wherein each A nucleoside comprises a 2'-substituted sugar moiety comprising a 2'-substituent selected from among: a halogen, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C$(=O)—N(H)$CH_3$, $OCH_2C$(=O)—N(H)—$(CH_2)_2$—N$(CH_3)_2$, and $OCH_2$—N(H)—C(=NH)$NH_2$.

Embodiment 172. The oligomeric compound of embodiment 171, wherein each A nucleoside comprises a 2'-substituted sugar moiety comprising a 2'-substituent selected from among: F, $OCH_3$, $O(CH_2)_2$—$OCH_3$.

Embodiment 173. The oligomeric compound of embodiments 166-168, wherein each A nucleoside comprises a bicyclic sugar moiety.

Embodiment 174. The oligomeric compound of embodiment 173, wherein each A nucleoside comprises a bicyclic sugar moiety selected from among: cEt, cMOE, LNA, α-LNA, ENA and 2'-thio LNA.

Embodiment 175. The oligomeric compound of any of embodiments 166-168, wherein each B nucleoside comprises a 2'-substituted sugar moiety.

Embodiment 176. The oligomeric compound of embodiment 175, wherein at least one modified central region nucleoside comprises a 2'-substituted sugar moiety comprising a 2' substituent selected from among: halogen, optionally substituted allyl, optionally substituted amino, azido, optionally substituted SH, CN, OCN, $CF_3$, $OCF_3$, O, S, or $N(R_m)$-alkyl; O, S, or $N(R_m)$-alkenyl; O, S or $N(R_m)$-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, $O(CH_2)_2SCH_3$, O—$(CH_2)_2$—O—$N(R_m)(R_n)$ or O—$CH_2$—C(=O)—$N(R_m)(R_n)$, where each $R_m$ and $R_n$ is, independently, H, an amino protecting group or substituted or unsubstituted $C_1$-$C_{10}$ alkyl;
wherein each optionally substituted group is optionally substituted with a substituent group independently selected from among: hydroxyl, amino, alkoxy, carboxy, benzyl, phenyl, nitro ($NO_2$), thiol, thioalkoxy (S-alkyl), halogen, alkyl, aryl, alkenyl and alkynyl.

Embodiment 177. The oligomeric compound of embodiment 175, wherein each B nucleoside comprises a 2'-substituted sugar moiety comprising a 2'-substituent selected from among: a halogen, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2N(CH_3)_2$, $OCH_2C$(=O)—N(H)$CH_3$, $OCH_2C$(=O)—N(H)—$(CH_2)_2$—N$(CH_3)_2$, and $OCH_2$—N(H)—C(=NH)$NH_2$.

Embodiment 178. The oligomeric compound of embodiment 177, wherein each B nucleoside comprises a 2'-substituted sugar moiety comprising a 2'-substituent selected from among: F, $OCH_3$, $O(CH_2)_2$—$OCH_3$.

Embodiment 179. The oligomeric compound of any of embodiments 166-168, wherein each B nucleoside comprises a bicyclic sugar moiety.

Embodiment 180. The oligomeric compound of embodiment 179, wherein each B nucleoside comprises a bicyclic sugar moiety selected from among: cEt, cMOE, LNA, α-LNA, ENA and 2'-thio LNA.

Embodiment 181. The oligomeric compound of any of embodiments 166-180, wherein each A comprises a 2'-substituted sugar moiety comprising a 2'-substituent selected from among: F, $OCH_3$, $O(CH_2)_2$—$OCH_3$, and each B comprises a bicyclic sugar moiety selected from among: LNA and cEt.

Embodiment 182. The oligomeric compound of embodiment 181, wherein each A comprises $O(CH_2)_2$—$OCH_3$ and each B comprises cEt.

Embodiment 183. The oligomeric compound of any of embodiments 166-182, wherein each W nucleoside comprises a 2'-substituted sugar moiety.

Embodiment 184. The oligomeric compound of embodiment 183, wherein at least one central region nucleoside comprises a 2'-substituted sugar moiety comprising a 2' substituent selected from among: halogen, optionally substituted allyl, optionally substituted amino, azido, optionally substituted SH, CN, OCN, $CF_3$, $OCF_3$, O, S, or $N(R_m)$-alkyl; O, S, or $N(R_m)$-alkenyl; O, S or $N(R_m)$-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, $O(CH_2)_2SCH_3$, O—$(CH_2)_2$—O—$N(R_m)(R_n)$ or O—$CH_2$—$C(=O)$—$N(R_m)(R_n)$, where each $R_m$ and $R_n$ is, independently, H, an amino protecting group or substituted or unsubstituted $C_1$-$C_{10}$ alkyl; wherein each optionally substituted group is optionally substituted with a substituent group independently selected from among: hydroxyl, amino, alkoxy, carboxy, benzyl, phenyl, nitro ($NO_2$), thiol, thioalkoxy (S-alkyl), halogen, alkyl, aryl, alkenyl and alkynyl.

Embodiment 185. The oligomeric compound of embodiment 183, wherein each W nucleoside comprises a 2'-substituted sugar moiety comprising a 2'-substituent selected from among: a halogen, $OCH_3$, $OCF_3$, $OCH_2CH_3$, $OCH_2CF_3$, $OCH_2$—$CH=CH_2$, $O(CH_2)$—$OCH_3$, $O(CH_2)_2$—$O(CH_2)_2$—$N(CH_3)_2$, $OCH_2C(=O)$—$N(H)CH_3$, $OCH_2C(=O)$—$N(H)$—$(CH_2)_2$—$N(CH_3)_2$, and $OCH_2$—$N(H)$—$C(=NH)NH_2$.

Embodiment 186. The oligomeric compound of embodiment 185, wherein each W nucleoside comprises a 2'-substituted sugar moiety comprising a 2'-substituent selected from among: F, $OCH_3$, $O(CH_2)_2$—$OCH_3$.

Embodiment 187. The oligomeric compound of any of embodiments 166-182, wherein each W nucleoside comprises a bicyclic sugar moiety.

Embodiment 188. The oligomeric compound of embodiment 187, wherein each W nucleoside comprises a bicyclic sugar moiety selected from among: cEt, cMOE, LNA, α-LNA, ENA and 2'-thio LNA.

Embodiment 189. The oligomeric compound of any of embodiments 166-182, wherein each W comprises a modified nucleobase.

Embodiment 190. The oligomeric compound of embodiment 189, wherein each W comprises a modified nucleobase selected from among a 2-thio pyrimidine and a 5-propyne pyrimidine.

Embodiment 191. The oligomeric compound of embodiment 190, wherein each W comprises 2-thio-thymidine.

Embodiment 192. The oligomeric compound of embodiment 166-182, wherein each W comprises an F-HNA sugar moiety.

Embodiment 193. The oligomeric compound of embodiment 192, wherein each W nucleoside comprises an unmodified 2'-deoxyfuranose sugar moiety.

Embodiment 194. The oligomeric compound of embodiments 1-193, wherein the 5'-region has a motif selected from among: AB, ABB, AAA, BBB, BBBAA, AAB, BAA, BBAA, AABB, AAAB, ABBW, ABBWW, ABBB, ABBBB, ABAB, ABABAB, ABABBB, ABA-BAA, AAABB, AAAABB, AABB, AAAAB, AABBB, ABBBB, BBBBB, AAABW, AAAAA, and BBBBAA;
wherein the 3'-region has a motif selected from among: BBA, AAB, AAA, BBB, BBAA, AABB, WBBA, WAAB, BBBA, BBBBA, BBBB, BBBBBA, ABBBBB, BBAAA, AABBB, BBBAA, BBBBA, BBBBB, BABA, AAAAA, BBAAAA, AABBBB, BAAAA, and ABBBB;
wherein the central region has a nucleoside motif selected from among: DDDDDD, DDDDDDD, DDDDDDDD, DDDDDDDDD, DDDDDDDDD, DXDDDDDDD, DDXDDDDDD, DDDXDDDDD, DDDDXDDDD, DDDDDXDDD, DDDDDDXDD, DDDDDDDXD, DXXDDDDDD, DDDDDDXXD, DDXXDDDDD, DDDXXDDDD, DDDDXXDDD, DDDDDXXDD, DXDDDDDXD, DXDDDDXDD, DXDDDXDDD, DXDDXDDDD, DXDXDDDDD, DDXDDDDXD, DDXDDDXDD, DDXDDXDDD, DDXDXDDDD, DDDXDDDXD, DDDXDDXDD, DDDXDXDDD, DDDDXDDXD, DDDDXDXDD, and DDDDDXDXD, DDDDDDDD, DXDDDDDD, DDXDDDDD, DDDXDDDD, DDDDXDDD, DDDDDXDD, DDDDDDXD, DXDDDDXD, DXDDDXDD, DXDDXDDD, DXDXDDDD, DXXDDDDD, DDXXDDDD, DDXDXDDD, DDXDDXDD, DXDDDDXD, DDDXXDDD, DDDXDXDD, DDDXDDXD, DDDDXXDD, DDDDXDXD, and DDDDDXXD, DXDDDDD, DDXDDDD, DDDXDDD, DDDDXDD, DDDDDXD, DXDDDXD, DXDXDDD, DXXDDDD, DDXXDDD, DDXDXDD, DDXDDXD, DDDXXDD, DDDXDXD, and DDDDXXD, DXDDDD, DDXDDD, DDDXDD, DDDDXD, DXDDDD, DXDXDD, DXDDXD, DDXXDD, DDXDXD, and DDDXXD; and
wherein each A is a modified nucleoside of a first type, each B is a modified nucleoside of a second type, each W is a modified nucleoside of a first type, a second type, or a third type, each D is an unmodified deoxynucleoside, and each X is a modified nucleoside or a modified nucleobase.

Embodiment 195. The oligomeric compound of embodiments 1-203, wherein the 5'-region has a motif selected from among: eeeedk, eeeee, eeeeedk, eeeeeeek, eeeeeeek, eeeeek, eeeek, eeeekk, eeek, eeek, eeekk, eek, eekk, ek, ekek, ekek, ekk, ekkdk, ekkkk, and k;
wherein the 3'-region has a motif selected from among: eee, eeee, eeeee, eeeeee, eeeeeee, eeeeeeee, eeeeeeeee, eeeeeeeeee, eeeekek, eeeekeke, eeek, eeeke, eeekek, eeekeke, eeekekee, eeekk, eeke, eekek, eekeke, eekekee, eekk, kee, keee, keeee, keeeke, keeekee, keek, keeke, keekee, keekeee, keekk, keke, kekee, kke, kkeee, kkeek, and kkke;

wherein the central region has a nucleoside motif selected from among: DDDDDDD, DDDDDDDD, DDDDDDDDD, DXDDDDD, DXDDDDDD, and DXDDDDDDD; and wherein each "e" is a 2'MOE modified nucleoside, each "k" is a cEt modified nucleoside, each "d" is an unmodified deoxynucleoside, and each "X" is a modified nucleoside or a modified nucleobase.

Embodiment 196. The oligomeric compound of embodiment 194, wherein the 5'-region has a motif selected from among:
AB, ABB, AAA, BBB, BBBAA, AAB, BAA, BBAA, AABB, ABBW, ABBWW, ABBB, ABBBB, ABAB, ABABAB, ABABBB, ABABAA, AAABB, AAAABB, AABB, AAAAB, AABBB, ABBBB, BBBBB, AAABW, and BBBBAA; and wherein the 3'-region has a BBA motif.

Embodiment 197. The oligomeric compound of embodiment 194 or 195, wherein one of A or B comprises a bicyclic sugar moiety, another of A or B comprises a 2'-MOE sugar moiety, and W comprises a 2-thio-thymidine nucleobase.

Embodiment 198. The oligomeric compound of embodiment 194 or 195, wherein one of A or B comprises a bicyclic sugar moiety, another of A or B comprises a 2'-MOE sugar moiety, and W comprises FHNA.

Embodiment 199. The oligomeric compound of embodiment 194 or 195, wherein one of A or B comprises cEt, another of A or B comprises a 2'-modified sugar moiety, and W comprises a 2-thio-thymidine nucleobase.

Embodiment 200. The oligomeric compound of embodiment 194 or 195, wherein one of A or B comprises cEt, another of A or B comprises a 2'-modified sugar moiety, and W comprises FHNA.

Embodiment 201. The oligomeric compound of embodiment 194 or 195, wherein each A comprises MOE, each B comprises cEt, and each W is selected from among cEt or FHNA.

Embodiment 202. The oligomeric compound of embodiment 194 or 195, wherein each W comprises cEt.

Embodiment 203. The oligomeric compound of embodiment 194 or 195, wherein each W comprises 2-thio-thymidine.

Embodiment 204. The oligomeric compound of embodiment 194 or 195, wherein each W comprises FHNA.

Embodiment 205. The oligomeric compound of any of embodiments 1-204 comprising at least one modified internucleoside linkage.

Embodiment 206. The oligomeric compound of embodiment 205, wherein each internucleoside linkage is a modified internucleoside linkage.

Embodiment 207. The oligomeric compound of embodiment 205 or 206 comprising at least one phosphorothioate internucleoside linkage.

Embodiment 208. The oligomeric compound of any of embodiments 205 or 206 comprising at least one methylphosphonate internucleoside linkage.

Embodiment 209. The oligomeric compound of any of embodiments 1 to 205, wherein the 5'-most internucleoside linkage is a phosphorothioate internucleoside linkage.

Embodiment 210. The oligomeric compound of any of embodiments 1 to 205 or 209, wherein the 3'-most internucleoside linkage is a phosphorothioate internucleoside linkage.

Embodiment 211. The oligomeric compound of any of embodiments 1 to 205 or 209-210, wherein the 3'-most terminal nucleoside is a phosphodiester internucleoside linkage.

Embodiment 212. The oligomeric compound of any of embodiments 1 to 205 or 209-211, wherein $2^{nd}$ internucleoside linkage from the 5'-end is a phosphodiester internucleoside linkage.

Embodiment 213. The oligomeric compound of any of embodiments 1 to 205 or 209-212, wherein $3^{rd}$ internucleoside linkage from the 5'-end is a phosphodiester internucleoside linkage.

Embodiment 214. The oligomeric compound of any of embodiments 1 to 205 or 209-213, wherein $4^{th}$ internucleoside linkage from the 5'-end is a phosphodiester internucleoside linkage.

Embodiment 215. The oligomeric compound of any of embodiments 1 to 205 or 209-214, wherein $5^{th}$ internucleoside linkage from the 5'-end is a phosphodiester internucleoside linkage.

Embodiment 216. The oligomeric compound of any of embodiments 1 to 205 or 209-215, wherein $6^{th}$ internucleoside linkage from the 5'-end is a phosphodiester internucleoside linkage.

Embodiment 217. The oligomeric compound of any of embodiments 1 to 205 or 209-216, wherein $7^{th}$ internucleoside linkage from the 5'-end is a phosphodiester internucleoside linkage.

Embodiment 218. The oligomeric compound of any of embodiments 1 to 205 or 209-217, wherein $2^{nd}$ internucleoside linkage from the 3'-end is a phosphodiester internucleoside linkage.

Embodiment 219. The oligomeric compound of any of embodiments 1 to 205 or 209-218, wherein $3^{rd}$ internucleoside linkage from the 3'-end is a phosphodiester internucleoside linkage.

Embodiment 220. The oligomeric compound of any of embodiments 1 to 205 or 209-219, wherein $4^{th}$ internucleoside linkage from the 3'-end is a phosphodiester internucleoside linkage.

Embodiment 221. The oligomeric compound of any of embodiments 1 to 205 or 209-220, wherein $5^{th}$ internucleoside linkage from the 3'-end is a phosphodiester internucleoside linkage.

Embodiment 222. The oligomeric compound of any of embodiments 1 to 205 or 209-221, wherein $6^{th}$ internucleoside linkage from the 3'-end is a phosphodiester internucleoside linkage.

Embodiment 223. The oligomeric compound of any of embodiments 1 to 205 or 209-222, wherein $7^{th}$ internucleoside linkage from the 3'-end is a phosphodiester internucleoside linkage.

Embodiment 224. The oligomeric compound of any of embodiments 1 to 205 or 209-223, wherein 5'-most internucleoside linkage of the central region of the sugar motif is a phosphodiester internucleoside linkage.

Embodiment 225. The oligomeric compound of any of embodiments 1 to 205 or 209-224, wherein 3'-most internucleoside linkage of the central region of the sugar motif is a phosphodiester internucleoside linkage.

Embodiment 226. The oligomeric compound of any of embodiments 1 to 205 or 209-225, wherein 5'-most internucleoside linkage of the central region of the sugar motif is a phosphorothioate internucleoside linkage.

Embodiment 227. The oligomeric compound of any of embodiments 1 to 205 or 209-226, wherein 3'-most internucleoside linkage of the central region of the sugar motif is a phosphorothioate internucleoside linkage.

Embodiment 228. The oligomeric compound of any of embodiments 1 to 205 or 209-227, wherein the internucleoside linkage between the 5'-region of the sugar motif and the central region of the sugar motif is a phosphodiester internucleoside linkage.

Embodiment 229. The oligomeric compound of any of embodiments 1 to 205 or 209-228, wherein the internucleoside linkage between the 5'-region of the sugar motif and the central region of the sugar motif is a phosphorothiate internucleoside linkage.

Embodiment 230. The oligomeric compound of any of embodiments 1 to 205 or 209-229, wherein the internucleoside linkage between the 3'-region of the sugar motif and the central region of the sugar motif is a phosphodiester internucleoside linkage.

Embodiment 231. The oligomeric compound of any of embodiments 1 to 205 or 209-230, wherein the internucleoside linkage between the 3'-region of the sugar motif and the central region of the sugar motif is a phosphorothiate internucleoside linkage.

Embodiment 232. The oligomeric compound of any of embodiments 1 to 205 or 209-231, wherein the internucleoside linkage linking a 2'-deoxynucleoside to a modified nucleoside, wherein the linkage is on the 3'-side of the 2'-deoxynucleoside is a phoshodiester internucleoside linkage.

Embodiment 233. The oligomeric compound of any of embodiments 1 to 205 or 209-231, wherein the internucleoside linkage linking a 2'-deoxynucleoside to a modified nucleoside, wherein the linkage is on the 3'-side of the 2'-deoxynucleoside is a phoshorothioate internucleoside linkage.

Embodiment 234. The oligomeric compound of any of embodiments 1 to 205 or 209-231, wherein the internucleoside linkage linking a 2'-deoxynucleoside to a modified nucleoside, wherein the linkage is on the 5'-side of the 2'-deoxynucleoside is a phoshodiester internucleoside linkage.

Embodiment 235. The oligomeric compound of any of embodiments 1 to 205 or 209-231, wherein the internucleoside linkage linking a 2'-deoxynucleoside to a modified nucleoside, wherein the linkage is on the 5'-side of the 2'-deoxynucleoside is a phoshorothioate internucleoside linkage.

Embodiment 236. The oligomeric compound of any of embodiments 1 to 205 or 209-231, wherein each internucleoside linkage that is on the 3'-side of a 2'-deoxynucleoside is a phosphorothioate internucleoside linkage.

Embodiment 237. The oligomeric compound of any of embodiments 1 to 205 or 209-236, wherein each internucleoside linkage within the central region of the sugar motif is a phosphorothioate internucleoside linkage.

Embodiment 238. The oligomeric compound of any of embodiments 1 to 205 or 209-234, wherein the each internucleoside linkage is a phoshorothioate internucleoside linkage.

Embodiment 239. An oligomeric compound having the formula:

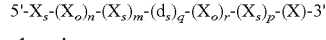

wherein
each X independently comprises a modified nucleoside;
each d comprises a 2'-deoxynucleoside;
each subscript "s" comprises a phosphorothioate internucleoside linkage;
each subscript "o" comprises a phosphodiester internucleoside linkage;
n is an integer from 0 to 4;
m is an integer from 0 to 4;
q is an integer from 5 to 10;
r is an integer from 0 to 4; and
p is an integer from 0 to 5.

Embodiment 240. The oligomeric compound of embodiment 239, wherein m is 0.

Embodiment 241. The oligomeric compound of embodiment 239, wherein m is 1.

Embodiment 242. The oligomeric compound of embodiment 239, wherein m is 1.

Embodiment 243. The oligomeric compound of any of embodiments 239 to 242, wherein n is 0.

Embodiment 244. The oligomeric compound of any of embodiments 239 to 242, wherein n is 1.

Embodiment 245. The oligomeric compound of any of embodiments 239 to 242, wherein n is 2.

Embodiment 246. The oligomeric compound of any of embodiments 239 to 242, wherein n is 3.

Embodiment 247. The oligomeric compound of any of embodiments 239 to 242, wherein n is 4.

Embodiment 248. The oligomeric compound of any of embodiments 239 to 247, wherein q is 5.

Embodiment 249. The oligomeric compound of any of embodiments 239 to 247, wherein q is 6.

Embodiment 250. The oligomeric compound of any of embodiments 239 to 247, wherein q is 7.

Embodiment 251. The oligomeric compound of any of embodiments 239 to 247, wherein q is 8.

Embodiment 252. The oligomeric compound of any of embodiments 239 to 247, wherein q is 9.

Embodiment 253. The oligomeric compound of any of embodiments 239 to 247, wherein q is 10.

Embodiment 254. The oligomeric compound of any of embodiments 239 to 253, wherein r is 0.

Embodiment 255. The oligomeric compound of any of embodiments 239 to 253, wherein r is 1.

Embodiment 256. The oligomeric compound of any of embodiments 239 to 253, wherein r is 2.

Embodiment 257. The oligomeric compound of any of embodiments 239 to 253, wherein r is 3.

Embodiment 258. The oligomeric compound of any of embodiments 239 to 253, wherein r is 4.

Embodiment 259. The oligomeric compound of any of embodiments 239 to 253, wherein p is 1.

Embodiment 260. The oligomeric compound of any of embodiments 239 to 253, wherein p is 2.

Embodiment 261. The oligomeric compound of any of embodiments 239 to 253, wherein p is 3.

Embodiment 262. The oligomeric compound of any of embodiments 239 to 253, wherein p is 4.

Embodiment 263. The oligomeric compound of any of embodiments 239 to 253, wherein p is 5.

Embodiment 264. The oligomeric compound of embodiment 239, wherein at least one modified nucleoside comprises a 2'-substituted sugar moiety comprising a 2' substituent selected from among: halogen, optionally substituted allyl, optionally substituted amino, azido, optionally substituted SH, CN, OCN, $CF_3$, $OCF_3$, O, S, or $N(R_m)$-alkyl; O, S, or $N(R_m)$-alkenyl; O, S or $N(R_m)$-alkynyl;
optionally substituted O-alkylenyl-O-alkyl, optionally substituted alkynyl, optionally substituted alkaryl, optionally substituted aralkyl, optionally substituted O-alkaryl, optionally substituted O-aralkyl, $O(CH_2)_2SCH_3$, $O-(CH_2)_2-O-N(R_m)(R_n)$ or $O-CH_2-C(=O)-N(R_m)(R_n)$, where each $R_m$ and $R_n$ is, independently, H, an amino protecting group or substituted or unsubstituted $C_1$-$C_{10}$ alkyl;

wherein each optionally substituted group is optionally substituted with a substituent group independently selected from among: hydroxyl, amino, alkoxy, carboxy, benzyl, phenyl, nitro ($NO_2$), thiol, thioalkoxy (S-alkyl), halogen, alkyl, aryl, alkenyl and alkynyl.

Embodiment 265. The oligomeric compound of embodiment 240, wherein at least one modified nucleoside comprises a 2'-substituted sugar moiety comprising a 2'-substituent selected from among:
a halogen, $OCH_3$, $OCF_3$, $OCH_2CH_3$, $OCH_2CF_3$, $OCH_2-CH=CH_2$, $O(CH_2)_2-OCH_3$, $O(CH_2)_2-O(CH_2)_2-N(CH_3)_2$, $OCH_2C(=O)-N(H)CH_3$, $OCH_2C(=O)-N(H)-(CH_2)_2-N(CH_3)_2$, and $OCH_2-N(H)-C(=NH)NH_2$.

Embodiment 266. The oligomeric compound of any of embodiments 239 to 265, wherein at least one modified nucleoside comprises a 2'-substituted sugar moiety comprising a 2'-substituent selected from among: F, $OCH_3$, $O(CH_2)_2-OCH_3$.

Embodiment 267. The oligomeric compound of any of embodiments 239 to 265, wherein at least one modified nucleoside comprises a 2'-substituted sugar moiety that comprises an F 2'-substituent.

Embodiment 268. The oligomeric compound of any of embodiments 239 to 265, wherein at least one modified nucleoside comprises a 2'-substituted sugar moiety that comprises an $OCH_3$ 2'-substituent.

Embodiment 269. The oligomeric compound of any of embodiments 239 to 265, wherein at least one of the modified nucleosides comprise a 2'-substituted sugar moiety that comprises an $O(CH_2)_2-OCH_3$ 2'-substituent.

Embodiment 270. The oligomeric compound of any of embodiments 239 to 265, wherein two modified nucleosides comprise an F 2'-substituent.

Embodiment 271. The oligomeric compound of any of embodiments 239 to 265, wherein two modified nucleosides comprise an $OCH_3$ 2'-substituent.

Embodiment 272. The oligomeric compound of any of embodiments 239 to 265, wherein two modified nucleosides comprises an $O(CH_2)_2-OCH_3$ 2'-substituent.

Embodiment 273. The oligomeric compound of any of embodiments 239 to 265, wherein three modified nucleosides comprise an F 2'-substituent.

Embodiment 274. The oligomeric compound of any of embodiments 239 to 265, wherein three modified nucleosides comprise an $OCH_3$ 2'-substituent.

Embodiment 275. The oligomeric compound of any of embodiments 239 to 265, wherein three modified nucleosides comprises an $O(CH_2)_2-OCH_3$ 2'-substituent.

Embodiment 276. The oligomeric compound of any of embodiments 239 to 265, wherein four modified nucleosides comprise an F 2'-substituent.

Embodiment 277. The oligomeric compound of any of embodiments 239 to 265, wherein four modified nucleosides comprise an $OCH_3$ 2'-substituent.

Embodiment 278. The oligomeric compound of any of embodiments 239 to 265, wherein four modified nucleosides comprises an $O(CH_2)_2-OCH_3$ 2'-substituent.

Embodiment 279. The oligomeric compound of any of embodiments 239 to 265, wherein five modified nucleosides comprise an F 2'-substituent.

Embodiment 280. The oligomeric compound of any of embodiments 239 to 265, wherein five modified nucleosides comprise an $OCH_3$ 2'-substituent.

Embodiment 281. The oligomeric compound of any of embodiments 239 to 265, wherein five modified nucleosides comprises an $O(CH_2)_2-OCH_3$ 2'-substituent.

Embodiment 282. The oligomeric compound of any of embodiments 239 to 265, wherein six modified nucleosides comprise an F 2'-substituent.

Embodiment 283. The oligomeric compound of any of embodiments 239 to 265, wherein six modified nucleosides comprise an $OCH_3$ 2'-substituent.

Embodiment 284. The oligomeric compound of any of embodiments 239 to 265, wherein six modified nucleosides comprises an $O(CH_2)_2-OCH_3$ 2'-substituent.

Embodiment 285. The oligomeric compound of any of embodiments 239 to 265, wherein seven modified nucleosides comprise an F 2'-substituent.

Embodiment 286. The oligomeric compound of any of embodiments 239 to 265, wherein seven modified nucleosides comprise an $OCH_3$ 2'-substituent.

Embodiment 287. The oligomeric compound of any of embodiments 239 to 265, wherein seven modified nucleosides comprises an $O(CH_2)_2-OCH_3$ 2'-substituent.

Embodiment 288. The oligomeric compound of any of embodiments 239 to 265, wherein eight modified nucleosides comprise an F 2'-substituent.

Embodiment 289. The oligomeric compound of any of embodiments 239 to 265, wherein eight modified nucleosides comprise an $OCH_3$ 2'-substituent.

Embodiment 290. The oligomeric compound of any of embodiments 239 to 265, wherein eight modified nucleosides comprises an $O(CH_2)_2-OCH_3$ 2'-substituent.

Embodiment 291. The oligomeric compound of any of embodiments 239 to 265, wherein nine modified nucleosides comprise an F 2'-substituent.

Embodiment 292. The oligomeric compound of any of embodiments 239 to 265, wherein nine modified nucleosides comprise an $OCH_3$ 2'-substituent.

Embodiment 293. The oligomeric compound of any of embodiments 239 to 265, wherein nine modified nucleosides comprises an $O(CH_2)_2-OCH_3$ 2'-substituent.

Embodiment 294. The oligomeric compound of any of embodiments 239 to 265, wherein ten modified nucleosides comprise an F 2'-substituent.

Embodiment 295. The oligomeric compound of any of embodiments 239 to 265, wherein ten modified nucleosides comprise an $OCH_3$ 2'-substituent.

Embodiment 296. The oligomeric compound of any of embodiments 239 to 265, wherein ten modified nucleosides comprises an $O(CH_2)_2-OCH_3$ 2'-substituent.

Embodiment 297. The oligomeric compound of any of embodiments 239 to 296, wherein at least one modified nucleoside comprises a bicyclic sugar moiety selected from among: cEt, cMOE, LNA, α-LNA, ENA and 2'-thio LNA.

Embodiment 298. The oligomeric compound of any of embodiments 239 to 296, wherein at least two modified nucleosides comprise a bicyclic sugar moiety selected from among: cEt, cMOE, LNA, α-LNA, ENA and 2'-thio LNA.

Embodiment 299. The oligomeric compound of any of embodiments 239 to 296, wherein at least three modified nucleosides comprise a bicyclic sugar moiety selected from among: cEt, cMOE, LNA, α-LNA, ENA and 2'-thio LNA.

Embodiment 300. The oligomeric compound of any of embodiments 239 to 296, wherein at least four modified nucleosides comprise a bicyclic sugar moiety selected from among: cEt, cMOE, LNA, α-LNA, ENA and 2'-thio LNA.

Embodiment 301. The oligomeric compound of any of embodiments 239 to 296, wherein at least five modified nucleosides comprise a bicyclic sugar moiety selected from among: cEt, cMOE, LNA, α-LNA, ENA and 2'-thio LNA.

Embodiment 302. The oligomeric compound of any of embodiments 239 to 296, wherein at least six modified nucleosides comprise a bicyclic sugar moiety selected from among: cEt, cMOE, LNA, α-LNA, ENA and 2'-thio LNA.

Embodiment 303. The oligomeric compound of any of embodiments 239 to 296, wherein at least seven modified nucleosides comprise a bicyclic sugar moiety selected from among: cEt, cMOE, LNA, α-LNA, ENA and 2'-thio LNA.

Embodiment 304. The oligomeric compound of any of embodiments 239 to 296, wherein at least eight modified nucleosides comprise a bicyclic sugar moiety selected from among: cEt, cMOE, LNA, α-LNA, ENA and 2'-thio LNA.

Embodiment 305. The oligomeric compound of any of embodiments 239 to 296, wherein at least nine modified nucleosides comprise a bicyclic sugar moiety selected from among: cEt, cMOE, LNA, α-LNA, ENA and 2'-thio LNA.

Embodiment 306. The oligomeric compound of any of embodiments 239 to 296, wherein at least ten modified nucleosides comprise a bicyclic sugar moiety selected from among: cEt, cMOE, LNA, α-LNA, ENA and 2'-thio LNA.

Embodiment 307. The oligomeric compound of any of embodiments 239 to 296, wherein at least one modified nucleoside comprises a cEt bicyclic sugar moiety.

Embodiment 308. The oligomeric compound of any of embodiments 239 to 296, wherein at least two modified nucleosides comprise a cEt bicyclic sugar moiety.

Embodiment 309. The oligomeric compound of any of embodiments 239 to 296, wherein at least three modified nucleosides comprise a cEt bicyclic sugar moiety.

Embodiment 310. The oligomeric compound of any of embodiments 239 to 296, wherein at least four modified nucleosides comprise a cEt bicyclic sugar moiety.

Embodiment 311. The oligomeric compound of any of embodiments 239 to 296, wherein at least five modified nucleosides comprise a cEt bicyclic sugar moiety.

Embodiment 312. The oligomeric compound of any of embodiments 239 to 296, wherein at least six modified nucleosides comprise a cEt bicyclic sugar moiety.

Embodiment 313. The oligomeric compound of any of embodiments 239 to 296, wherein at least seven modified nucleosides comprise a cEt bicyclic sugar moiety.

Embodiment 314. The oligomeric compound of any of embodiments 239 to 296, wherein at least eight modified nucleosides comprise a cEt bicyclic sugar moiety.

Embodiment 315. The oligomeric compound of any of embodiments 239 to 296, wherein at least nine modified nucleosides comprise a cEt bicyclic sugar moiety.

Embodiment 316. The oligomeric compound of any of embodiments 239 to 296, wherein at least ten modified nucleosides comprise a cEt bicyclic sugar moiety.

Embodiment 317. The oligomeric compound of any of embodiments 239 to 296, wherein at least one modified nucleoside comprises an LNA bicyclic sugar moiety.

Embodiment 318. The oligomeric compound of any of embodiments 239 to 296, wherein at least two modified nucleosides comprise an LNA bicyclic sugar moiety.

Embodiment 319. The oligomeric compound of any of embodiments 239 to 296, wherein at least three modified nucleosides comprise an LNA bicyclic sugar moiety.

Embodiment 320. The oligomeric compound of any of embodiments 239 to 296, wherein at least four modified nucleosides comprise an LNA bicyclic sugar moiety.

Embodiment 321. The oligomeric compound of any of embodiments 239 to 296, wherein at least five modified nucleosides comprise an LNA bicyclic sugar moiety.

Embodiment 322. The oligomeric compound of any of embodiments 239 to 296, wherein at least six modified nucleosides comprise an LNA bicyclic sugar moiety.

Embodiment 323. The oligomeric compound of any of embodiments 239 to 296, wherein at least seven modified nucleosides comprise an LNA bicyclic sugar moiety.

Embodiment 324. The oligomeric compound of any of embodiments 239 to 296, wherein at least eight modified nucleosides comprise an LNA bicyclic sugar moiety.

Embodiment 325. The oligomeric compound of any of embodiments 239 to 296, wherein at least nine modified nucleosides comprise an LNA bicyclic sugar moiety.

Embodiment 326. The oligomeric compound of any of embodiments 239 to 296, wherein at least ten modified nucleosides comprise an LNA bicyclic sugar moiety.

Embodiment 327. The oligomeric compound of any of embodiments 239 to 263, wherein each modified nucleoside comprises a 2'-substituted sugar moiety comprising a 2' substituent selected from among: halogen, optionally substituted allyl, optionally substituted amino, azido, optionally substituted SH, CN, OCN, $CF_3$, $OCF_3$, O, S, or $N(R_m)$-alkyl; O, S, or $N(R_m)$-alkenyl; O, S or $N(R_m)$-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, $O(CH_2)_2SCH_3$, $O-(CH_2)_2-O-N(R_m)(R_n)$ or $O-CH_2-C(=O)-N(R_m)(R_n)$, where each $R_m$ and $R_n$ is, independently, H, an amino protecting group or substituted or unsubstituted $C_1$-$C_{10}$ alkyl;
wherein each optionally substituted group is optionally substituted with a substituent group independently selected from among: hydroxyl, amino, alkoxy, carboxy, benzyl, phenyl, nitro ($NO_2$), thiol, thioalkoxy (S-alkyl), halogen, alkyl, aryl, alkenyl and alkynyl.

Embodiment 328. The oligomeric compound of any of embodiments 239 to 263, wherein each modified nucleoside comprises a 2'-substituted sugar moiety comprising a 2'-substituent selected from among: a halogen, $OCH_3$, $OCF_3$, $OCH_2CH_3$, $OCH_2CF_3$, $OCH_2$—$CH$=$CH_2$, $O(CH_2)_2$—$OCH_3$, $O(CH_2)_2$—$O(CH_2)_2$—$N(CH_3)_2$, $OCH_2C$(=O)—$N(H)CH_3$, $OCH_2C$(=O)—$N(H)$—$(CH_2)_2$—$N(CH_3)_2$, and $OCH_2$—$N(H)$—$C$(=$NH$)$NH_2$.

Embodiment 329. The oligomeric compound of any of embodiments 239 to 263, wherein each modified nucleoside comprises a 2'-substituted sugar moiety comprising a 2'-substituent selected from among: F, $OCH_3$, $O(CH_2)_2$—$OCH_3$.

Embodiment 330. The oligomeric compound of any of embodiments 239 to 263, wherein each modified nucleoside comprises a 2'-substituted sugar moiety comprises an F 2'-substituent.

Embodiment 331. The oligomeric compound of any of embodiments 239 to 263, wherein each modified nucleoside comprises a 2'-substituted sugar moiety comprises an $OCH_3$ 2'-substituent.

Embodiment 332. The oligomeric compound of any of embodiments 239 to 263, wherein each modified nucleoside comprises a 2'-substituted sugar moiety comprises an $O(CH_2)_2$—$OCH_3$ 2'-substituent.

Embodiment 333. The oligomeric compound of any of embodiments 239 to 263, wherein each modified nucleoside comprises a bicyclic sugar moiety.

Embodiment 334. The oligomeric compound of any of embodiments 239 to 263, wherein each modified nucleoside comprises a bicyclic sugar moiety.

Embodiment 335. The oligomeric compound of any of embodiments 239 to 263, wherein each modified nucleoside comprises a bicyclic sugar moiety selected from among: cEt, cMOE, LNA, α-LNA, ENA and 2'-thio LNA.

Embodiment 336. The oligomeric compound of any of embodiments 239 to 263, wherein each modified nucleoside comprises a bicyclic sugar moiety selected from among: cEt, cMOE, LNA, α-LNA, ENA and 2'-thio LNA.

Embodiment 337. The oligomeric compound of any of embodiments 1 to 336, wherein the oligomeric compound does not target a nucleic acid transcript that encodes Huntington.

Embodiment 338. The oligomeric compound of any of embodiments 1 to 336, wherein the oligomeric compound does not target a nucleic acid transcript that encodes SOD1.

Embodiment 339. The oligomeric compound of any of embodiments 1 to 336, wherein the oligomeric compound does not target a nucleic acid transcript that encodes Nav 1.7.

Embodiment 340. The oligomeric compound of any of embodiments 1 to 336, wherein the oligomeric compound does not target a nucleic acid transcript that encodes alpha synuclein.

Embodiment 341. A method of reducing the acute toxicity of an oligomeric compound comprising, introducing one or more phosphodiester internucleoside linkages into the acutely toxic oligomeric compound.

Embodiment 342. A method of reducing the acute toxicity of an oligomeric compound comprising, reducing the number of 2'-deoxynucleosides in the gap region of the acutely toxic oligomeric compound.

Embodiment 343. A method of reducing the acute toxicity of an oligomeric compound comprising, introducing one or more phosphodiester internucleoside linkages into the acutely toxic oligomeric compound and reducing the number of 2'-deoxynucleosides in the gap region of the acutely toxic oligomeric compound.

Embodiment 344. A method of reducing the acute toxicity of an oligomeric compound delivered to the CNS comprising, introducing one or more phosphodiester internucleoside linkages into the acutely toxic oligomeric compound.

Embodiment 345. A method of reducing the acute toxicity of an oligomeric compound delivered to the CNS comprising, reducing the number of 2'-deoxynucleosides in the gap region of the acutely toxic oligomeric compound.

Embodiment 346. A method of reducing the acute toxicity of an oligomeric compound delivered to the CNS comprising, introducing one or more phosphodiester internucleoside linkages into the acutely toxic oligomeric compound and reducing the number of 2'-deoxynucleosides in the gap region of the acutely toxic oligomeric compound.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "2'-F nucleoside" refers to a nucleoside comprising a sugar comprising fluoroine at the 2' position. Unless otherwise indicated, the fluorine in a 2'-F nucleoside is in the ribo position (replacing the OH of a natural ribose).

As used herein, "2'-(ara)-F" refers to a 2'-F substituted nucleoside, wherein the fluoro group is in the arabino position.

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligomeric compound which is capable of hybridizing to a complementary oligomeric compound. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2'bridge.

As used herein, "locked nucleic acid nucleoside" or "LNA" means a nucleoside comprising a bicyclic sugar moiety comprising a 4'-CH$_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "RNA-like nucleoside" means a modified nucleoside that adopts a northern configuration and functions like RNA when incorporated into an oligonucleotide. RNA-like nucleosides include, but are not limited to 3'-endo furanosyl nucleosides and RNA surrogates.

As used herein, "3'-endo-furanosyl nucleoside" means an RNA-like nucleoside that comprises a substituted sugar moiety that has a 3'-endo conformation. 3'-endo-furanosyl nucleosides include, but are not limited to: 2'-MOE, 2'-F, 2'-OMe, LNA, ENA, and cEt nucleosides.

As used herein, "RNA-surrogate nucleoside" means an RNA-like nucleoside that does not comprise a furanosyl. RNA-surrogate nucleosides include, but are not limited to hexitols and cyclopentanes.

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means a measurable activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound is intended to hybridize.

As used herein, "non-target nucleic acid" means a nucleic acid molecule to which hybridization of an antisense compound is not intended or desired. In certain embodiments, antisense compounds do hybridize to a non-target, due to homology between the target (intended) and non-target (un-intended).

As used herein, "mRNA" means an RNA molecule that encodes a protein.

As used herein, "pre-mRNA" means an RNA transcript that has not been fully processed into mRNA. Pre-RNA includes one or more intron.

As used herein, "object RNA" means an RNA molecule other than a target RNA, the amount, activity, splicing, and/or function of which is modulated, either directly or indirectly, by a target nucleic acid. In certain embodiments, a target nucleic acid modulates splicing of an object RNA. In certain such embodiments, an antisense compound modulates the amount or activity of the target nucleic acid, resulting in a change in the splicing of an object RNA and ultimately resulting in a change in the activity or function of the object RNA.

As used herein, "microRNA" means a naturally occurring, small, non-coding RNA that represses gene expression of at least one mRNA. In certain embodiments, a microRNA represses gene expression by binding to a target site within a 3' untranslated region of an mRNA. In certain embodiments, a microRNA has a nucleobase sequence as set forth in miRBase, a database of published microRNA sequences found at microrna.sanger.ac.uk/sequences/. In certain embodiments, a microRNA has a nucleobase sequence as set forth in miRBase version 12.0 released September 2008, which is herein incorporated by reference in its entirety.

As used herein, "microRNA mimic" means an oligomeric compound having a sequence that is at least partially identical to that of a microRNA. In certain embodiments, a microRNA mimic comprises the microRNA seed region of a microRNA. In certain embodiments, a microRNA mimic modulates translation of more than one target nucleic acids. In certain embodiments, a microRNA mimic is double-stranded.

As used herein, "differentiating nucleobase" means a nucleobase that differs between two nucleic acids. In certain instances, a target region of a target nucleic acid differs by 1-4 nucleobases from a non-target nucleic acid. Each of those differences is referred to as a differentiating nucleobase. In certain instances, a differentiating nucleobase is a single-nucleotide polymorphism.

As used herein, "target-selective nucleoside" means a nucleoside of an antisense compound that corresponds to a differentiating nucleobase of a target nucleic acid.

As used herein, "allele" means one of a pair of copies of a gene existing at a particular locus or marker on a specific chromosome, or one member of a pair of nucleobases existing at a particular locus or marker on a specific chromosome, or one member of a pair of nucleobase sequences existing at a particular locus or marker on a specific chromosome. For a diploid organism or cell or for autosomal chromosomes, each allelic pair will normally occupy corresponding positions (loci) on a pair of homologous chromosomes, one inherited from the mother and one inherited from the father. If these alleles are identical, the organism or cell is said to be "homozygous" for that allele; if they differ, the organism or cell is said to be "heterozygous" for that allele. "Wild-type allele" refers to the genotype typically not associated with disease or dysfunction of the gene product. "Mutant allele" refers to the genotype associated with disease or dysfunction of the gene product.

As used herein, "allelic variant" means a particular identity of an allele, where more than one identity occurs. For example, an allelic variant may refer to either the mutant allele or the wild-type allele.

As used herein, "single nucleotide polymorphism" or "SNP" means a single nucleotide variation between the genomes of individuals of the same species. In some cases, a SNP may be a single nucleotide deletion or insertion. In general, SNPs occur relatively frequently in genomes and thus contribute to genetic diversity. The location of a SNP is generally flanked by highly conserved sequences. An individual may be homozygous or heterozygous for an allele at each SNP site.

As used herein, "single nucleotide polymorphism site" or "SNP site" refers to the nucleotides surrounding a SNP contained in a target nucleic acid to which an antisense compound is targeted.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "modification motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)R$_{aa}$), carboxyl (—C(O)O—R$_{aa}$), aliphatic groups, alicyclic groups, alkoxy, substituted oxy (—O—R$_{aa}$), aryl, aralkyl, heterocyclic radical, heteroaryl, heteroarylalkyl, amino (—N(R$_{bb}$)(R$_{cc}$)), imino(=NR$_{bb}$), amido (—C(O)N(R$_{bb}$)(R$_{cc}$) or —N(R$_{bb}$)C(O)R$_{aa}$), azido (—N$_3$), nitro (—NO$_2$), cyano (—CN), carbamido (—OC(O)N(R$_{bb}$)(R$_{cc}$) or —N(R$_{bb}$)C(O)OR$_{aa}$), ureido (—N(R$_{bb}$)C(O)N(R$_{bb}$)(R$_{cc}$)), thioureido (—N(R$_{bb}$)C(S)N(R$_{bb}$)—(R$_{cc}$)), guanidinyl (—N(R$_{bb}$)C(=NR$_{bb}$)N(R$_{bb}$)(R$_{cc}$)), amidinyl (—C(=NR$_{bb}$)N(R$_{bb}$)(R$_{cc}$) or —N(R$_{bb}$)C(=NR$_{bb}$)(R$_{aa}$)), thiol (—SR$_{bb}$), sulfinyl (—S(O)R$_{bb}$), sulfonyl (—S(O)$_2$R$_{bb}$) and sulfonamidyl (—S(O)$_2$N(R$_{bb}$)(R$_{cc}$) or —N(R$_{bb}$)S—(O)$_2$R$_{bb}$). Wherein each R$_{aa}$, R$_{bb}$ and R$_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein, "Intracerebroventricular" or "ICV" means administration into the ventricular system of the brain.

A. Oligomeric Compounds

In certain embodiments, the present invention provides oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications. Such chemical modifications include modifications of one or more nucleoside (including modifications to the sugar moiety and/or the nucleobase) and/or modifications to one or more internucleoside linkage.

a. Certain Modified Nucleosides

In certain embodiments, provided herein are oligomeric compounds comprising or consisting of oligonucleotides comprising at least one modified nucleoside. Such modified nucleosides comprise a modified sugar moeity, a modified nucleobase, or both a modified sugar moiety and a modified nucleobase.

i. Certain Sugar Moieties

In certain embodiments, oligomeric compounds of the invention comprise one or more modified nucleosides comprising a modified sugar moiety. Such oligomeric compounds comprising one or more sugar-modified nucleosides may have desirable properties, such as enhanced nuclease stability or increased binding affinity with a target nucleic acid relative to oligomeric compounds comprising only nucleosides comprising naturally occurring sugar moieties. In certain embodiments, modified sugar moieties are substituted sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; O—C$_1$-C$_{10}$ alkoxy; O—C$_1$-C$_{10}$ substituted alkoxy, OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, O—C$_1$-C$_{10}$ alkoxy; O—C$_1$-C$_{10}$ substituted alkoxy, SH, CN, OCN, CF$_3$, OCF$_3$, O-alkyl, S-alkyl, N(R$_m$)-alkyl; O-alkenyl, S-alkenyl, or N(R$_m$)-alkenyl; O-alkynyl, S-alkynyl, N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, —CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$ SCH$_3$, O—(CH$_2$)$_2$—O—N(CH$_3$)$_2$, —O(CH$_2$)$_2$O (CH$_2$)$_2$N(CH$_3$)$_2$, and O—CH$_2$—C(=O)—N(H)CH$_3$.

In certain embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2',4'-(CH$_2$)$_2$-2', 4'-(CH$_2$)$_3$-2', 4'-(CH$_2$)—O-2' (LNA); 4'-(CH$_2$)—S-2'; 4'-(CH$_2$)$_2$—O-2' (ENA); 4'-CH(CH$_3$)—O-2' (cEt) and 4'-CH(CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)—2' (see, e.g., Chattopadhyaya, et al., *J. Org. Chem.*, 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH$_2$—O-2') BNA, (B) β-D-Methyleneoxy (4'-CH$_2$—O-2') BNA (also referred to as locked nucleic acid or LNA), (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH2-N(R)-2') BNA, (I) methyl carbocyclic (4'-CH$_2$—CH(CH$_3$)-2') BNA, (J) propylene carbocyclic (4'-(CH$_2$)$_3$-2') BNA, and (M) 4'-CH$_2$—O—CH$_2$-2' as depicted below.

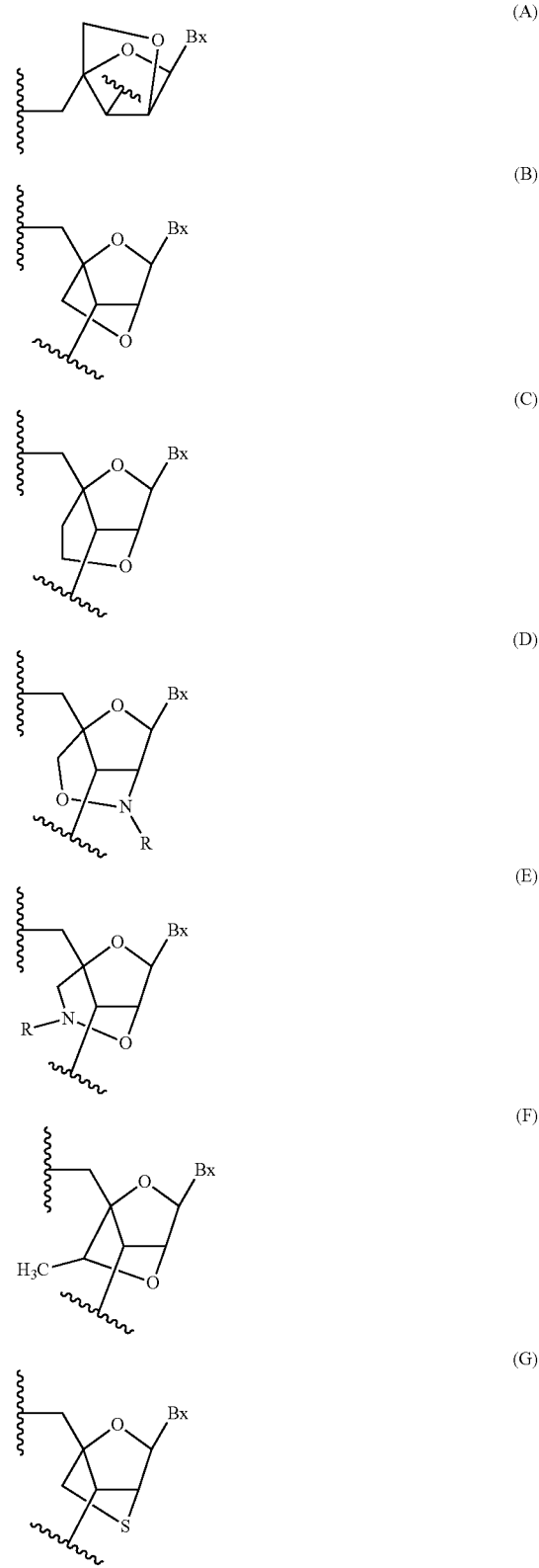

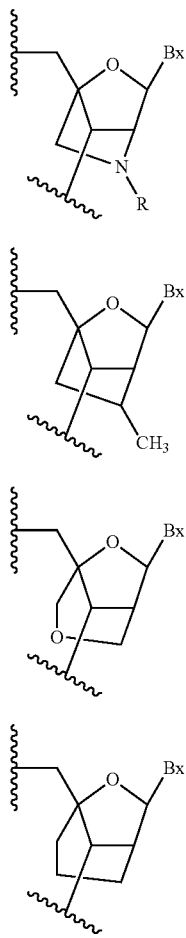

(H)

(I)

(M)

(J)

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., *Nucleic Acids Research*, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfer, carbon or nitrogen atom. In certain such embodiments, such modified sugar moiety also comprises bridging and/or non-bridging substituents as described above. For example, certain sugar surrogates comprise a 4'-sulfer atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research*, 1997, 25(22), 4429-4443 and Albaek et al., *J. Org. Chem.*, 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VII:

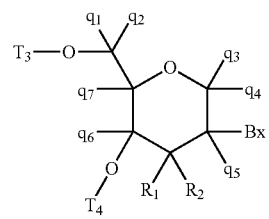

VII wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, OC(=X)$J_1$, OC(=X)$NJ_1J_2$, $NJ_3$C(=X) $NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclic and tricyclic sugar and sugar surrogate ring systems are known in the art that can be used to modify nucleosides (see, e.g., review article: Leumann, J. C, *Bioorganic & Medicinal Chemistry*, 2002, 10, 841-854).

In certain embodiments, sugar surrogates comprise rings having more than 5 atoms and more than one heteroatom. For example nucleosides comprising morpholino sugar moieties and their use in oligomeric compounds has been reported (see for example: Braasch et al., Biochemistry, 2002, 41, 4503-4510; and U.S. Pat. Nos. 5,698,685; 5,166, 315; 5,185,444; and 5,034,506). As used here, the term "morpholino" means a sugar surrogate having the following structure:

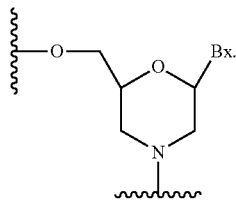

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 Published on Aug. 21, 08 for other disclosed 5', 2'-bis substituted nucleosides) and replacement of the ribosyl ring oxygen atom with S and further substitution at the $2^1$-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

ii. Certain Modified Nucleobases

In certain embodiments, nucleosides of the present invention comprise one or more unmodified nucleobases. In certain embodiments, nucleosides of the present invention comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine ([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134, 066; 5,175,273; 5,367,066; 5,432,272; 5,457,187; 5,459, 255; 5,484,908; 5,502,177; 5,525,711; 5,552,540; 5,587, 469; 5,594,121; 5,596,091; 5,614,617; 5,645,985; 5,681, 941; 5,750,692; 5,763,588; 5,830,653 and 6,005,096, certain of which are commonly owned with the instant application, and each of which is herein incorporated by reference in its entirety.

b. Certain Internucleoside Linkages

In certain embodiments, nucleosides may be linked together using any internucleoside linkage to form oligonucleotides. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

i. 3'-Endo Modifications

In one aspect of the present disclosure, oligomeric compounds include nucleosides synthetically modified to induce a 3'-endo sugar conformation. A nucleoside can incorporate synthetic modifications of the heterocyclic base moiety, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference for an RNA type duplex (A form helix, predominantly 3'-endo) as a requirement of RNA interference which is supported in part by the fact that duplexes composed of 2'-deoxy-2'-F-nucleosides appear efficient in triggering RNAi response in the *C. elegans* system. Properties that are enhanced by using more stable 3'-endo nucleosides include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric compounds having one or more nucleosides modified in such a way as to favor a C3'-endo type conformation.

Scheme 1

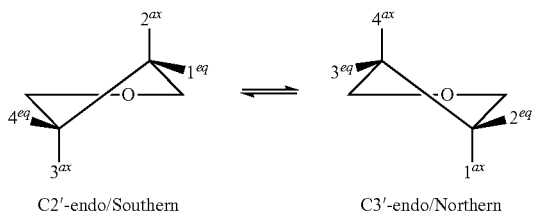

C2'-endo/Southern    C3'-endo/Northern

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element, as exemplified in Example 35, below (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Some modifications actually lock the conformational geometry by formation of a bicyclic sugar moiety e.g. locked nucleic acid (LNA, Singh et al, Chem. Commun. (1998), 4, 455-456), and ethylene bridged nucleic acids (ENA, Morita et al, Bioorganic & Medicinal Chemistry Letters (2002), 12, 73-76.)

c. Certain Motifs

In certain embodiments, oligomeric compounds comprise or consist of oligonucleotides. In certain embodiments, such oligonucleotides comprise one or more chemical modification. In certain embodiments, chemically modified oligonucleotides comprise one or more modified sugars. In certain embodiments, chemically modified oligonucleotides comprise one or more modified nucleobases. In certain embodiments, chemically modified oligonucleotides comprise one or more modified internucleoside linkages. In certain embodiments, the chemical modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

i. Certain Sugar Motifs

In certain embodiments, oligonucleotides comprise one or more type of modified sugar moieties and/or naturally occurring sugar moieties arranged along an oligonucleotide or region thereof in a defined pattern or sugar motif. Such sugar motifs include but are not limited to any of the sugar modifications discussed herein.

In certain embodiments, the oligonucleotides comprise or consist of a region having a gapmer sugar motif, which comprises two external regions or "wings" and a central or internal region or "gap." The three regions of a gapmer sugar motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric sugar gapmer). In certain embodiments, the sugar motifs of the 5'-wing differs from the sugar motif of the 3'-wing (asymmetric sugar gapmer).

ii. Certain Nucleobase Modification Motifs

In certain embodiments, oligonucleotides comprise chemical modifications to nucleobases arranged along the oligonucleotide or region thereof in a defined pattern or nucleobases modification motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, oligonucleotides comprise one or more nucleosides comprising a modified nucleobase. In certain embodiments, oligonucleotides having a gapmer sugar motif comprise a nucleoside comprising a modified nucleobase. In certain such embodiments, one nucleoside comprising a modified nucleobases is in the central gap of an oligonucleotide having a gapmer sugar motif. In certain embodiments, the sugar is an unmodified 2'deoxynucleoside. In certain embodiments, the modified nucleobase is selected from: a 2-thio pyrimidine and a 5-propyne pyrimidine In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

iii. Certain Nucleoside Motifs

In certain embodiments, oligonucleotides comprise nucleosides comprising modified sugar moieties and/or nucleosides comprising modified nucleobases. Such motifs can be described by their sugar motif and their nucleobase motif separately or by their nucleoside motif, which provides positions or patterns of modified nucleosides (whether modified sugar, nucleobase, or both sugar and nucleobase) in an oligonucleotide.

In certain embodiments, the oligonucleotides comprise or consist of a region having a gapmer nucleoside motif, which comprises two external regions or "wings" and a central or internal region or "gap." The three regions of a gapmer nucleoside motif (the 5'-wing, the gap, and the 3'-wing) form a contiguous sequence of nucleosides wherein at least some of the sugar moieties and/or nucleobases of the nucleosides of each of the wings differ from at least some of the sugar moieties and/or nucleobase of the nucleosides of the gap. Specifically, at least the nucleosides of each wing that are closest to the gap (the 3'-most nucleoside of the 5'-wing and the 5'-most nucleoside of the 3'-wing) differ from the neighboring gap nucleosides, thus defining the boundary between the wings and the gap. In certain embodiments, the nucleosides within the gap are the same as one another. In certain embodiments, the gap includes one or more nucleoside that differs from one or more other nucleosides of the gap. In certain embodiments, the nucleoside motifs of the two wings are the same as one another (symmetric gapmer). In certain embodiments, the nucleoside motifs of the 5'-wing differs from the nucleoside motif of the 3'-wing (asymmetric gapmer).

iv. Certain 5'-wings

In certain embodiments, the 5'-wing of a gapmer consists of 1 to 6 linked nucleosides. In certain embodiments, the 5'-wing of a gapmer consists of 1 to 5 linked nucleosides. In certain embodiments, the 5'-wing of a gapmer consists of 2 to 5 linked nucleosides. In certain embodiments, the 5'-wing of a gapmer consists of 3 to 5 linked nucleosides. In certain embodiments, the 5'-wing of a gapmer consists of 4 or 5 linked nucleosides. In certain embodiments, the 5'-wing of a gapmer consists of 1 to 4 linked nucleosides. In certain embodiments, the 5'-wing of a gapmer consists of 1 to 3 linked nucleosides. In certain embodiments, the 5'-wing of a gapmer consists of 1 or 2 linked nucleosides. In certain embodiments, the 5'-wing of a gapmer consists of 2 to 4 linked nucleosides. In certain embodiments, the 5'-wing of a gapmer consists of 2 or 3 linked nucleosides. In certain embodiments, the 5'-wing of a gapmer consists of 3 or 4 linked nucleosides. In certain embodiments, the 5'-wing of a gapmer consists of 1 nucleoside. In certain embodiments, the 5'-wing of a gapmer consists of 2 linked nucleosides. In certain embodiments, the 5'-wing of a gapmer consists of 3 linked nucleosides. In certain embodiments, the 5'-wing of a gapmer consists of 4 linked nucleosides. In certain embodiments, the 5'-wing of a gapmer consists of 5 linked nucleosides. In certain embodiments, the 5'-wing of a gapmer consists of 6 linked nucleosides.

In certain embodiments, the 5'-wing of a gapmer comprises at least one bicyclic nucleoside. In certain embodiments, the 5'-wing of a gapmer comprises at least two bicyclic nucleosides. In certain embodiments, the 5'-wing of a gapmer comprises at least three bicyclic nucleosides. In certain embodiments, the 5'-wing of a gapmer comprises at least four bicyclic nucleosides. In certain embodiments, the 5'-wing of a gapmer comprises at least one constrained ethyl nucleoside. In certain embodiments, the 5'-wing of a gapmer comprises at least one LNA nucleoside. In certain embodiments, each nucleoside of the 5'-wing of a gapmer is a bicyclic nucleoside. In certain embodiments, each nucleoside of the 5'-wing of a gapmer is a constrained ethyl nucleoside. In certain embodiments, each nucleoside of the 5'-wing of a gapmer is a LNA nucleoside.

In certain embodiments, the 5'-wing of a gapmer comprises at least one non-bicyclic modified nucleoside. In certain embodiments, the 5'-wing of a gapmer comprises at least one 2'-substituted nucleoside. In certain embodiments, the 5'-wing of a gapmer comprises at least one 2'-MOE nucleoside. In certain embodiments, the 5'-wing of a gapmer comprises at least one 2'-OMe nucleoside. In certain embodiments, each nucleoside of the 5'-wing of a gapmer is a non-bicyclic modified nucleoside. In certain embodiments, each nucleoside of the 5'-wing of a gapmer is a 2'-substituted nucleoside. In certain embodiments, each nucleoside of the 5'-wing of a gapmer is a 2'-MOE nucleoside. In certain embodiments, each nucleoside of the 5'-wing of a gapmer is a 2'-OMe nucleoside.

In certain embodiments, the 5'-wing of a gapmer comprises at least one 2'-deoxynucleoside. In certain embodiments, each nucleoside of the 5'-wing of a gapmer is a 2'-deoxynucleoside. In a certain embodiments, the 5'-wing of a gapmer comprises at least one ribonucleoside. In certain embodiments, each nucleoside of the 5'-wing of a gapmer is a ribonucleoside. In certain embodiments, one, more than one, or each of the nucleosides of the 5'-wing is an RNA-like nucleoside.

In certain embodiments, the 5'-wing of a gapmer comprises at least one bicyclic nucleoside and at least one non-bicyclic modified nucleoside. In certain embodiments, the 5'-wing of a gapmer comprises at least one bicyclic nucleoside and at least one 2'-substituted nucleoside. In certain embodiments, the 5'-wing of a gapmer comprises at least one bicyclic nucleoside and at least one 2'-MOE nucleoside. In certain embodiments, the 5'-wing of a gapmer comprises at least one bicyclic nucleoside and at least one 2'-OMe nucleoside. In certain embodiments, the 5'-wing of a gapmer comprises at least one bicyclic nucleoside and at least one 2'-deoxynucleoside.

In certain embodiments, the 5'-wing of a gapmer comprises at least one constrained ethyl nucleoside and at least one non-bicyclic modified nucleoside. In certain embodiments, the 5'-wing of a gapmer comprises at least one constrained ethyl nucleoside and at least one 2'-substituted nucleoside. In certain embodiments, the 5'-wing of a gapmer comprises at least one constrained ethyl nucleoside and at least one 2'-MOE nucleoside. In certain embodiments, the 5'-wing of a gapmer comprises at least one constrained ethyl nucleoside and at least one 2'-OMe nucleoside. In certain embodiments, the 5'-wing of a gapmer comprises at least one constrained ethyl nucleoside and at least one 2'-deoxynucleoside.

In certain embodiments, the 5'-wing of a gapmer has a nucleoside motif selected from among the following: ADDA; ABDAA; ABBA; ABB; ABAA; AABAA; AAABAA; AAAABAA; AAAAABAA; AAABAA; AABAA; ABAB; ABADB; ABADDB; AAABB; AAAAA; ABBDC; ABDDC; ABBDCC; ABBDDC; ABBDCC; ABBC; AA; AAA; AAAA; AAAAB; AAAAAAA; AAAAAAAA; ABBB; AB; ABAB; AAAAB; AABBB; AAAAB; and AABBB, wherein each A is a modified nucleoside of a first type, each B is a modified nucleoside of a second type, each C is a modified nucleoside of a third type, and each D is an unmodified deoxynucleoside.

In certain embodiments, the 5'-wing of a gapmer has a nucleoside motif selected from among the following: AB, ABB, AAA, BBB, BBBAA, AAB, BAA, BBAA, AABB, AAAB, ABBW, ABBWW, ABBB, ABBBB, ABAB, ABABAB, ABABBB, ABABAA, AAABB, AAAABB, AABB, AAAAB, AABBB, ABBBB, BBBBB, AAABW, AAAAA, BBBBAA, and AAABW; wherein each A is a modified nucleoside of a first type, each B is a modified nucleoside of a second type, and each W is a modified nucleoside of either the first type, the second type or a third type.

In certain embodiments, the 5'-wing of a gapmer has a nucleoside motif selected from among the following: ABB; ABAA; AABAA; AAABAA; ABAB; ABADB; AAABB; AAAAA; AA; AAA; AAAA; AAAAB; ABBB; AB; and ABAB; wherein each A is a modified nucleoside of a first type, each B is a modified nucleoside of a second type, and each W is a modified nucleoside of either the first type, the second type or a third type.

In certain embodiments, an oligonucleotide comprises any 5'-wing motif provided herein. In certain such embodiments, the oligonucleotide is a 5'-hemimer (does not comprise a 3'-wing). In certain embodiments, such an oligonucleotide is a gapmer. In certain such embodiments, the 3'-wing of the gapmer may comprise any nucleoside motif.

In certain embodiments, the 5'-wing of a gapmer has a sugar motif selected from among those listed in the following non-limiting tables:

TABLE 1

Certain 5'-Wing Sugar Motifs
Certain 5'-Wing Sugar Motifs

| | | | | |
|---|---|---|---|---|
| AAAAA | ABCBB | BABCC | BCBBA | CBACC |
| AAAAB | ABCBC | BACAA | BCBBB | CBBAA |
| AAAAC | ABCCA | BACAB | BCBBC | CBBAB |
| AAABA | ABCCB | BACAC | BCBCA | CBBAC |
| AAABB | ABCCC | BACBA | BCBCB | CBBBA |
| AAABC | ACAAA | BACBB | BCBCC | CBBBB |
| AAACA | ACAAB | BACBC | BCCAA | CBBBC |
| AAACB | ACAAC | BACCA | BCCAB | CBBCA |
| AAACC | ACABA | BACCB | BCCAC | CBBCB |
| AABAA | ACABB | BACCC | BCCBA | CBBCC |
| AABAB | ACABC | BBAAA | BCCBB | CBCAA |
| AABAC | ACACA | BBAAB | BCCBC | CBCAB |
| AABBA | ACACB | BBAAC | BCCCA | CBCAC |
| AABBB | ACACC | BBABA | BCCCB | CBCBA |
| AABBC | ACBAA | BBABB | BCCCC | CBCBB |
| AABCA | ACBAB | BBABC | CAAAA | CBCBC |
| AABCB | ACBAC | BBACA | CAAAB | CBCCA |
| AABCC | ACBBA | BBACB | CAAAC | CBCCB |
| AACAA | ACBBB | BBACC | CAABA | CBCCC |
| AACAB | ACBBC | BBBAA | CAABB | CCAAA |
| AACAC | ACBCA | BBBAB | CAABC | CCAAB |
| AACBA | ACBCB | BBBAC | CAACA | CCAAC |
| AACBB | ACBCC | BBBBA | CAACB | CCABA |
| AACBC | ACCAA | BBBBB | CAACC | CCABB |
| AACCA | ACCAB | BBBBC | CABAA | CCABC |
| AACCB | ACCAC | BBBCA | CABAB | CCACA |
| AACCC | ACCBA | BBBCB | CABAC | CCACB |
| ABAAA | ACCBB | BBBCC | CABBA | CCACC |
| ABAAB | ACCBC | BBCAA | CABBB | CCBAA |
| ABAAC | ACCCA | BBCAB | CABBC | CCBAB |
| ABABA | ACCCB | BBCAC | CABCA | CCBAC |
| ABABB | ACCCC | BBCBA | CABCB | CCBBA |
| ABABC | BAAAA | BBCBB | CABCC | CCBBB |
| ABACA | BAAAB | BBCBC | CACAA | CCBBC |
| ABACB | BAAAC | BBCCA | CACAB | CCBCA |
| ABACC | BAABA | BBCCB | CACAC | CCBCB |
| ABBAA | BAABB | BBCCC | CACBA | CCBCC |
| ABBAB | BAABC | BCAAA | CACBB | CCCAA |
| ABBAC | BAACA | BCAAB | CACBC | CCCAB |
| ABBBA | BAACB | BCAAC | CACCA | CCCAC |
| ABBBB | BAACC | BCABA | CACCB | CCCBA |
| ABBBC | BABAA | BCABB | CACCC | CCCBB |
| ABBCA | BABAB | BCABC | CBAAA | CCCBC |
| ABBCB | BABAC | BCACA | CBAAB | CCCCA |
| ABBCC | BABBA | BCACB | CBAAC | CCCCB |
| ABCAA | BABBB | BCACC | CBABA | CCCCC |
| ABCAB | BABBC | BCBAA | CBABB | |
| ABCAC | BABCA | BCBAB | CBABC | |
| ABCBA | BABCB | BCBAC | CBACA | |

TABLE 2

Certain 5'-Wing Sugar Motifs
Certain 5'-Wing Sugar Motifs

| | | | | |
|---|---|---|---|---|
| AAAAA | BABC | CBAB | ABBB | BAA |
| AAAAB | BACA | CBAC | BAAA | BAB |
| AAABA | BACB | CBBA | BAAB | BBA |
| AAABB | BACC | CBBB | BABA | BBB |
| AABAA | BBAA | CBBC | BABB | AA |
| AABAB | BBAB | CBCA | BBAA | AB |
| AABBA | BBAC | CBCB | BBAB | AC |

TABLE 2-continued

Certain 5'-Wing Sugar Motifs
Certain 5'-Wing Sugar Motifs

| | | | | |
|---|---|---|---|---|
| AABBB | BBBA | CBCC | BBBA | BA |
| ABAAA | BBBB | CCAA | BBBB | BB |
| ABAAB | BBBC | CCAB | AAA | BC |
| ABABA | BBCA | CCAC | AAB | CA |
| ABABB | BBCB | CCBA | AAC | CB |
| ABBAA | BBCC | CCBB | ABA | CC |
| ABBAB | BCAA | CCBC | ABB | AA |
| ABBBA | BCAB | CCCA | ABC | AB |
| ABBBB | BCAC | CCCB | ACA | BA |
| BAAAA | ABCB | BCBA | ACB | |
| BAAAB | ABCC | BCBB | ACC | |
| BAABA | ACAA | BCBC | BAA | |
| BAABB | ACAB | BCCA | BAB | |
| BABAA | ACAC | BCCB | BAC | |
| BABAB | ACBA | BCCC | BBA | |
| BABBA | ACBB | CAAA | BBB | |
| BABBB | ACBC | CAAB | BBC | |
| BBAAA | ACCA | CAAC | BCA | |
| BBAAB | ACCB | CABA | BCB | |
| BBABA | ACCC | CABB | BCC | |
| BBABB | BAAA | CABC | CAA | |
| BBBAA | BAAB | CACA | CAB | |
| BBBAB | BAAC | CACB | CAC | |
| BBBBA | BABA | CACC | CBA | |
| BBBBB | BABB | CBAA | CBB | |
| AAAA | AACC | CCCC | CBC | |
| AAAB | ABAA | AAAA | CCA | |
| AAAC | ABAB | AAAB | CCB | |
| AABA | ABAC | AABA | CCC | |
| AABB | ABBA | AABB | AAA | |
| AABC | ABBB | ABAA | AAB | |
| AACA | ABBC | ABAB | ABA | |
| AACB | ABCA | ABBA | ABB | |

In certain embodiments, each A, each B, and each C located at the 3'-most 5'-wing nucleoside is a modified nucleoside. For example, in certain embodiments the 5'-wing motif is selected from among ABB BBB, and CBB, wherein the underlined nucleoside represents the 3'-most 5'-wing nucleoside and wherein the underlined nucleoside is a modified nucleoside. In certain embodiments, the 3'-most 5'-wing nucleoside comprises a bicyclic sugar moiety selected from among cEt, cMOE, LNA, α-L-LNA, ENA and 2'-thio LNA. In certain embodiments, the 3'-most 5'-wing nucleoside comprises a bicyclic sugar moiety selected from among cEt and LNA. In certain embodiments, the 3'-most 5'-wing nucleoside comprises cEt. In certain embodiments, the 3'-most 5'-wing nucleoside comprises LNA.

In certain embodiments, each A comprises an unmodified 2'-deoxyfuranose sugar moiety. In certain embodiments, each A comprises a modified sugar moiety. In certain embodiments, each A comprises a 2'-substituted sugar moiety. In certain embodiments, each A comprises a 2'-substituted sugar moiety selected from among F, ara-F, $OCH_3$ and $O(CH_2)_2$—$OCH_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A comprises a modified nucleobase. In certain embodiments, each A comprises a modified nucleobase selected from among 2-thio-thymidine nucleoside and 5-propyne uridine nucleoside. In certain embodiments, each A comprises an HNA. In certain embodiments, each A comprises a F-HNA. In certain embodiments, each A comprises a 5'-substituted sugar moiety selected from among 5'-Me DNA, and 5'-(R)-Me DNA.

In certain embodiments, each B comprises an unmodified 2'-deoxyfuranose sugar moiety. In certain embodiments, each B comprises a modified sugar moiety. In certain embodiments, each B comprises a 2'-substituted sugar moiety. In certain embodiments, each B comprises a 2'-substituted sugar moiety selected from among F, (ara)-F, $OCH_3$ and $O(CH_2)_2$—$OCH_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B comprises a modified nucleobase. In certain embodiments, each B comprises a modified nucleobase selected from among 2-thio-thymidine nucleoside and 5-propyne urindine nucleoside. In certain embodiments, each B comprises an HNA. In certain embodiments, each B comprises a F-HNA. In certain embodiments, each B comprises a 5'-substituted sugar moiety selected from among 5'-Me DNA, and 5'-(R)-Me DNA.

In certain embodiments, each A comprises a 2'-substituted sugar moiety selected from among F, ara-F, $OCH_3$ and $O(CH_2)_2$—$OCH_3$ and each B comprises a bicyclic sugar moiety selected from among cEt, cMOE, LNA, α-L-LNA, ENA and 2'-thio LNA. In certain embodiments, each A comprises $O(CH_2)_2$—$OCH_3$ and each B comprises cEt.

In certain embodiments, each C comprises an unmodified 2'-deoxyfuranose sugar moiety. In certain embodiments, each C comprises a modified sugar moiety. In certain embodiments, each C comprises a 2'-substituted sugar moiety. In certain embodiments, each C comprises a 2'-substituted sugar moiety selected from among F, (ara)-F, $OCH_3$ and $O(CH_2)_2$—$OCH_3$. In certain embodiments, each C comprises a 5'-substituted sugar moiety. In certain embodiments, each C comprises a 5'-substituted sugar moiety selected from among 5'-Me DNA, and 5'-(R)-Me DNA. In certain embodiments, each C comprises a bicyclic sugar moiety. In certain embodiments, each C comprises a bicyclic sugar moiety selected from among cEt, cMOE, LNA, α-L-LNA, ENA and 2'-thio LNA. In certain embodiments, each C comprises a modified nucleobase. In certain embodiments, each C comprises a modified nucleobase selected from among 2-thio-thymidine and 5-propyne uridine. In certain embodiments, each C comprises a 2-thio-thymidine nucleoside. In certain embodiments, each C comprises an HNA. In certain embodiments, each C comprises an F-HNA.

v. Certain 3'-wings

In certain embodiments, the 3'-wing of a gapmer consists of 1 to 6 linked nucleosides. In certain embodiments, the 3'-wing of a gapmer consists of 1 to 5 linked nucleosides. In certain embodiments, the 3'-wing of a gapmer consists of 2 to 5 linked nucleosides. In certain embodiments, the 3'-wing of a gapmer consists of 3 to 5 linked nucleosides. In certain embodiments, the 3'-wing of a gapmer consists of 4 or 5 linked nucleosides. In certain embodiments, the 3'-wing of a gapmer consists of 1 to 4 linked nucleosides.

In certain embodiments, the 3'-wing of a gapmer consists of 1 to 3 linked nucleosides. In certain embodiments, the 3'-wing of a gapmer consists of 1 or 2 linked nucleosides. In certain embodiments, the 3'-wing of a gapmer consists of 2 to 4 linked nucleosides. In certain embodiments, the 3'-wing of a gapmer consists of 2 or 3 linked nucleosides. In certain embodiments, the 3'-wing of a gapmer consists of 3 or 4 linked nucleosides. In certain embodiments, the 3'-wing of a gapmer consists of 1 nucleoside. In certain embodiments, the 3'-wing of a gapmer consists of 2 linked nucleosides. In certain embodiments, the 3'-wing of a gapmer consists of 3 linked nucleosides. In certain embodiments, the 3'-wing of a gapmer consists of 4 linked nucleosides. In certain embodiments, the 3'-wing of a gapmer consists of 5 linked nucleosides. In certain embodiments, the 3'-wing of a gapmer consists of 6 linked nucleosides.

In certain embodiments, the 3'-wing of a gapmer comprises at least one bicyclic nucleoside. In certain embodiments, the 3'-wing of a gapmer comprises at least one constrained ethyl nucleoside. In certain embodiments, the 3'-wing of a gapmer comprises at least one LNA nucleoside. In certain embodiments, each nucleoside of the 3'-wing of a gapmer is a bicyclic nucleoside. In certain embodiments, each nucleoside of the 3'-wing of a gapmer is a constrained ethyl nucleoside. In certain embodiments, each nucleoside of the 3'-wing of a gapmer is a LNA nucleoside.

In certain embodiments, the 3'-wing of a gapmer comprises at least one non-bicyclic modified nucleoside. In certain embodiments, the 3'-wing of a gapmer comprises at least two non-bicyclic modified nucleosides. In certain embodiments, the 3'-wing of a gapmer comprises at least three non-bicyclic modified nucleosides. In certain embodiments, the 3'-wing of a gapmer comprises at least four non-bicyclic modified nucleosides. In certain embodiments, the 3'-wing of a gapmer comprises at least one 2'-substituted nucleoside. In certain embodiments, the 3'-wing of a gapmer comprises at least one 2'-MOE nucleoside. In certain embodiments, the 3'-wing of a gapmer comprises at least one 2'-OMe nucleoside. In certain embodiments, each nucleoside of the 3'-wing of a gapmer is a non-bicyclic modified nucleoside. In certain embodiments, each nucleoside of the 3'-wing of a gapmer is a 2'-substituted nucleoside. In certain embodiments, each nucleoside of the 3'-wing of a gapmer is a 2'-MOE nucleoside. In certain embodiments, each nucleoside of the 3'-wing of a gapmer is a 2'-OMe nucleoside.

In certain embodiments, the 3'-wing of a gapmer comprises at least one 2'-deoxynucleoside. In certain embodiments, each nucleoside of the 3'-wing of a gapmer is a 2'-deoxynucleoside. In a certain embodiments, the 3'-wing of a gapmer comprises at least one ribonucleoside. In certain embodiments, each nucleoside of the 3'-wing of a gapmer is a ribonucleoside. In certain embodiments, one, more than one, or each of the nucleosides of the 5'-wing is an RNA-like nucleoside.

In certain embodiments, the 3'-wing of a gapmer comprises at least one bicyclic nucleoside and at least one non-bicyclic modified nucleoside. In certain embodiments, the 3'-wing of a gapmer comprises at least one bicyclic nucleoside and at least one 2'-substituted nucleoside. In certain embodiments, the 3'-wing of a gapmer comprises at least one bicyclic nucleoside and at least one 2'-MOE nucleoside. In certain embodiments, the 3'-wing of a gapmer comprises at least one bicyclic nucleoside and at least one 2'-OMe nucleoside. In certain embodiments, the 3'-wing of a gapmer comprises at least one bicyclic nucleoside and at least one 2'-deoxynucleoside.

In certain embodiments, the 3'-wing of a gapmer comprises at least one constrained ethyl nucleoside and at least one non-bicyclic modified nucleoside. In certain embodiments, the 3'-wing of a gapmer comprises at least one constrained ethyl nucleoside and at least one 2'-substituted nucleoside. In certain embodiments, the 3'-wing of a gapmer comprises at least one constrained ethyl nucleoside and at least one 2'-MOE nucleoside. In certain embodiments, the 3'-wing of a gapmer comprises at least one constrained ethyl nucleoside and at least one 2'-OMe nucleoside. In certain embodiments, the 3'-wing of a gapmer comprises at least one constrained ethyl nucleoside and at least one 2'-deoxynucleoside.

In certain embodiments, the 3'-wing of a gapmer comprises at least one LNA nucleoside and at least one non-bicyclic modified nucleoside. In certain embodiments, the 3'-wing of a gapmer comprises at least one LNA nucleoside and at least one 2'-substituted nucleoside. In certain embodiments, the 3'-wing of a gapmer comprises at least one LNA nucleoside and at least one 2'-MOE nucleoside. In certain embodiments, the 3'-wing of a gapmer comprises at least one LNA nucleoside and at least one 2'-OMe nucleoside. In certain embodiments, the 3'-wing of a gapmer comprises at least one LNA nucleoside and at least one 2'-deoxynucleoside.

In certain embodiments, the 3'-wing of a gapmer comprises at least one bicyclic nucleoside, at least one non-bicyclic modified nucleoside, and at least one 2'-deoxynucleoside. In certain embodiments, the 3'-wing of a gapmer comprises at least one constrained ethyl nucleoside, at least one non-bicyclic modified nucleoside, and at least one 2'-deoxynucleoside. In certain embodiments, the 3'-wing of a gapmer comprises at least one LNA nucleoside, at least one non-bicyclic modified nucleoside, and at least one 2'-deoxynucleoside.

In certain embodiments, the 3'-wing of a gapmer comprises at least one bicyclic nucleoside, at least one 2'-substituted nucleoside, and at least one 2'-deoxynucleoside. In certain embodiments, the 3'-wing of a gapmer comprises at least one constrained ethyl nucleoside, at least one 2'-substituted nucleoside, and at least one 2'-deoxynucleoside. In certain embodiments, the 3'-wing of a gapmer comprises at least one LNA nucleoside, at least one 2'-substituted nucleoside, and at least one 2'-deoxynucleoside.

In certain embodiments, the 3'-wing of a gapmer comprises at least one bicyclic nucleoside, at least one 2'-MOE nucleoside, and at least one 2'-deoxynucleoside. In certain embodiments, the 3'-wing of a gapmer comprises at least one constrained ethyl nucleoside, at least one 2'-MOE nucleoside, and at least one 2'-deoxynucleoside. In certain embodiments, the 3'-wing of a gapmer comprises at least one LNA nucleoside, at least one 2'-MOE nucleoside, and at least one 2'-deoxynucleoside.

In certain embodiments, the 3'-wing of a gapmer comprises at least one bicyclic nucleoside, at least one 2'-OMe nucleoside, and at least one 2'-deoxynucleoside. In certain embodiments, the 3'-wing of a gapmer comprises at least one constrained ethyl nucleoside, at least one 2'-OMe nucleoside, and at least one 2'-deoxynucleoside. In certain embodiments, the 3'-wing of a gapmer comprises at least one LNA nucleoside, at least one 2'-OMe nucleoside, and at least one 2'-deoxynucleoside.

In certain embodiments, the 3'-wing of a gapmer has a nucleoside motif selected from among the following: ABB, ABAA, AAABAA, AAAAABAA, AABAA, AAAABAA, AAABAA, ABAB, AAAAA, AAABB, AAAAAAAA, AAAAAAA, AAAAAA, AAAAB, AAAA, AAA, AA, AB, ABBB, ABAB, AABBB; wherein each A is a modified nucleoside of a first type, each B is a modified nucleoside of a second type. In certain embodiments, an oligonucleotide comprises any 3'-wing motif provided herein. In certain such embodiments, the oligonucleotide is a 3'-hemimer (does not comprise a 5'-wing). In certain embodiments, such an oligonucleotide is a gapmer. In certain such embodiments, the 5'-wing of the gapmer may comprise any nucleoside motif.

In certain embodiments, the 3'-wing of a gapmer has a nucleoside motif selected from among the following: BBA, AAB, AAA, BBB, BBAA, AABB, WBBA, WAAB, BBBA, BBBBA, BBBB, BBBBBA, ABBBBB, BBAAA, AABBB, BBBAA, BBBBA, BBBBB, BABA, AAAAA, BBAAAA, AABBBB, BAAAA, and ABBBB, wherein each A is a modified nucleoside of a first type, each B is a modified nucleoside of a second type, and each W is a modified nucleoside of either the first type, the second type or a third type.

In certain embodiments, the 3'-wing of a gapmer has a nucleoside motif selected from among the following: ABB; AAABAA; AABAA; AAAABAA; AAAAA; AAABB; AAAAAAAA; AAAAAAA; AAAAAA; AAAAB; AB; ABBB; and ABAB, wherein each A is a modified nucleoside of a first type, each B is a modified nucleoside of a second type, and each W is a modified nucleoside of either the first type, the second type or a third type.

In certain embodiments, the 3'-wing of a gapmer has a sugar motif selected from among those listed in the following non-limiting tables:

TABLE 3

Certain 3'-Wing Sugar Motifs
Certain 3'-Wing Sugar Motifs

| | | | | |
|---|---|---|---|---|
| AAAAA | ABCBB | BABCC | BCBBA | CBACC |
| AAAAB | ABCBC | BACAA | BCBBB | CBBAA |
| AAAAC | ABCCA | BACAB | BCBBC | CBBAB |
| AAABA | ABCCB | BACAC | BCBCA | CBBAC |
| AAABB | ABCCC | BACBA | BCBCB | CBBBA |
| AAABC | ACAAA | BACBB | BCBCC | CBBBB |
| AACAA | ACAAB | BACBC | BCCAA | CBBBC |
| AACAB | ACAAC | BACCA | BCCAB | CBBCA |
| AACAC | ACABA | BACCB | BCCAC | CBBCB |
| AABAA | ACABB | BACCC | BCCBA | CBBCC |
| AABAB | ACABC | BBAAA | BCCBB | CBCAA |
| AABAC | ACACA | BBAAB | BCCBC | CBCAB |
| AABBA | ACACB | BBAAC | BCCCA | CBCAC |
| AABBB | ACACC | BBABA | BCCCB | CBCBA |
| AABBC | ACBAA | BBABB | BCCCC | CBCBB |
| AABCA | ACBAB | BBABC | CAAAA | CBCBC |
| AABCB | ACBAC | BBACA | CAAAB | CBCCA |
| AABCC | ACBBA | BBACB | CAAAC | CBCCB |
| AACAA | ACBBB | BBACC | CAABA | CBCCC |
| AACAB | ACBBC | BBBAA | CAABB | CCAAA |
| AACAC | ACBCA | BBBAB | CAABC | CCAAB |
| AACBA | ACBCB | BBBAC | CAACA | CCAAC |
| AACBB | ACBCC | BBBBA | CAACB | CCABA |
| AACBC | ACCAA | BBBBB | CAACC | CCABB |
| AACCA | ACCAB | BBBBC | CABAA | CCABC |
| AACCB | ACCAC | BBBCA | CABAB | CCACA |
| AACCC | ACCBA | BBBCB | CABAC | CCACB |
| ABAAA | ACCBB | BBBCC | CABBA | CCACC |
| ABAAB | ACCBC | BBCAA | CABBB | CCBAA |
| ABAAC | ACCCA | BBCAB | CABBC | CCBAB |
| ABABA | ACCCB | BBCAC | CABCA | CCBAC |
| ABABB | ACCCC | BBCBA | CABCB | CCBBA |
| ABABC | BAAAA | BBCBB | CABCC | CCBBB |
| ABACA | BAAAB | BBCBC | CACAA | CCBBC |
| ABACB | BAAAC | BBCCA | CACAB | CCBCA |
| ABACC | BAABA | BBCCB | CACAC | CCBCB |
| ABBAA | BAABB | BBCCC | CACBA | CCBCC |
| ABBAB | BAABC | BCAAA | CACBB | CCCAA |
| ABBAC | BAACA | BCAAB | CACBC | CCCAB |
| ABBBA | BAACB | BCAAC | CACCA | CCCAC |
| ABBBB | BAACC | BCABA | CACCB | CCCBA |
| ABBBC | BABAA | BCABB | CACCC | CCCBB |
| ABBCA | BABAB | BCABC | CBAAA | CCCBC |
| ABBCB | BABAC | BCACA | CBAAB | CCCCA |
| ABBCC | BABBA | BCACB | CBAAC | CCCCB |
| ABCAA | BABBB | BCACC | CBABA | CCCCC |
| ABCAB | BABBC | BCBAA | CBABB | |
| ABCAC | BABCA | BCBAB | CBABC | |
| ABCBA | BABCB | BCBAC | CBACA | |

TABLE 4

Certain 3'-Wing Sugar Motifs
Certain 3'-Wing Sugar Motifs

| | | | | |
|---|---|---|---|---|
| AAAAA | BABC | CBAB | ABBB | BAA |
| AAAAB | BACA | CBAC | BAAA | BAB |
| AAABA | BACB | CBBA | BAAB | BBA |
| AAABB | BACC | CBBB | BABA | BBB |
| AABAA | BBAA | CBBC | BABB | AA |

TABLE 4-continued

Certain 3'-Wing Sugar Motifs
Certain 3'-Wing Sugar Motifs

| | | | | |
|---|---|---|---|---|
| AABAB | BBAB | CBCA | BBAA | AB |
| AABBA | BBAC | CBCB | BBAB | AC |
| AABBB | BBBA | CBCC | BBBA | BA |
| ABAAA | BBBB | CCAA | BBBB | BB |
| ABAAB | BBBC | CCAB | AAA | BC |
| ABABA | BBCA | CCAC | AAB | CA |
| ABABB | BBCB | CCBA | AAC | CB |
| ABBAA | BBCC | CCBB | ABA | CC |
| ABBAB | BCAA | CCBC | ABB | AA |
| ABBBA | BCAB | CCCA | ABC | AB |
| ABBBB | BCAC | CCCB | ACA | BA |
| BAAAA | ABCB | BCBA | ACB | |
| BAAAB | ABCC | BCBB | ACC | |
| BAABA | ACAA | BCBC | BAA | |
| BAABB | ACAB | BCCA | BAB | |
| BABAA | ACAC | BCCB | BAC | |
| BABAB | ACBA | BCCC | BBA | |
| BABBA | ACBB | CAAA | BBB | |
| BABBB | ACBC | CAAB | BBC | |
| BBAAA | ACCA | CAAC | BCA | |
| BBAAB | ACCB | CABA | BCB | |
| BBABA | ACCC | CABB | BCC | |
| BBABB | BAAA | CABC | CAA | |
| BBBAA | BAAB | CACA | CAB | |
| BBBAB | BAAC | CACB | CAC | |
| BBBBA | BABA | CACC | CBA | |
| BBBBB | BABB | CBAA | CBB | |
| AAAA | AACC | CCCC | CBC | |
| AAAB | ABAA | AAAA | CCA | |
| AAAC | ABAB | AAAB | CCB | |
| AABA | ABAC | AABA | CCC | |
| AABB | ABBA | AABB | AAA | |
| AABC | ABBB | ABAA | AAB | |
| AACA | ABBC | ABAB | ABA | |
| AACB | ABCA | ABBA | ABB | |

In certain embodiments, each A, each B, and each C located at the 5'-most 3'-wing region nucleoside is a modified nucleoside. For example, in certain embodiments the 3'-wing motif is selected from among ABB, BBB, and CBB, wherein the underlined nucleoside represents the 5'-most 3'-wing region nucleoside and wherein the underlined nucleoside is a modified nucleoside.

In certain embodiments, each A comprises an unmodified 2'-deoxyfuranose sugar moiety. In certain embodiments, each A comprises a modified sugar moiety. In certain embodiments, each A comprises a 2'-substituted sugar moiety. In certain embodiments, each A comprises a 2'-substituted sugar moiety selected from among F, ara-F, OCH$_3$ and O(CH$_2$)$_2$—OCH$_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A comprises a modified nucleobase. In certain embodiments, each A comprises a modified nucleobase selected from among 2-thio-thymidine nucleoside and 5-propyne uridine nucleoside. In certain embodiments, each A comprises a 5'-substituted sugar moiety selected from among 5'-Me DNA, and 5'-(R)-Me DNA.

In certain embodiments, each B comprises an unmodified 2'-deoxyfuranose sugar moiety. In certain embodiments, each B comprises a modified sugar moiety. In certain embodiments, each B comprises a 2'-substituted sugar moiety. In certain embodiments, each B comprises a 2'-substituted sugar moiety selected from among F, (ara)-F, OCH$_3$ and O(CH$_2$)$_2$—OCH$_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA.

In certain embodiments, each B comprises a modified nucleobase. In certain embodiments, each B comprises a modified nucleobase selected from among 2-thio-thymidine nucleoside and 5-propyne urindine nucleoside. In certain embodiments, each B comprises an HNA. In certain embodiments, each B comprises an F-HNA. In certain embodiments, each B comprises a 5'-substituted sugar moiety selected from among 5'-Me DNA, and 5'-(R)-Me DNA.

In certain embodiments, each A comprises a 2'-substituted sugar moiety selected from among F, ara-F, OCH$_3$ and O(CH$_2$)$_2$—OCH$_3$ and each B comprises a bicyclic sugar moiety selected from among cEt, cMOE, LNA, α-L-LNA, ENA and 2'-thio LNA. In certain embodiments, each A comprises O(CH$_2$)$_2$—OCH$_3$ and each B comprises cEt.

In certain embodiments, each C comprises an unmodified 2'-deoxyfuranose sugar moiety. In certain embodiments, each C comprises a modified sugar moiety. In certain embodiments, each C comprises a 2'-substituted sugar moiety. In certain embodiments, each C comprises a 2'-substituted sugar moiety selected from among F, (ara)-F, OCH$_3$ and O(CH$_2$)$_2$—OCH$_3$. In certain embodiments, each C comprises a 5'-substituted sugar moiety. In certain embodiments, each C comprises a 5'-substituted sugar moiety selected from among 5'-Me, and 5'-(R)-Me. In certain embodiments, each C comprises a bicyclic sugar moiety. In certain embodiments, each C comprises a bicyclic sugar moiety selected from among cEt, cMOE, LNA, α-L-LNA, ENA and 2'-thio LNA. In certain embodiments, each C comprises a modified nucleobase. In certain embodiments, each C comprises a modified nucleobase selected from among 2-thio-thymidine and 5-propyne uridine. In certain embodiments, each C comprises a 2-thio-thymidine nucleoside. In certain embodiments, each C comprises an HNA. In certain embodiments, each C comprises an F-HNA.

vi. Certain Central Regions (Gaps)

In certain embodiments, the gap of a gapmer consists of 6 to 20 linked nucleosides. In certain embodiments, the gap of a gapmer consists of 6 to 15 linked nucleosides. In certain embodiments, the gap of a gapmer consists of 6 to 12 linked nucleosides. In certain embodiments, the gap of a gapmer consists of 6 to 10 linked nucleosides. In certain embodiments, the gap of a gapmer consists of 6 to 9 linked nucleosides. In certain embodiments, the gap of a gapmer consists of 6 to 8 linked nucleosides. In certain embodiments, the gap of a gapmer consists of 6 or 7 linked nucleosides. In certain embodiments, the gap of a gapmer consists of 7 to 10 linked nucleosides. In certain embodiments, the gap of a gapmer consists of 7 to 9 linked nucleosides. In certain embodiments, the gap of a gapmer consists of 7 or 8 linked nucleosides. In certain embodiments, the gap of a gapmer consists of 8 to 10 linked nucleosides. In certain embodiments, the gap of a gapmer consists of 8 or 9 linked nucleosides. In certain embodiments, the gap of a gapmer consists of 6 linked nucleosides. In certain embodiments, the gap of a gapmer consists of 7 linked nucleosides. In certain embodiments, the gap of a gapmer consists of 8 linked nucleosides. In certain embodiments, the gap of a gapmer consists of 9 linked nucleosides. In certain embodiments, the gap of a gapmer consists of 10 linked nucleosides. In certain embodiments, the gap of a gapmer consists of 11 linked nucleosides. In certain embodiments, the gap of a gapmer consists of 12 linked nucleosides.

In certain embodiments, each nucleoside of the gap of a gapmer is a 2'-deoxynucleoside. In certain embodiments, the gap comprises one or more modified nucleosides. In certain embodiments, each nucleoside of the gap of a gapmer is a 2'-deoxynucleoside or is a modified nucleoside that is "DNA-like." In such embodiments, "DNA-like" means that the nucleoside has similar characteristics to DNA, such that a duplex comprising the gapmer and an RNA molecule is capable of activating RNase H. For example, under certain conditions, 2'-(ara)-F have been shown to support RNase H activation, and thus is DNA-like. In certain embodiments, one or more nucleosides of the gap of a gapmer is not a 2'-deoxynucleoside and is not DNA-like. In certain such embodiments, the gapmer nonetheless supports RNase H activation (e.g., by virtue of the number or placement of the non-DNA nucleosides).

In certain embodiments, gaps comprise a stretch of unmodified 2'-deoxynucleoside interrupted by one or more modified nucleosides, thus resulting in three sub-regions (two stretches of one or more 2'-deoxynucleosides and a stretch of one or more interrupting modified nucleosides). In certain embodiments, no stretch of unmodified 2'-deoxynucleosides is longer than 5, 6, or 7 nucleosides. In certain embodiments, such short stretches is achieved by using short gap regions. In certain embodiments, short stretches are achieved by interrupting a longer gap region.

In certain embodiments, the gap comprises one or more modified nucleosides. In certain embodiments, the gap comprises one or more modified nucleosides selected from among cEt, FHNA, LNA, and 2-thio-thymidine. In certain embodiments, the gap comprises one modified nucleoside. In certain embodiments, the gap comprises a 5'-substituted sugar moiety selected from among 5'-Me, and 5'-(R)-Me. In certain embodiments, the gap comprises two modified nucleosides. In certain embodiments, the gap comprises three modified nucleosides. In certain embodiments, the gap comprises four modified nucleosides. In certain embodiments, the gap comprises two or more modified nucleosides and each modified nucleoside is the same. In certain embodiments, the gap comprises two or more modified nucleosides and each modified nucleoside is different.

In certain embodiments, the gap comprises one or more modified linkages. In certain embodiments, the gap comprises one or more methyl phosphonate linkages. In certain embodiments the gap comprises two or more modified linkages. In certain embodiments, the gap comprises one or more modified linkages and one or more modified nucleosides. In certain embodiments, the gap comprises one modified linkage and one modified nucleoside. In certain embodiments, the gap comprises two modified linkages and two or more modified nucleosides.

In certain embodiments, the gap comprises a nucleoside motif selected from among the following: DDDDXDDDDD; DDDDDXDDDDD; DDDXDDDDD; DDDDXDDDDDD; DDDDXDDDD; DDXDDDDDD; DDDXDDDDDD; DXDDDDDD; DDXDDDDDDD; DDXDDDDD; DDXDDDXDDD; DDDXDDDXDDD; DXDDDXDDD; DDXDDDXDD; DDXDDDDXDDD; DDXDDDDXDD; DXDDDDXDDD; DDDDXDDD; DDDXDDD; DXDDDDDDD; DDDDXXDDD; and DXXDXXDXX; wherein each D is an unmodified deoxynucleoside; and each X is a modified nucleoside or a substituted sugar moiety.

In certain embodiments, the gap comprises a nucleoside motif selected from among the following: DDDDDDDDD; DXDDDDDDD; DDXDDDDDD; DDDXDDDDD; DDDDXDDDD; DDDDDXDDD; DDDDDDXDD; DDDDDDDXD; DXXDDDDDD; DDDDDDXXD; DDXXDDDDD; DDDXXDDDD; DDDDXXDDD; DDDDDXXDD; DXDDDDDXD; DXDDDDXDD; DXDDDXDDD; DXDDXDDDD; DXDXDDDDD; DDXDDDDXD; DDXDDDXDD; DDXDDXDDD;

DDXDXDDD; DDDXDDDXD; DDDXDDXDD; DDDXDXDDD; DDDDXDDXD; DDDDXDXDD; and DDDDDXDXD, wherein each D is an unmodified deoxynucleoside; and each X is a modified nucleoside or a substituted sugar moiety.

In certain embodiments, the gap comprises a nucleoside motif selected from among the following: DDDDXDDDD, DXDDDDDDD, DXXDDDDDD, DDXDDDDDD, DDDXDDDDD, DDDDXDDDD, DDDDDXDDD, DDDDDDXDD, and DDDDDDDXD, wherein each D is an unmodified deoxynucleoside; and each X is a modified nucleoside or a substituted sugar moiety.

In certain embodiments, the gap comprises a nucleoside motif selected from among the following: DDDDDDDD, DXDDDDDD, DDXDDDDD, DDDXDDDD, DDDDXDDD, DDDDDXDD, DDDDDDXD, DXDDDDXD, DXDDDXDD, DXDDXDDD, DXDXDDDD, DXXDDDDD, DDXXDDDD, DDXDXDDD, DDXDDXDD, DXDDDDXD, DDDXXDDD, DDDXDXDD, DDDXDDXD, DDDDXXDD, DDDDXDXD, and DDDDDXXD, wherein each D is an unmodified deoxynucleoside; and each X is a modified nucleoside or a substituted sugar moiety.

In certain embodiments, the gap comprises a nucleoside motif selected from among the following: DXDDDDD, DDXDDDD, DDDXDDD, DDDDXDD, DDDDDXD, DXDDDXD, DXDDXDD, DXDXDDD, DXXDDDD, DDXXDDD, DDXDXDD, DDXDDXD, DDDXXDD, DDDXDXD, and DDDDXXD, wherein each D is an unmodified deoxynucleoside; and each X is a modified nucleoside or a substituted sugar moiety.

In certain embodiments, the gap comprises a nucleoside motif selected from among the following: DXDDDD, DDXDDD, DDDXDD, DDDDXD, DXXDDD, DXDXDD, DXDDXD, DDXXDD, DDXDXD, and DDDXXD, wherein each D is an unmodified deoxynucleoside; and each X is a modified nucleoside or a substituted sugar moiety.

In certain embodiments, the gap comprises a nucleoside motif selected from among the following: DXDDDD, DDXDDD, DDDXDD, DDDDXD, DXDDDDD, DDXDDDD, DDDXDDD, DDDDXDD, DDDDDXD, DXDDDDDD, DDXDDDDD, DDDXDDDD, DDDDXDDD, DDDDDXDD, DDDDDDXD, DXDDDDDDD; DDXDDDDDD, DDDXDDDDD, DDDDXDDDD, DDDDDXDDD, DDDDDDXDD, DDDDDDDXD, DXDDDDDDDD, DDXDDDDDDD, DDDXDDDDDD, DDDDXDDDDD, DDDDDXDDDD, DDDDDDXDDD, DDDDDDDXDD, and DDDDDDDDXD, wherein each D is an unmodified deoxynucleoside; and each X is a modified nucleoside or a substituted sugar moiety.

In certain embodiments, each X comprises an unmodified 2'-deoxyfuranose sugar moiety. In certain embodiments, each X comprises a modified sugar moiety. In certain embodiments, each X comprises a 2'-substituted sugar moiety. In certain embodiments, each X comprises a 2'-substituted sugar moiety selected from among F, (ara)-F, OCH$_3$ and O(CH$_2$)$_2$—OCH$_3$. In certain embodiments, each X comprises a 5'-substituted sugar moiety. In certain embodiments, each X comprises a 5'-substituted sugar moiety selected from among 5'-Me, and 5'-(R)-Me. In certain embodiments, each X comprises a bicyclic sugar moiety. In certain embodiments, each X comprises a bicyclic sugar moiety selected from among cEt, cMOE, LNA, α-L-LNA, ENA and 2'-thio LNA. In certain embodiments, each X comprises a modified nucleobase. In certain embodiments, each X comprises a modified nucleobase selected from among 2-thio-thymidine and 5-propyne uridine. In certain embodiments, each X comprises a 2-thio-thymidine nucleoside. In certain embodiments, each X comprises an HNA. In certain embodiments, each C comprises an F-HNA. In certain embodiments, X represents the location of a single differentiating nucleobase.

vii. Certain Gapmer Motifs

In certain embodiments, a gapmer comprises a 5'-wing, a gap, and a 3' wing, wherein the 5'-wing, gap, and 3' wing are independently selected from among those discussed above. For example, in certain embodiments, a gapmer has a 5'-wing, a gap, and a 3'-wing having features selected from among any of those listed in the tables above and any 5'-wing may be paired with any gap and any 3'-wing. For example, in certain embodiments, a 5'-wing may comprise AAABB, a 3'-wing may comprise BBA, and the gap may comprise DDDDDDD. For example, in certain embodiments, a gapmer has a 5'-wing, a gap, and a 3'-wing having features selected from among those listed in the following non-limiting table, wherein each motif is represented as (5'-wing)-(gap)-(3'-wing), wherein each number represents the number of linked nucleosides in each portion of the motif, for example, a 5-10-5 motif would have a 5'-wing comprising 5 nucleosides, a gap comprising 10 nucleosides, and a 3'-wing comprising 5 nucleosides:

TABLE 5

Certain Gapmer Sugar Motifs
Certain Gapmer Sugar Motifs

| | | | |
|---|---|---|---|
| 2-10-2 | 3-10-2 | 4-10-2 | 5-10-2 |
| 2-10-3 | 3-10-3 | 4-10-3 | 5-10-3 |
| 2-10-4 | 3-10-4 | 4-10-4 | 5-10-4 |
| 2-10-5 | 3-10-5 | 4-10-5 | 5-10-5 |
| 2-9-2 | 3-9-2 | 4-9-2 | 5-9-2 |
| 2-9-3 | 3-9-3 | 4-9-3 | 5-9-3 |
| 2-9-4 | 3-9-4 | 4-9-4 | 5-9-4 |
| 2-9-5 | 3-9-5 | 4-9-5 | 5-9-5 |
| 2-11-2 | 3-11-2 | 4-11-2 | 5-11-2 |
| 2-11-3 | 3-11-3 | 4-11-3 | 5-11-3 |
| 2-11-4 | 3-11-4 | 4-11-4 | 5-11-4 |
| 2-11-5 | 3-11-5 | 4-11-5 | 5-11-5 |
| 2-8-2 | 3-8-2 | 4-8-2 | 5-8-2 |
| 2-8-3 | 3-8-3 | 4-8-3 | 5-8-3 |
| 2-8-4 | 3-8-4 | 4-8-4 | 5-8-4 |
| 2-8-5 | 3-8-5 | 4-8-5 | 5-8-5 |

In certain embodiments, a gapmer comprises a 5'-wing, a gap, and a 3' wing, wherein the 5'-wing, gap, and 3' wing are independently selected from among those discussed above. For example, in certain embodiments, a gapmer has a 5'-wing, a gap, and a 3'-wing having features selected from among those listed in the following non-limiting tables:

TABLE 6

Certain Gapmer Nucleoside Motifs

| 5'-wing region | Central gap region | 3'-wing region |
|---|---|---|
| ADDA | DDDDDD | ABB |
| ABBA | DDDADDDD | ABAA |
| AAAAAAA | DDDDDDDDDD | AAA |
| AAAAABB | DDDDDDD | BBAAAAA |
| ABB | DDDDADDDD | ABB |
| ABB | DDDDBDDDD | BBA |
| ABB | DDDDDDDDD | BBA |
| AABAA | DDDDDDDD | AABAA |
| ABB | DDDDDD | AABAA |
| AAABAA | DDDDDDDD | AAABAA |
| AAABAA | DDDDDDDD | AAB |
| ABAB | DDDDDDDD | ABAB |
| AAABB | DDDDDDD | BBA |
| ABADB | DDDDDDD | BBA |
| ABA | DBDDDDDD | BBA |

TABLE 6-continued

Certain Gapmer Nucleoside Motifs

| 5'-wing region | Central gap region | 3'-wing region |
|---|---|---|
| ABA | DADDDDDD | BBA |
| ABAB | DDDDDDDD | BBA |
| AA | DDDDDDDD | BBBBBBBB |
| ABB | DDDDDD | ABADB |
| AAAAB | DDDDDDD | BAAAA |
| ABBB | DDDDDDDD | AB |
| AB | DDDDDDDD | BBBA |
| ABBB | DDDDDDDD | BBBA |
| AB | DDDDDDDD | ABA |
| ABB | DDDDWDDDD | BBA |
| AAABB | DDDWDDD | BBAAA |
| ABB | DDDDWWDDD | BBA |
| ABADB | DDDDDDD | BBA |
| ABBDC | DDDDDDD | BBA |
| ABBDDC | DDDDDD | BBA |
| ABBDCC | DDDDDD | BBA |
| ABB | DWWDWWDWW | BBA |
| ABB | DWDDDDDDD | BBA |
| ABB | DDWDDDDDD | BBA |
| ABB | DWWDDDDDD | BBA |
| AAABB | DDWDDDDDD | AA |
| BB | DDWDWDDDD | BBABBBB |
| ABB | DDDD($^N$D)DDDD | BBA |
| AAABB | DDD($^N$D)DDD | BBAAA |
| ABB | DDDD($^N$D)($^N$D)DDD | BBA |
| ABB | D($^N$D)($^N$D)D($^N$D)($^N$D)D($^N$D)($^N$D) | BBA |
| ABB | D($^N$D)DDDDDDD | BBA |
| ABB | DD($^N$D)DDDDDD | BBA |
| ABB | D($^N$D)($^N$D)DDDDDD | BBA |
| AAABB | DD($^N$D)DDDDDD | AA |
| BB | DD($^N$D)D($^N$D)DDDD | BBABBBB |
| ABAB | DDDDDDDD | BABA |

TABLE 7

Certain Gapmer Nucleoside Motifs

| 5'-wing region | Central gap region | 3'-wing region |
|---|---|---|
| ABBW | DDDDDDDD | BBA |
| ABB | DWDDDDDDD | BBA |
| ABB | DDWDDDDDD | BBA |
| ABB | DDDWDDDDD | BBA |
| ABB | DDDDWDDDD | BBA |
| ABB | DDDDDWDDD | BBA |
| ABB | DDDDDDWDD | BBA |
| ABB | DDDDDDDWD | BBA |
| ABB | DDDDDDD | WBBA |
| ABBWW | DDDDDDD | BBA |
| ABB | DWWDDDDDD | BBA |
| ABB | DDWWDDDDD | BBA |
| ABB | DDDWWDDDD | BBA |
| ABB | DDDDWWDDD | BBA |
| ABB | DDDDDWWDD | BBA |
| ABB | DDDDDDWWD | BBA |
| ABB | DDDDDDD | WWBBA |
| ABBW | DDDDDDD | WBBA |
| ABBW | DDDDDDWD | BBA |
| ABBW | DDDDDWDD | BBA |
| ABBW | DDDDWDDD | BBA |
| ABBW | DDDWDDDD | BBA |
| ABBW | DDWDDDDD | BBA |
| ABBW | DWDDDDDD | BBA |
| ABB | DWDDDDDD | WBBA |
| ABB | DWDDDDWD | BBA |
| ABB | DWDDDWDD | BBA |
| ABB | DWDDWDDD | BBA |
| ABB | DWDDWDDD | BBA |
| ABB | DWDWDDDD | BBA |
| ABB | DDWDDDDD | WBBA |
| ABB | DDWDDDWD | BBA |
| ABB | DDWDDDWDD | BBA |
| ABB | DDWDDWDDD | BBA |

TABLE 7-continued

Certain Gapmer Nucleoside Motifs

| 5'-wing region | Central gap region | 3'-wing region |
|---|---|---|
| ABB | DDWDWDDDD | BBA |
| ABB | DDWWDDDDD | BBA |
| ABB | DDDWDDDD | WBBA |
| ABB | DDDWDDDWD | BBA |
| ABB | DDDWDDWDD | BBA |
| ABB | DDDWDWDDD | BBA |
| ABB | DDDWWDDDD | BBA |
| ABB | DDDDWDDD | WBBA |
| ABB | DDDDWDDWD | BBA |
| ABB | DDDDWDWDD | BBA |
| ABB | DDDDWWDDD | BBA |
| ABB | DDDDDWDD | WBBA |
| ABB | DDDDDWDWD | BBA |
| ABB | DDDDDWWDD | BBA |
| ABB | DDDDDDWD | WBBA |

TABLE 8

Certain Gapmer Nucleoside Motifs

| 5'-wing region | Central gap region | 3'-wing region |
|---|---|---|
| ABBB | DDDDDDDD | BBA |
| ABB | DBDDDDDD | BBA |
| ABB | DDBDDDDD | BBA |
| ABB | DDDBDDDD | BBA |
| ABB | DDDDBDDD | BBA |
| ABB | DDDDDBDD | BBA |
| ABB | DDDDDDBD | BBA |
| ABB | DDDDDDBD | BBA |
| ABB | DDDDDDD | BBBA |
| ABBBB | DDDDDDD | BBA |
| ABB | DBBDDDDD | BBA |
| ABB | DDBBDDDD | BBA |
| ABB | DDDBBDDD | BBA |
| ABB | DDDDBBDD | BBA |
| ABB | DDDDDBBD | BBA |
| ABB | DDDDDDBD | BBA |
| ABB | DDDDDDD | BBBBA |
| ABBB | DDDDDDD | BBBA |
| ABB | DDDDDDBD | BBA |
| ABBB | DDDDDDBD | BBA |
| ABBB | DDDDBDDD | BBA |
| ABBB | DDDBDDDD | BBA |
| ABBB | DDBDDDDD | BBA |
| ABBB | DBDDDDDD | BBA |
| ABB | DBDDDDDD | BBBA |
| ABB | DBDDDDBD | BBA |
| ABB | DBDDDBDD | BBA |
| ABB | DBDDBDDD | BBA |
| ABB | DBDBDDDD | BBA |
| ABB | DBBDDDDD | BBA |
| ABB | DDBDDDDD | BBBA |
| ABB | DDBDDDBD | BBA |
| ABB | DDBDDBDD | BBA |
| ABB | DDBDBDDD | BBA |
| ABB | DDBBDDDD | BBA |
| ABB | DDDBDDDD | BBBA |
| ABB | DDDBDDBD | BBA |
| ABB | DDDBDBDD | BBA |
| ABB | DDDBBDDD | BBA |
| ABB | DDDDBDDD | BBBA |
| ABB | DDDDBDBD | BBA |
| ABB | DDDDBBDD | BBA |
| ABB | DDDDDBDD | BBBA |
| ABB | DDDDDBBD | BBA |
| ABB | DDDDDDBD | BBBA |

TABLE 9

Certain Gapmer Nucleoside Motifs

| 5'-wing region | Central gap region | 3'-wing region |
|---|---|---|
| ABB | DDDDDDDD | BBA |
| AB | DBDDDDDDD | BBA |
| AB | DDBDDDDDD | BBA |
| AB | DDDBDDDDD | BBA |
| AB | DDDDBDDDD | BBA |
| AB | DDDDDBDDD | BBA |
| AB | DDDDDDBDD | BBA |
| AB | DDDDDDDBD | BBA |
| AB | DDDDDDDDD | BBBA |
| ABBB | DDDDDDDD | BBA |
| AB | DBBDDDDDD | BBA |
| AB | DDBBDDDDD | BBA |
| AB | DDDBBDDDD | BBA |
| AB | DDDDBBDDD | BBA |
| AB | DDDDDBBDD | BBA |
| AB | DDDDDDBBD | BBA |
| AB | DDDDDDDBBD | BBA |
| AB | DDDDDDDD | BBBBA |
| ABBBB | DDDDDDD | BBA |
| AB | DBBBDDDDD | BBA |
| AB | DDBBBDDDD | BBA |
| AB | DDDBBBDDD | BBA |
| AB | DDDDBBBDD | BBA |
| AB | DDDDDBBBD | BBA |
| AB | DDDDDDBBBD | BBA |
| AB | DDDDDDD | BBBBBA |
| AB | DDDDDDDD | BBBA |
| AB | DDDDDDDBD | BBBA |
| AB | DDDDDBDD | BBBA |
| AB | DDDDBDDD | BBBA |
| AB | DDDBDDDD | BBBA |
| AB | DDBDDDDD | BBBA |
| AB | DBDDDDDD | BBBA |
| AB | DDDDDBD | BBBBA |
| AB | DDDDBDD | BBBBA |
| AB | DDDBDDD | BBBBA |
| AB | DDBDDDD | BBBBA |
| AB | DBDDDDD | BBBBA |
| AB | DDDDBD | BBBBBA |
| AB | DDDBDD | BBBBBA |
| AB | DDBDDD | BBBBBA |
| AB | DBDDDD | BBBBBA |

TABLE 10

Certain Gapmer Nucleoside Motifs

| 5'-wing region | Central gap region | 3'-wing region |
|---|---|---|
| AAAAAA | DDDDDDD | BABA |
| AAAAAB | DDDDDDD | BABA |
| AAAABA | DDDDDDD | BABA |
| AAABAA | DDDDDDD | BABA |
| AABAAA | DDDDDDD | BABA |
| ABAAAA | DDDDDDD | BABA |
| BAAAAA | DDDDDDD | BABA |
| ABAAAB | DDDDDDD | BABA |
| ABAABA | DDDDDDD | BABA |
| ABABAA | DDDDDDD | BABA |
| ABBAAA | DDDDDDD | BABA |
| AABAAB | DDDDDDD | BABA |
| AABABA | DDDDDDD | BABA |
| AABBAA | DDDDDDD | BABA |
| AAABAB | DDDDDDD | BABA |
| AAABBA | DDDDDDD | BABA |
| AAAABB | DDDDDDD | BABA |
| BAAAAB | DDDDDDD | BABA |
| BAAABA | DDDDDDD | BABA |
| BAABAA | DDDDDDD | BABA |
| BABAAA | DDDDDDD | BABA |
| BBAAAA | DDDDDDD | BABA |
| BBBAAA | DDDDDDD | BABA |
| BBABAA | DDDDDDD | BABA |
| BBAABA | DDDDDDD | BABA |
| BBAAAB | DDDDDDD | BABA |
| ABABAB | DDDDDDD | BABA |
| BBBBAA | DDDDDDD | BABA |
| BBBABA | DDDDDDD | BABA |
| BBBAAB | DDDDDDD | BABA |
| BBBBBA | DDDDDDD | BABA |
| BBBBAB | DDDDDDD | BABA |
| AAABBB | DDDDDDD | BABA |
| AABABB | DDDDDDD | BABA |
| ABAABB | DDDDDDD | BABA |
| BAAABB | DDDDDDD | BABA |
| AABBBB | DDDDDDD | BABA |
| ABABBB | DDDDDDD | BABA |
| BAABBB | DDDDDDD | BABA |
| ABBBBB | DDDDDDD | BABA |
| BABBBB | DDDDDDD | BABA |
| BBBBBB | DDDDDDD | BABA |

TABLE 11

Certain Gapmer Nucleoside Motifs

| 5'-wing region | Central gap region | 3'-wing region |
|---|---|---|
| AAAAA | DDDDDDD | AAAAA |
| AAAAB | DDDDDDD | AAAAA |
| AAABA | DDDDDDD | AAAAA |
| AAABB | DDDDDDD | AAAAA |
| AABAA | DDDDDDD | AAAAA |
| AABAB | DDDDDDD | AAAAA |
| AABBA | DDDDDDD | AAAAA |
| AABBB | DDDDDDD | AAAAA |
| ABAAA | DDDDDDD | AAAAA |
| ABAAB | DDDDDDD | AAAAA |
| ABABA | DDDDDDD | AAAAA |
| ABABB | DDDDDDD | AAAAA |
| ABBAA | DDDDDDD | AAAAA |
| ABBAB | DDDDDDD | AAAAA |
| ABBBA | DDDDDDD | AAAAA |
| ABBBB | DDDDDDD | AAAAA |
| BAAAA | DDDDDDD | AAAAA |
| BAAAB | DDDDDDD | AAAAA |
| BAABA | DDDDDDD | AAAAA |
| BAABB | DDDDDDD | AAAAA |
| BABAA | DDDDDDD | AAAAA |
| BABAB | DDDDDDD | AAAAA |
| BABBA | DDDDDDD | AAAAA |
| BABBB | DDDDDDD | AAAAA |
| BBAAA | DDDDDDD | AAAAA |
| BBAAB | DDDDDDD | AAAAA |
| BBABA | DDDDDDD | AAAAA |
| BBABB | DDDDDDD | AAAAA |
| BBBAA | DDDDDDD | AAAAA |
| BBBAB | DDDDDDD | AAAAA |
| BBBBA | DDDDDDD | AAAAA |
| BBBBB | DDDDDDD | AAAAA |
| AAAAA | DDDDDDD | BAAAA |
| AAAAB | DDDDDDD | BAAAA |
| AAABA | DDDDDDD | BAAAA |
| AAABB | DDDDDDD | BAAAA |
| AABAA | DDDDDDD | BAAAA |
| AABAB | DDDDDDD | BAAAA |
| AABBA | DDDDDDD | BAAAA |
| AABBB | DDDDDDD | BAAAA |
| ABAAA | DDDDDDD | BAAAA |
| ABAAB | DDDDDDD | BAAAA |
| ABABA | DDDDDDD | BAAAA |
| ABABB | DDDDDDD | BAAAA |
| ABBAA | DDDDDDD | BAAAA |
| ABBAB | DDDDDDD | BAAAA |
| ABBBA | DDDDDDD | BAAAA |

TABLE 11-continued

Certain Gapmer Nucleoside Motifs

| 5'-wing region | Central gap region | 3'-wing region |
|---|---|---|
| ABBBB | DDDDDDD | BAAAA |
| BAAAA | DDDDDDD | BAAAA |
| BAAAB | DDDDDDD | BAAAA |
| BAABA | DDDDDDD | BAAAA |
| BAABB | DDDDDDD | BAAAA |
| BABAA | DDDDDDD | BAAAA |
| BABAB | DDDDDDD | BAAAA |
| BABBA | DDDDDDD | BAAAA |
| BABBB | DDDDDDD | BAAAA |
| BBAAA | DDDDDDD | BAAAA |
| BBAAB | DDDDDDD | BAAAA |
| BBABA | DDDDDDD | BAAAA |
| BBABB | DDDDDDD | BAAAA |
| BBBAA | DDDDDDD | BAAAA |
| BBBAB | DDDDDDD | BAAAA |
| BBBBA | DDDDDDD | BAAAA |
| BBBBB | DDDDDDD | BAAAA |
| AAAAA | DDDDDDD | BBAAA |
| AAAAB | DDDDDDD | BBAAA |
| AAABA | DDDDDDD | BBAAA |
| AAABB | DDDDDDD | BBAAA |
| AABAA | DDDDDDD | BBAAA |
| AABAB | DDDDDDD | BBAAA |
| AABBA | DDDDDDD | BBAAA |
| AABBB | DDDDDDD | BBAAA |
| ABAAA | DDDDDDD | BBAAA |
| ABAAB | DDDDDDD | BBAAA |
| ABABA | DDDDDDD | BBAAA |
| ABABB | DDDDDDD | BBAAA |
| ABBAA | DDDDDDD | BBAAA |
| ABBAB | DDDDDDD | BBAAA |
| ABBBA | DDDDDDD | BBAAA |
| ABBBB | DDDDDDD | BBAAA |
| BAAAA | DDDDDDD | BBAAA |
| BAAAB | DDDDDDD | BBAAA |
| BAABA | DDDDDDD | BBAAA |
| BAABB | DDDDDDD | BBAAA |
| BABAA | DDDDDDD | BBAAA |
| BABAB | DDDDDDD | BBAAA |
| BABBA | DDDDDDD | BBAAA |
| BABBB | DDDDDDD | BBAAA |
| BBAAA | DDDDDDD | BBAAA |
| BBAAB | DDDDDDD | BBAAA |
| BBABA | DDDDDDD | BBAAA |
| BBABB | DDDDDDD | BBAAA |
| BBBAA | DDDDDDD | BBAAA |
| BBBAB | DDDDDDD | BBAAA |
| BBBBA | DDDDDDD | BBAAA |
| BBBBB | DDDDDDD | BBAAA |
| AAAAA | DDDDDDD | BBBAA |
| AAAAB | DDDDDDD | BBBAA |
| AAABA | DDDDDDD | BBBAA |
| AAABB | DDDDDDD | BBBAA |
| AABAA | DDDDDDD | BBBAA |
| AABAB | DDDDDDD | BBBAA |
| AABBA | DDDDDDD | BBBAA |
| AABBB | DDDDDDD | BBBAA |
| ABAAA | DDDDDDD | BBBAA |
| ABAAB | DDDDDDD | BBBAA |
| ABABA | DDDDDDD | BBBAA |
| ABABB | DDDDDDD | BBBAA |
| ABBAA | DDDDDDD | BBBAA |
| ABBAB | DDDDDDD | BBBAA |
| ABBBA | DDDDDDD | BBBAA |
| ABBBB | DDDDDDD | BBBAA |
| BAAAA | DDDDDDD | BBBAA |
| BAAAB | DDDDDDD | BBBAA |
| BAABA | DDDDDDD | BBBAA |
| BAABB | DDDDDDD | BBBAA |
| BABAA | DDDDDDD | BBBAA |
| BABAB | DDDDDDD | BBBAA |
| BABBA | DDDDDDD | BBBAA |
| BABBB | DDDDDDD | BBBAA |
| BBAAA | DDDDDDD | BBBAA |
| BBAAB | DDDDDDD | BBBAA |
| BBABA | DDDDDDD | BBBAA |
| BBABB | DDDDDDD | BBBAA |
| BBBAA | DDDDDDD | BBBAA |
| BBBAB | DDDDDDD | BBBAA |
| BBBBA | DDDDDDD | BBBAA |
| BBBBB | DDDDDDD | BBBAA |
| AAAAA | DDDDDDD | BBBBA |
| AAAAB | DDDDDDD | BBBBA |
| AAABA | DDDDDDD | BBBBA |
| AAABB | DDDDDDD | BBBBA |
| AABAA | DDDDDDD | BBBBA |
| AABAB | DDDDDDD | BBBBA |
| AABBA | DDDDDDD | BBBBA |
| AABBB | DDDDDDD | BBBBA |
| ABAAA | DDDDDDD | BBBBA |
| ABAAB | DDDDDDD | BBBBA |
| ABABA | DDDDDDD | BBBBA |
| ABABB | DDDDDDD | BBBBA |
| ABBAA | DDDDDDD | BBBBA |
| ABBAB | DDDDDDD | BBBBA |
| ABBBA | DDDDDDD | BBBBA |
| ABBBB | DDDDDDD | BBBBA |
| BAAAA | DDDDDDD | BBBBA |
| BAAAB | DDDDDDD | BBBBA |
| BAABA | DDDDDDD | BBBBA |
| BAABB | DDDDDDD | BBBBA |
| BABAA | DDDDDDD | BBBBA |
| BABAB | DDDDDDD | BBBBA |
| BABBA | DDDDDDD | BBBBA |
| BABBB | DDDDDDD | BBBBA |
| BBAAA | DDDDDDD | BBBBA |
| BBAAB | DDDDDDD | BBBBA |
| BBABA | DDDDDDD | BBBBA |
| BBABB | DDDDDDD | BBBBA |
| BBBAA | DDDDDDD | BBBBA |
| BBBAB | DDDDDDD | BBBBA |
| BBBBA | DDDDDDD | BBBBA |
| BBBBB | DDDDDDD | BBBBA |
| AAAAA | DDDDDDD | BBBBB |
| AAAAB | DDDDDDD | BBBBB |
| AAABA | DDDDDDD | BBBBB |
| AAABB | DDDDDDD | BBBBB |
| AABAA | DDDDDDD | BBBBB |
| AABAB | DDDDDDD | BBBBB |
| AABBA | DDDDDDD | BBBBB |
| AABBB | DDDDDDD | BBBBB |
| ABAAA | DDDDDDD | BBBBB |
| ABAAB | DDDDDDD | BBBBB |
| ABABA | DDDDDDD | BBBBB |
| ABABB | DDDDDDD | BBBBB |
| ABBAA | DDDDDDD | BBBBB |
| ABBAB | DDDDDDD | BBBBB |
| ABBBA | DDDDDDD | BBBBB |
| ABBBB | DDDDDDD | BBBBB |
| BAAAA | DDDDDDD | BBBBB |
| BAAAB | DDDDDDD | BBBBB |
| BAABA | DDDDDDD | BBBBB |
| BAABB | DDDDDDD | BBBBB |
| BABAA | DDDDDDD | BBBBB |
| BABAB | DDDDDDD | BBBBB |
| BABBA | DDDDDDD | BBBBB |
| BABBB | DDDDDDD | BBBBB |
| BBAAA | DDDDDDD | BBBBB |
| BBAAB | DDDDDDD | BBBBB |
| BBABA | DDDDDDD | BBBBB |
| BBABB | DDDDDDD | BBBBB |
| BBBAA | DDDDDDD | BBBBB |
| BBBAB | DDDDDDD | BBBBB |
| BBBBA | DDDDDDD | BBBBB |
| BBBBB | DDDDDDD | BBBBB |

TABLE 12

Certain Gapmer Nucleoside Motifs

| 5'-wing region | Central gap region | 3'-wing region |
|---|---|---|
| AAAW | DDDDDDD | BBA |
| AABW | DDDDDDD | BBA |
| ABAW | DDDDDDD | BBA |
| ABBW | DDDDDDD | BBA |
| BAAW | DDDDDDD | BBA |
| BABW | DDDDDDD | BBA |
| BBAW | DDDDDDD | BBA |
| BBBW | DDDDDDD | BBA |
| ABB | DDDDDDD | WAAA |
| ABB | DDDDDDD | WAAB |
| ABB | DDDDDDD | WABA |
| ABB | DDDDDDD | WABB |
| ABB | DDDDDDD | WBAA |
| ABB | DDDDDDD | WBAB |
| ABB | DDDDDDD | WBBA |
| ABB | DDDDDDD | WBBB |
| AAAWW | DDDDDD | BBA |
| AABWW | DDDDDD | BBA |
| ABAWW | DDDDDD | BBA |
| ABBWW | DDDDDD | BBA |
| BAAWW | DDDDDD | BBA |
| BABWW | DDDDDD | BBA |
| BBAWW | DDDDDD | BBA |
| BBBWW | DDDDDD | BBA |
| ABB | DDDDDD | WWAAA |
| ABB | DDDDDD | WWAAB |
| ABB | DDDDDD | WWABA |
| ABB | DDDDDD | WWABB |
| ABB | DDDDDD | WWBAA |
| ABB | DDDDDD | WWBAB |
| ABB | DDDDDD | WWBBA |
| ABB | DDDDDD | WWBBB |
| AAAAW | DDDDDDD | BBA |
| AAABW | DDDDDDD | BBA |
| AABAW | DDDDDDD | BBA |
| AABBW | DDDDDDD | BBA |
| ABAAW | DDDDDDD | BBA |
| ABABW | DDDDDDD | BBA |
| ABBAW | DDDDDDD | BBA |
| ABBBW | DDDDDDD | BBA |
| BAAAW | DDDDDDD | BBA |
| BAABW | DDDDDDD | BBA |
| BABAW | DDDDDDD | BBA |
| BABBW | DDDDDDD | BBA |
| BBAAW | DDDDDDD | BBA |
| BBABW | DDDDDDD | BBA |
| BBBAW | DDDDDDD | BBA |
| BBBBW | DDDDDDD | WAAAA |
| ABB | DDDDDDD | WAAAB |
| ABB | DDDDDDD | WAABA |
| ABB | DDDDDDD | WAABB |
| ABB | DDDDDDD | WABAA |
| ABB | DDDDDDD | WABAB |
| ABB | DDDDDDD | WABBA |
| ABB | DDDDDDD | WABBB |
| ABB | DDDDDDD | WBAAA |
| ABB | DDDDDDD | WBAAB |
| ABB | DDDDDDD | WBABA |
| ABB | DDDDDDD | WBABB |
| ABB | DDDDDDD | WBBAA |
| ABB | DDDDDDD | WBBAB |
| ABB | DDDDDDD | WBBBA |
| ABB | DDDDDDD | WBBBB | wherein each A is a modified nucleoside of a first type, each B is a modified nucleoside of a second type and each W is a modified nucleoside or nucleobase of either the first type, the second type or a third type, each D is a nucleoside comprising an unmodified 2'deoxy sugar moiety and unmodified nucleobase, and $^ND$ is modified nucleoside comprising a modified nucleobase and an unmodified 2'deoxy sugar moiety.

In certain embodiments, each A comprises a modified sugar moiety. In certain embodiments, each A comprises a 2'-substituted sugar moiety. In certain embodiments, each A comprises a 2'-substituted sugar moiety selected from among F, ara-F, $OCH_3$ and $O(CH_2)_2$—$OCH_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A comprises a modified nucleobase. In certain embodiments, each A comprises a modified nucleobase selected from among 2-thio-thymidine nucleoside and 5-propyne uridine nucleoside. In certain embodiments, each A comprises an HNA. In certain embodiments, each A comprises an F-HNA. In certain embodiments, each A comprises a 5'-substituted sugar moiety selected from among 5'-Me, and 5'-(R)-Me.

In certain embodiments, each B comprises a modified sugar moiety. In certain embodiments, each B comprises a 2'-substituted sugar moiety. In certain embodiments, each B comprises a 2'-substituted sugar moiety selected from among F, (ara)-F, $OCH_3$ and $O(CH_2)_2$—$OCH_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B comprises a modified nucleobase. In certain embodiments, each B comprises a modified nucleobase selected from among 2-thio-thymidine nucleoside and 5-propyne urindine nucleoside. In certain embodiments, each B comprises an HNA. In certain embodiments, each B comprises an F-HNA. In certain embodiments, each B comprises a 5'-substituted sugar moiety selected from among 5'-Me, and 5'-(R)-Me.

In certain embodiments, each C comprises a modified sugar moiety. In certain embodiments, each C comprises a 2'-substituted sugar moiety. In certain embodiments, each C comprises a 2'-substituted sugar moiety selected from among F, (ara)-F, $OCH_3$ and $O(CH_2)_2$—$OCH_3$. In certain embodiments, each C comprises a 5'-substituted sugar moiety. In certain embodiments, each C comprises a 5'-substituted sugar moiety selected from among 5'-Me, and 5'-(R)-Me. In certain embodiments, each C comprises a bicyclic sugar moiety. In certain embodiments, each C comprises a bicyclic sugar moiety selected from among cEt, cMOE, LNA, α-L-LNA, ENA and 2'-thio LNA. In certain embodiments, each C comprises a modified nucleobase. In certain embodiments, each C comprises a modified nucleobase selected from among 2-thio-thymidine and 5-propyne uridine. In certain embodiments, each C comprises a 2-thio-thymidine nucleoside. In certain embodiments, each C comprises an HNA. In certain embodiments, each C comprises an F-HNA.

In certain embodiments, each W comprises a modified sugar moiety. In certain embodiments, each W comprises a 2'-substituted sugar moiety. In certain embodiments, each W comprises a 2'-substituted sugar moiety selected from among F, (ara)-F, $OCH_3$ and $O(CH_2)_2$—$OCH_3$. In certain embodiments, each W comprises a 5'-substituted sugar moiety. In certain embodiments, each W comprises a 5'-substituted sugar moiety selected from among 5'-Me, and 5'-(R)-Me. In certain embodiments, each W comprises a bicyclic sugar moiety. In certain embodiments, each W comprises a bicyclic sugar moiety selected from among cEt, cMOE, LNA, α-L-LNA, ENA and 2'-thio LNA. In certain embodiments, each W comprises a sugar surrogate. In certain embodiments, each W comprises a sugar surrogate selected from among HNA and F-HNA. In certain embodiments, each W comprises a 2-thio-thymidine nucleoside.

In certain embodiments, at least one of A or B comprises a bicyclic sugar moiety, and the other comprises a 2'-substituted sugar moiety. In certain embodiments, one of A or B is an LNA nucleoside and the other of A or B comprises a 2'-substituted sugar moiety. In certain embodiments, one of A or B is a cEt nucleoside and the other of A or B comprises a 2'-substituted sugar moiety. In certain embodiments, one of A or B is an α-L-LNA nucleoside and the other of A or B comprises a 2'-substituted sugar moiety. In certain embodiments, one of A or B is an LNA nucleoside and the other of A or B comprises a 2'-MOE sugar moiety. In certain embodiments, one of A or B is a cEt nucleoside and the other of A or B comprises a 2'-MOE sugar moiety. In certain embodiments, one of A or B is an α-L-LNA nucleoside and the other of A or B comprises a 2'-MOE sugar moiety. In certain embodiments, one of A or B is an LNA nucleoside and the other of A or B comprises a 2'-F sugar moiety. In certain embodiments, one of A or B is a cEt nucleoside and the other of A or B comprises a 2'-F sugar moiety. In certain embodiments, one of A or B is an α-L-LNA nucleoside and the other of A or B comprises a 2'-F sugar moiety. In certain embodiments, one of A or B is an LNA nucleoside and the other of A or B comprises a 2'-(ara)-F sugar moiety. In certain embodiments, one of A or B is a cEt nucleoside and the other of A or B comprises a 2'-(ara)-F sugar moiety. In certain embodiments, one of A or B is an α-L-LNA nucleoside and the other of A or B comprises a 2'-(ara)-F sugar moiety.

In certain embodiments, A comprises a bicyclic sugar moiety, and B comprises a 2'-substituted sugar moiety. In certain embodiments, A is an LNA nucleoside and B comprises a 2'-substituted sugar moiety. In certain embodiments, A is a cEt nucleoside and B comprises a 2'-substituted sugar moiety. In certain embodiments, A is an α-L-LNA nucleoside and B comprises a 2'-substituted sugar moiety.

In certain embodiments, A comprises a bicyclic sugar moiety, and B comprises a 2'-MOE sugar moiety. In certain embodiments, A is an LNA nucleoside and B comprises a 2'-MOE sugar moiety. In certain embodiments, A is a cEt nucleoside and B comprises a 2'-MOE sugar moiety. In certain embodiments, A is an α-L-LNA nucleoside and B comprises a 2'-MOE sugar moiety.

In certain embodiments, A comprises a bicyclic sugar moiety, and B comprises a 2'-F sugar moiety. In certain embodiments, A is an LNA nucleoside and B comprises a 2'-F sugar moiety. In certain embodiments, A is a cEt nucleoside and B comprises a 2'-F sugar moiety. In certain embodiments, A is an α-L-LNA nucleoside and B comprises a 2'-F sugar moiety.

In certain embodiments, A comprises a bicyclic sugar moiety, and B comprises a 2'-(ara)-F sugar moiety. In certain embodiments, A is an LNA nucleoside and B comprises a 2'-(ara)-F sugar moiety. In certain embodiments, A is a cEt nucleoside and B comprises a 2'-(ara)-F sugar moiety. In certain embodiments, A is an α-L-LNA nucleoside and B comprises a 2'-(ara)-F sugar moiety.

In certain embodiments, B comprises a bicyclic sugar moiety, and A comprises a 2'-MOE sugar moiety. In certain embodiments, B is an LNA nucleoside and A comprises a 2'-MOE sugar moiety. In certain embodiments, B is a cEt nucleoside and A comprises a 2'-MOE sugar moiety. In certain embodiments, B is an α-L-LNA nucleoside and A comprises a 2'-MOE sugar moiety.

In certain embodiments, B comprises a bicyclic sugar moiety, and A comprises a 2'-F sugar moiety. In certain embodiments, B is an LNA nucleoside and A comprises a 2'-F sugar moiety. In certain embodiments, B is a cEt nucleoside and A comprises a 2'-F sugar moiety. In certain embodiments, B is an α-L-LNA nucleoside and A comprises a 2'-F sugar moiety.

In certain embodiments, B comprises a bicyclic sugar moiety, and A comprises a 2'-(ara)-F sugar moiety. In certain embodiments, B is an LNA nucleoside and A comprises a 2'-(ara)-F sugar moiety. In certain embodiments, B is a cEt nucleoside and A comprises a 2'-(ara)-F sugar moiety. In certain embodiments, B is an α-L-LNA nucleoside and A comprises a 2'-(ara)-F sugar moiety.

In certain embodiments, at least one of A or B comprises a bicyclic sugar moiety, another of A or B comprises a 2'-substituted sugar moiety and W comprises a modified nucleobase. In certain embodiments, one of A or B is an LNA nucleoside, another of A or B comprises a 2'-substituted sugar moiety, and W comprises a modified nucleobase. In certain embodiments, one of A or B is a cEt nucleoside, another of A or B comprises a 2'-substituted sugar moiety, and C comprises a modified nucleobase. In certain embodiments, one of A or B is an α-L-LNA nucleoside, another of A or B comprises a 2'-substituted sugar moiety, and W comprises a modified nucleobase.

In certain embodiments, one of A or B comprises a bicyclic sugar moiety, another of A or B comprises a 2'-MOE sugar moiety, and W comprises a modified nucleobase. In certain embodiments, one of A or B is an LNA nucleoside, another of A or B comprises a 2'-MOE sugar moiety, and W comprises a modified nucleobase. In certain embodiments, one of A or B is a cEt nucleoside, another of A or B comprises a 2'-MOE sugar moiety, and W comprises a modified nucleobase. In certain embodiments, one of A or B is an α-L-LNA nucleoside, another of A or B comprises a 2'-MOE sugar moiety, and W comprises a modified nucleobase.

In certain embodiments, one of A or B comprises a bicyclic sugar moiety, another of A or B comprises a 2'-F sugar moiety, and W comprises a modified nucleobase. In certain embodiments, one of A or B is an LNA nucleoside, another of A or B comprises a 2'-F sugar moiety, and W comprises a modified nucleobase. In certain embodiments, one of A or B is a cEt nucleoside, another of A or B comprises a 2'-F sugar moiety, and W comprises a modified nucleobase. In certain embodiments, one of A or B is an α-L-LNA nucleoside, another of A or B comprises a 2'-F sugar moiety, and W comprises a modified nucleobase.

In certain embodiments, one of A or B comprises a bicyclic sugar moiety, another of A or B comprises a 2'-(ara)-F sugar moiety, and W comprises a modified nucleobase. In certain embodiments, one of A or B is an LNA nucleoside, another of A or B comprises a 2'-(ara)-F sugar moiety, and W comprises a modified nucleobase. In certain embodiments, one of A or B is a cEt nucleoside, another of A or B comprises a 2'-(ara)-F sugar moiety, and W comprises a modified nucleobase. In certain embodiments, one of A or B is an α-L-LNA nucleoside, another of A or B comprises a 2'-(ara)-F sugar moiety, and W comprises a modified nucleobase.

In certain embodiments, one of A or B comprises a bicyclic sugar moiety, another of A or B comprises a 2'-substituted sugar moiety, and W comprises a 2-thio-thymidine nucleobase. In certain embodiments, one of A or B is an LNA nucleoside, another of A or B comprises a 2'-substituted sugar moiety, and W comprises a 2-thio-thymidine nucleobase. In certain embodiments, one of A or B is a cEt nucleoside, another of A or B comprises a 2'-substituted sugar moiety, and W comprises a 2-thio-thymidine nucleobase. In certain embodiments, one of A or B is an α-L-LNA nucleoside, another of A or B comprises a 2'-substituted sugar moiety, and W comprises a 2-thio-thymidine nucleobase.

In certain embodiments, one of A or B comprises a bicyclic sugar moiety, another of A or B comprises a 2'-MOE sugar moiety, and W comprises a 2-thio-thymidine nucleobase. In certain embodiments, one of A or B is an LNA nucleoside, another of A or B comprises a 2'-MOE sugar moiety, and W comprises a 2-thio-thymidine nucleobase. In certain embodiments, one of A or B is a cEt nucleoside, another of A or B comprises a 2'-MOE sugar moiety, and W comprises a 2-thio-thymidine nucleobase. In certain embodiments, one of A or B is an α-L-LNA nucleoside, another of A or B comprises a 2'-MOE sugar moiety, and W comprises a 2-thio-thymidine nucleobase.

In certain embodiments, one of A or B comprises a bicyclic sugar moiety, another of A or B comprises a 2'-F sugar moiety, and W comprises a 2-thio-thymidine nucleobase. In certain embodiments, one of A or B is an LNA nucleoside, another of A or B comprises a 2'-F sugar moiety, and W comprises a 2-thio-thymidine nucleobase. In certain embodiments, one of A or B is a cEt nucleoside, another of A or B comprises a 2'-F sugar moiety, and W comprises a 2-thio-thymidine nucleobase. In certain embodiments, one of A or B is an α-L-LNA nucleoside, another of A or B comprises a 2'-F sugar moiety, and W comprises a 2-thio-thymidine nucleobase.

In certain embodiments, one of A or B comprises a bicyclic sugar moiety, another of A or B comprises a 2'-(ara)-F sugar moiety, and W comprises a 2-thio-thymidine nucleobase. In certain embodiments, one of A or B is an LNA nucleoside, another of A or B comprises a 2'-(ara)-F sugar moiety, and W comprises a 2-thio-thymidine nucleobase. In certain embodiments, one of A or B is a cEt nucleoside, another of A or B comprises a 2'-(ara)-F sugar moiety, and W comprises a 2-thio-thymidine nucleobase. In certain embodiments, one of A or B is an α-L-LNA nucleoside, another of A or B comprises a 2'-(ara)-F sugar moiety, and W comprises 2-thio-thymidine nucleobase.

In certain embodiments, one of A or B comprises a bicyclic sugar moiety, another of A or B comprises a 2'-MOE sugar moiety, and W comprises a 5-propyne uridine nucleobase. In certain embodiments, one of A or B is an LNA nucleoside, another of A or B comprises a 2'-MOE sugar moiety, and C comprises a 5-propyne uridine nucleobase. In certain embodiments, one of A or B is a cEt nucleoside, another of A or B comprises a 2'-MOE sugar moiety, and W comprises a 5-propyne uridine nucleobase. In certain embodiments, one of A or B is an α-L-LNA nucleoside, another of A or B comprises a 2'-MOE sugar moiety, and C comprises a 5-propyne uridine nucleobase.

In certain embodiments, one of A or B comprises a bicyclic sugar moiety, another of A or B comprises a 2'-F sugar moiety, and W comprises a 5-propyne uridine nucleobase. In certain embodiments, one of A or B is an LNA nucleoside, another of A or B comprises a 2'-F sugar moiety, and C comprises a 5-propyne uridine nucleobase. In certain embodiments, one of A or B is a cEt nucleoside, another of A or B comprises a 2'-F sugar moiety, and W comprises a 5-propyne uridine nucleobase. In certain embodiments, one of A or B is an α-L-LNA nucleoside, another of A or B comprises a 2'-F sugar moiety, and W comprises a 5-propyne uridine nucleobase.

In certain embodiments, one of A or B comprises a bicyclic sugar moiety, another of A or B comprises a 2'-(ara)-F sugar moiety, and W comprises a 5-propyne uridine nucleobase. In certain embodiments, one of A or B is an LNA nucleoside, another of A or B comprises a 2'-(ara)-F sugar moiety, and W comprises a 5-propyne uridine nucleobase. In certain embodiments, one of A or B is a cEt nucleoside, another of A or B comprises a 2'-(ara)-F sugar moiety, and W comprises a 5-propyne uridine nucleobase. In certain embodiments, one of A or B is an α-L-LNA nucleoside, another of A or B comprises a 2'-(ara)-F sugar moiety, and W comprises a 5-propyne uridine nucleobase.

In certain embodiments, one of A or B comprises a bicyclic sugar moiety, another of A or B comprises a 2'-MOE sugar moiety, and W comprises a sugar surrogate. In certain embodiments, one of A or B is an LNA nucleoside, another of A or B comprises a 2'-MOE sugar moiety, and W comprises a sugar surrogate. In certain embodiments, one of A or B is a cEt nucleoside, another of A or B comprises a 2'-MOE sugar moiety, and W comprises a sugar surrogate. In certain embodiments, one of A or B is an α-L-LNA nucleoside, another of A or B comprises a 2'-MOE sugar moiety, and W comprises a sugar surrogate.

In certain embodiments, one of A or B comprises a bicyclic sugar moiety, another of A or B comprises a 2'-F sugar moiety, and W comprises a sugar surrogate. In certain embodiments, one of A or B is an LNA nucleoside, another of A or B comprises a 2'-F sugar moiety, and W comprises a sugar surrogate. In certain embodiments, one of A or B is a cEt nucleoside, another of A or B comprises a 2'-F sugar moiety, and W comprises a sugar surrogate. In certain embodiments, one of A or B is an α-L-LNA nucleoside, another of A or B comprises a 2'-F sugar moiety, and W comprises a sugar surrogate.

In certain embodiments, one of A or B comprises a bicyclic sugar moiety, another of A or B comprises a 2'-(ara)-F sugar moiety, and W comprises a sugar surrogate. In certain embodiments, one of A or B is an LNA nucleoside, another of A or B comprises a 2'-(ara)-F sugar moiety, and W comprises a sugar surrogate. In certain embodiments, one of A or B is a cEt nucleoside, another of A or B comprises a 2'-(ara)-F sugar moiety, and W comprises a sugar surrogate. In certain embodiments, one of A or B is an α-L-LNA nucleoside, another of A or B comprises a 2'-(ara)-F sugar moiety, and W comprises sugar surrogate.

In certain embodiments, one of A or B comprises a bicyclic sugar moiety, another of A or B comprises a 2'-MOE sugar moiety, and W comprises a HNA sugar surrogate. In certain embodiments, one of A or B is an LNA nucleoside, another of A or B comprises a 2'-MOE sugar moiety, and W comprises a HNA sugar surrogate. In certain embodiments, one of A or B is a cEt nucleoside, another of A or B comprises a 2'-MOE sugar moiety, and W comprises a HNA sugar surrogate. In certain embodiments, one of A or B is an α-L-LNA nucleoside, another of A or B comprises a 2'-MOE sugar moiety, and W comprises a HNA sugar surrogate.

In certain embodiments, one of A or B comprises a bicyclic sugar moiety, another of A or B comprises a 2'-F sugar moiety, and W comprises a HNA sugar surrogate. In certain embodiments, one of A or B is an LNA nucleoside, another of A or B comprises a 2'-F sugar moiety, and W comprises a HNA sugar surrogate. In certain embodiments, one of A or B is a cEt nucleoside, another of A or B comprises a 2'-F sugar moiety, and W comprises a HNA sugar surrogate. In certain embodiments, one of A or B is an α-L-LNA nucleoside, another of A or B comprises a 2'-F sugar moiety, and W comprises a sugar HNA surrogate.

In certain embodiments, one of A or B comprises a bicyclic sugar moiety, another of A or B comprises a 2'-(ara)-F sugar moiety, and W comprises a HNA sugar surrogate. In certain embodiments, one of A or B is an LNA nucleoside, another of A or B comprises a 2'-(ara)-F sugar moiety, and W comprises a HNA sugar surrogate. In certain embodiments, one of A or B is a cEt nucleoside, another of A or B comprises a 2'-(ara)-F sugar moiety, and W comprises a HNA sugar surrogate. In certain embodiments, one of A or B is an α-L-LNA nucleoside, another of A or B comprises a 2'-(ara)-F sugar moiety, and W comprises a HNA sugar surrogate.

In certain embodiments, one of A or B comprises a bicyclic sugar moiety, another of A or B comprises a 2'-MOE sugar moiety, and W comprises a F-HNA sugar surrogate. In certain embodiments, one of A or B is an LNA nucleoside, another of A or B comprises a 2'-MOE sugar moiety, and W comprises a F-HNA sugar surrogate. In certain embodiments, one of A or B is a cEt nucleoside, another of A or B comprises a 2'-MOE sugar moiety, and W comprises a F-HNA sugar surrogate. In certain embodiments, one of A or B is an α-L-LNA nucleoside, another of A or B comprises a 2'-MOE sugar moiety, and W comprises a F-HNA sugar surrogate.

In certain embodiments, one of A or B comprises a bicyclic sugar moiety, another of A or B comprises a 2'-F sugar moiety, and W comprises a F-HNA sugar surrogate. In certain embodiments, one of A or B is an LNA nucleoside, another of A or B comprises a 2'-F sugar moiety, and W comprises a F-HNA sugar surrogate. In certain embodiments, one of A or B is a cEt nucleoside, another of A or B comprises a 2'-F sugar moiety, and W comprises a F-HNA sugar surrogate. In certain embodiments, one of A or B is an α-L-LNA nucleoside, another of A or B comprises a 2'-F sugar moiety, and W comprises a F-HNA sugar surrogate.

In certain embodiments, one of A or B comprises a bicyclic sugar moiety, another of A or B comprises a 2'-(ara)-F sugar moiety, and W comprises a F-HNA sugar surrogate. In certain embodiments, one of A or B is an LNA nucleoside, another of A or B comprises a 2'-(ara)-F sugar moiety, and W comprises a F-HNA sugar surrogate. In certain embodiments, one of A or B is a cEt nucleoside, another of A or B comprises a 2'-(ara)-F sugar moiety, and W comprises a F-HNA sugar surrogate. In certain embodiments, one of A or B is an α-L-LNA nucleoside, another of A or B comprises a 2'-(ara)-F sugar moiety, and W comprises a F-HNA sugar surrogate.

In certain embodiments, one of A or B comprises a bicyclic sugar moiety, another of A or B comprises a 2'-MOE sugar moiety, and W comprises a 5'-Me DNA sugar moiety. In certain embodiments, one of A or B is an LNA nucleoside, another of A or B comprises a 2'-MOE sugar moiety, and W comprises a 5'-Me DNA sugar moiety. In certain embodiments, one of A or B is a cEt nucleoside, another of A or B comprises a 2'-MOE sugar moiety, and W comprises a 5'-Me DNA sugar moiety. In certain embodiments, one of A or B is an α-L-LNA nucleoside, another of A or B comprises a 2'-MOE sugar moiety, and W comprises a 5'-Me DNA sugar moiety.

In certain embodiments, one of A or B comprises a bicyclic sugar moiety, another of A or B comprises a 2'-F sugar moiety, and W comprises a 5'-Me DNA sugar moiety. In certain embodiments, one of A or B is an LNA nucleoside, another of A or B comprises a 2'-F sugar moiety, and W comprises a 5'-Me DNA sugar moiety. In certain embodiments, one of A or B is a cEt nucleoside, another of A or B comprises a 2'-F sugar moiety, and W comprises a 5'-Me DNA sugar moiety. In certain embodiments, one of A or B is an α-L-LNA nucleoside, another of A or B comprises a 2'-F sugar moiety, and W comprises a 5'-Me DNA sugar moiety.

In certain embodiments, one of A or B comprises a bicyclic sugar moiety, another of A or B comprises a 2'-(ara)-F sugar moiety, and W comprises a 5'-Me DNA sugar moiety. In certain embodiments, one of A or B is an LNA nucleoside, another of A or B comprises a 2'-(ara)-F sugar moiety, and W comprises a 5'-Me DNA sugar moiety. In certain embodiments, one of A or B is a cEt nucleoside, another of A or B comprises a 2'-(ara)-F sugar moiety, and W comprises a 5'-Me DNA sugar moiety. In certain embodiments, one of A or B is an α-L-LNA nucleoside, another of A or B comprises a 2'-(ara)-F sugar moiety, and W comprises a 5'-Me DNA sugar moiety.

In certain embodiments, one of A or B comprises a bicyclic sugar moiety, another of A or B comprises a 2'-MOE sugar moiety, and W comprises a 5'-(R)-Me DNA sugar moiety. In certain embodiments, one of A or B is an LNA nucleoside, another of A or B comprises a 2'-MOE sugar moiety, and W comprises a 5'-(R)-Me DNA sugar moiety. In certain embodiments, one of A or B is a cEt nucleoside, another of A or B comprises a 2'-MOE sugar moiety, and W comprises a 5'-(R)-Me DNA sugar moiety. In certain embodiments, one of A or B is an α-L-LNA nucleoside, another of A or B comprises a 2'-MOE sugar moiety, and W comprises a 5'-(R)-Me DNA sugar moiety.

In certain embodiments, one of A or B comprises a bicyclic sugar moiety, another of A or B comprises a 2'-F sugar moiety, and W comprises a 5'-(R)-Me DNA sugar moiety. In certain embodiments, one of A or B is an LNA nucleoside, another of A or B comprises a 2'-F sugar moiety, and W comprises a 5'-(R)-Me DNA sugar moiety. In certain embodiments, one of A or B is a cEt nucleoside, another of A or B comprises a 2'-F sugar moiety, and W comprises a 5'-(R)-Me DNA sugar moiety. In certain embodiments, one of A or B is an α-L-LNA nucleoside, another of A or B comprises a 2'-F sugar moiety, and W comprises a 5'-(R)-Me DNA sugar moiety.

In certain embodiments, one of A or B comprises a bicyclic sugar moiety, another of A or B comprises a 2'-(ara)-F sugar moiety, and W comprises a 5'-(R)-Me DNA sugar moiety. In certain embodiments, one of A or B is an LNA nucleoside, another of A or B comprises a 2'-(ara)-F sugar moiety, and W comprises a 5'-(R)-Me DNA sugar moiety. In certain embodiments, one of A or B is a cEt nucleoside, another of A or B comprises a 2'-(ara)-F sugar moiety, and W comprises a 5'-(R)-Me DNA sugar moiety. In certain embodiments, one of A or B is an α-L-LNA nucleoside, another of A or B comprises a 2'-(ara)-F sugar moiety, and W comprises a 5'-(R)-Me DNA sugar moiety.

In certain embodiments, at least two of A, B or W comprises a 2'-substituted sugar moiety, and the other comprises a bicyclic sugar moiety. In certain embodiments, at least two of A, B or W comprises a bicyclic sugar moiety, and the other comprises a 2'-substituted sugar moiety. In certain embodiments, a gapmer has a sugar motif other than: E-K-K-(D)$_9$-K-K-E; E-E-E-E-K-(D)$_9$-E-E-E-E-E; E-K-K-K-(D)$_9$-K-K-K-E; K-E-E-K-(D)$_9$-K-E-E-K; K-D-D-K-(D)$_9$-K-D-D-K; K-E-K-E-K-(D)$_9$-K-E-K-E-K; K-D-K-D-K-(D)$_9$-K-D-K-D-K; E-K-E-K-(D)$_9$-K-E-K-E; E-E-E-E-K-(D)$_8$-E-E-E-E-E; or E-K-E-K-E-(D)$_9$-E-K-E-K-E, E-E-E-K-K-(D)$_7$-E-E-K, E-K-E-K-K-(D)$_7$-K-E-K-E, E-K-E-K-E-K-(D)$_7$-K-E-K-E, wherein K is a nucleoside comprising a cEt sugar moiety and E is a nucleoside comprising a 2'-MOE sugar moiety.

In certain embodiments a gapmer comprises a A-(D)$_4$-A-(D)$_4$-A-(D)$_4$-AA motif. In certain embodiments a gapmer comprises a B-(D)$_4$-A-(D)$_4$-A-(D)$_4$-AA motif. In certain embodiments a gapmer comprises a A-(D)$_4$-B-(D)$_4$-A-

(D)₄-AA motif. In certain embodiments a gapmer comprises a A-(D)₄-A-(D)₄-B-(D)₄-AA motif. In certain embodiments a gapmer comprises a A-(D)₄-A-(D)₄-A-(D)₄-BA motif. In certain embodiments a gapmer comprises a A-(D)₄-A-(D)₄-A-(D)₄-BB motif. In certain embodiments a gapmer comprises a K-(D)₄-K-(D)₄-K-(D)₄-K-E motif.

viii. Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for nucleoside motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligonucleotides having a gapped internucleoside linkage motif may or may not have a gapped nucleoside motif and if it does have a gapped nucleoside motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosponate linkages. In certain embodiments, oligonucleotides having a gapmer nucleoside motif comprise a linkage motif comprising all phosphorothioate linkages except for one or two methylphosponate linkages. In certain embodiments, one methylphosponate linkage is in the central gap of an oligonucleotide having a gapmer nucleoside motif.

In certain embodiments, it is desirable to arrange the number of phosphorothioate internucleoside linkages and phosphodiester internucleoside linkages to maintain nuclease resistance. In certain embodiments, it is desirable to arrange the number and position of phosphorothioate internucleoside linkages and the number and position of phosphodiester internucleoside linkages to maintain nuclease resistance. In certain embodiments, the number of phosphorothioate internucleoside linkages may be decreased and the number of phosphodiester internucleoside linkages may be increased. In certain embodiments, the number of phosphorothioate internucleoside linkages may be decreased and the number of phosphodiester internucleoside linkages may be increased while still maintaining nuclease resistance. In certain embodiments it is desirable to decrease the number of phosphorothioate internucleoside linkages while retaining nuclease resistance. In certain embodiments it is desirable to increase the number of phosphodiester internucleoside linkages while retaining nuclease resistance.

ix. Certain Modification Motifs

Modification motifs define oligonucleotides by nucleoside motif (sugar motif and nucleobase motif) and linkage motif. For example, certain oligonucleotides have the following modification motif:

$A_sA_sA_sD_sD_sD_sD_s(^ND)_sD_sD_sD_sB_sB_sB$;

wherein each A is a modified nucleoside comprising a 2'-substituted sugar moiety; each D is an unmodified 2'-deoxynucleoside; each B is a modified nucleoside comprising a bicyclic sugar moiety; $^ND$ is a modified nucleoside comprising a modified nucleobase; and s is a phosphorothioate internucleoside linkage. Thus, the sugar motif is a gapmer motif. The nucleobase modification motif is a single modified nucleobase at 8th nucleoside from the 5'-end. Combining the sugar motif and the nucleobase modification motif, the nucleoside motif is an interrupted gapmer where the gap of the sugar modified gapmer is interrupted by a nucleoside comprising a modified nucleobase. The linkage motif is uniform phosphorothioate. The following non-limiting Table further illustrates certain modification motifs:

TABLE 13

Certain Modification Motifs

| 5'-wing region | Central gap region | 3'-wing region |
|---|---|---|
| $B_sB_s$ | $_sD_sD_sD_sD_sD_sD_sD_sD_s$ | $A_sA_sA_sA_sA_sA_sA_sA$ |
| AsBsBs | DsDsDsDsDsDsDsDs | BsBsA |
| AsBsBs | DsDsDsDs($^N$D)sDsDsDs | BsBsA |
| AsBsBs | DsDsDsDsAsDsDsDs | BsBsA |
| AsBsBs | DsDsDsDsBsDsDsDs | BsBsA |
| AsBsBs | DsDsDsDsWsDsDsDs | BsBsA |
| AsBsBsBs | DsDsDsDsDsDsDsDs | BsBsAsBsB |
| AsBsBs | DsDsDsDsDsDsDsDs | BsBsAsBsB |
| BsBsAsBsBs | DsDsDsDsDsDsDsDs | BsBsA |
| AsBsBs | DsDsDsDsDsDsDsDs | BsBsAsBsBsB |

TABLE 13-continued

Certain Modification Motifs

| 5'-wing region | Central gap region | 3'-wing region |
|---|---|---|
| AsAsBsAsAs | DsDsDsDsDsDsDsDs | BsBsA |
| AsAsAsBsAsAs | DsDsDsDsDsDsDs | BsBsA |
| AsAsBsAsAs | DsDsDsDsDsDsDsDs | AsAsBsAsA |
| AsAsBsAsAs | DsDsDsDsDsDsDs | AsAsBsAsAsA |
| AsAsAsAsBsAsAs | DsDsDsDsDsDsDs | BsBsA |
| AsBsAsBs | DsDsDsDsDsDsDsDs | BsAsBsA |
| AsBsAsBs | DsDsDsDsDsDsDsDs | AsAsBsAsAs |
| AsBsBs | DsDsDsDsDsDsDsDs | BsAsBsA |
| BsBsAsBsBsBsB | DsDsDsDsDsDsDsDs | BsBsA |
| AsAsAsAsAs | DsDsDsDsDsDsDsDs | AsAsAsAsA |
| AsAsAsAsAs | DsDsDsDsDsDs | AsAsAsAsA |
| AsAsAsAsAs | DsDsDsDsDsDsDs | BsBsAsBsBsBsB |
| AsAsBsAsAs | DsDsDsDsDsDs | BsBsA |
| AsBsAsBs | DsDsDsDsDsDsDs | BsBsA |
| AsBsAsBs | DsDsDsDsDsDs | AsAsAsBsBs |
| AsAsAsAsBs | DsDsDsDsDsDs | BsAsAsAsA |
| BsBs | DsDsDsDsDsDsDs | AsA |
| AsAs | DsDsDsDsDsDs | AsAsAsAsAsAsA |
| AsAsAs | DsDsDsDsDsDs | AsAsAsAsAsA |
| AsAsAs | DsDsDsDsDsDs | AsAsAsAsAsA |
| AsBs | DsDsDsDsDsDs | BsBsBsA |
| AsBsBsBs | DsDsDsDsDsDsDsDs | BsA |
| AsBs | DsDsDsDsDsDsDsDs | BsBsBsA |
| AsAsAsBsBs | DsDsDs($^N$D)sDsDs | BsBsAsAsA |
| AsAsAsBsBs | DsDsDsAsDsDsDs | BsBsAsAsA |
| AsAsAsBsBs | DsDsDsBsDsDsDs | BsBsAsAsA |
| AsAsAsAsBs | DsDsDsDsDsDsDs | BsAsAsAsA |
| AsAsBsBsBs | DsDsDsDsDsDs | BsBsBsAsA |
| AsAsAsAsAs | DsDsDsDsDsDs | AsAsAsAsAs |
| AsAsAsBs | DsDsDsDsDsDs | AsAsAsAsAs |
| AsAsBsBsBs | DsDsDsDsDsDs | AsAsAsAsAs |
| AsAsAsAsAs | DsDsDsDsDsDs | BsAsAsAsAs |
| AsAsAsAsAs | DsDsDsDsDsDs | BsBsAsAsAs |
| AsAsAsAsAs | DsDsDsDsDsDs | BsBsBsAsAs |
| AsBsBs | DsDsDsDs($^N$D)s($^N$D)sDsDsDs | BsBsA |
| AsBsBs | Ds($^N$D)s($^N$D)sDs($^N$D)s($^N$D)sDs($^N$D)s($^N$D)s | BsBsA |
| AsBsBs | Ds($^N$D)sDsDsDsDsDsDs | BsBsA |
| AsBsBs | DsDs($^N$D)sDsDsDsDsDs | BsBsA |
| AsBsBs | Ds($^N$D)sDsDsDsDsDsDs | BsBsA |
| AsBsBs | DsDs(D)zDsDsDsDsDs | BsBsA |
| AsBsBs | Ds(D)zDsDsDsDsDsDs | BsBsA |
| AsBsBs | (D)zDsDsDsDsDsDsDs | BsBsA |
| AsBsBs | DsDsAsDsDsDsDsDs | BsBsA |
| AsBsBs | DsDsBsDsDsDsDsDs | BsBsA |
| AsBsBs | AsDsDsDsDsDsDsDs | BsBsA |
| AsBsBs | BsDsDsDsDsDsDsDs | BsBsA |
| AsBsAsBs | DsDs(D)zDsDsDsDsDs | BsBsBsAsAs |
| AsAsAsBsBs | DsDs($^N$D)sDsDsDsDsDs | AsA |
| AsBsBsBs | Ds(D)zDsDsDsDsDsDs | AsAsAsBsBs |
| AsBsAsBs | DsDsDsDsDsDsDs(D)z | BsBsA |
| AsAsBsBsBs | DsDsDsAsDsDsDs | BsBsBsAsA |
| AsAsBsBsBs | DsDsBsDsDsDs | BsBsBsAsA |
| AsBsAsBs | DsDsDsAsDsDsDs | BsBsAsBsBsBsB |
| AsBsBsBs | DsDsDs(D)zDsDsDs | BsA |
| AsAsBsBsBs | DsDsAsAsDsDsDs | BsBsA |
| AsBsBs | DsDsDs(D)zDsDsDs | BsBsBsA |
| BsBs | DsDs($^N$D)sDs($^N$D)sDsDsDs | BsBsAsBsBsBsB | wherein each A and B are nucleosides comprising differently modified sugar moieties, each D is a nucleoside comprising an unmodified 2'deoxy sugar moiety, each W is a modified nucleoside of either the first type, the second type or a third type, each $^N$D is a modified nucleoside comprising a modified nucleobase, s is a phosphorothioate internucleoside linkage, and z is a non-phosphorothioate internucleoside linkage.

In certain embodiments, each A comprises a modified sugar moiety. In certain embodiments, each A comprises a 2'-substituted sugar moiety. In certain embodiments, each A comprises a 2'-substituted sugar moiety selected from among F, (ara)-F, OCH$_3$ and O(CH$_2$)$_2$—OCH$_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A comprises a modified nucleobase. In certain embodiments, each A comprises a modified nucleobase selected from among 2-thio-thymidine nucleoside and 5-propyne uridine nucleoside. In certain embodiments, each B comprises a modified sugar moiety. In certain embodiments, each B comprises a 2'-substituted sugar moiety. In certain embodiments, each B comprises a 2'-substituted sugar moiety selected from among F, (ara)-F, OCH$_3$ and O(CH$_2$)$_2$—OCH$_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B comprises a modified nucleobase. In certain embodiments, each B comprises a modified nucleobase selected from among 2-thio-thymidine nucleoside and 5-propyne urindine nucleoside. In certain embodiments, each A comprises an HNA. In certain embodiments, each A comprises an F-HNA.

In certain embodiments, each W comprises a modified sugar moiety. In certain embodiments, each W comprises a 2'-substituted sugar moiety. In certain embodiments, each W comprises a 2'-substituted sugar moiety selected from among F, (ara)-F, $OCH_3$ and $O(CH_2)_2$—$OCH_3$. In certain embodiments, each W comprises a 5'-substituted sugar moiety. In certain embodiments, each W comprises a 5'-substituted sugar moiety selected from among 5'-Me, and 5'-(R)-Me. In certain embodiments, each W comprises a bicyclic sugar moiety. In certain embodiments, each W comprises a bicyclic sugar moiety selected from among cEt, cMOE, LNA, α-L-LNA, ENA and 2'-thio LNA. In certain embodiments, each W comprises a sugar surrogate. In certain embodiments, each W comprises a sugar surrogate selected from among HNA and F-HNA.

In certain embodiments, at least one of A or B comprises a bicyclic sugar moiety, and the other comprises a 2'-substituted sugar moiety. In certain embodiments, one of A or B is an LNA nucleoside and the other of A or B comprises a 2'-substituted sugar moiety. In certain embodiments, one of A or B is a cEt nucleoside and the other of A or B comprises a 2'-substituted sugar moiety. In certain embodiments, one of A or B is an α-L-LNA nucleoside and the other of A or B comprises a 2'-substituted sugar moiety. In certain embodiments, one of A or B is an LNA nucleoside and the other of A or B comprises a 2'-MOE sugar moiety. In certain embodiments, one of A or B is a cEt nucleoside and the other of A or B comprises a 2'-MOE sugar moiety. In certain embodiments, one of A or B is an α-L-LNA nucleoside and the other of A or B comprises a 2'-MOE sugar moiety. In certain embodiments, one of A or B is an LNA nucleoside and the other of A or B comprises a 2'-F sugar moiety. In certain embodiments, one of A or B is a cEt nucleoside and the other of A or B comprises a 2'-F sugar moiety. In certain embodiments, one of A or B is an α-L-LNA nucleoside and the other of A or B comprises a 2'-F sugar moiety. In certain embodiments, one of A or B is an LNA nucleoside and the other of A or B comprises a 2'-(ara)-F sugar moiety. In certain embodiments, one of A or B is a cEt nucleoside and the other of A or B comprises a 2'-(ara)-F sugar moiety. In certain embodiments, one of A or B is an α-L-LNA nucleoside and the other of A or B comprises a 2'-(ara)-F sugar moiety.

In certain embodiments, A comprises a bicyclic sugar moiety, and B comprises a 2'-substituted sugar moiety. In certain embodiments, A is an LNA nucleoside and B comprises a 2'-substituted sugar moiety. In certain embodiments, A is a cEt nucleoside and B comprises a 2'-substituted sugar moiety. In certain embodiments, A is an α-L-LNA nucleoside and B comprises a 2'-substituted sugar moiety.

In certain embodiments, A comprises a bicyclic sugar moiety, and B comprises a 2'-MOE sugar moiety. In certain embodiments, A is an LNA nucleoside and B comprises a 2'-MOE sugar moiety. In certain embodiments, A is a cEt nucleoside and B comprises a 2'-MOE sugar moiety. In certain embodiments, A is an α-L-LNA nucleoside and B comprises a 2'-MOE sugar moiety.

In certain embodiments, A comprises a bicyclic sugar moiety, and B comprises a 2'-F sugar moiety. In certain embodiments, A is an LNA nucleoside and B comprises a 2'-F sugar moiety. In certain embodiments, A is a cEt nucleoside and B comprises a 2'-F sugar moiety. In certain embodiments, A is an α-L-LNA nucleoside and B comprises a 2'-F sugar moiety.

In certain embodiments, A comprises a bicyclic sugar moiety, and B comprises a 2'-(ara)-F sugar moiety. In certain embodiments, A is an LNA nucleoside and B comprises a 2'-(ara)-F sugar moiety. In certain embodiments, A is a cEt nucleoside and B comprises a 2'-(ara)-F sugar moiety. In certain embodiments, A is an α-L-LNA nucleoside and B comprises a 2'-(ara)-F sugar moiety.

In certain embodiments, B comprises a bicyclic sugar moiety, and A comprises a 2'-MOE sugar moiety. In certain embodiments, B is an LNA nucleoside and A comprises a 2'-MOE sugar moiety. In certain embodiments, B is a cEt nucleoside and A comprises a 2'-MOE sugar moiety. In certain embodiments, B is an α-L-LNA nucleoside and A comprises a 2'-MOE sugar moiety.

In certain embodiments, B comprises a bicyclic sugar moiety, and A comprises a 2'-F sugar moiety. In certain embodiments, B is an LNA nucleoside and A comprises a 2'-F sugar moiety. In certain embodiments, B is a cEt nucleoside and A comprises a 2'-F sugar moiety. In certain embodiments, B is an α-L-LNA nucleoside and A comprises a 2'-F sugar moiety.

In certain embodiments, B comprises a bicyclic sugar moiety, and A comprises a 2'-(ara)-F sugar moiety. In certain embodiments, B is an LNA nucleoside and A comprises a 2'-(ara)-F sugar moiety. In certain embodiments, B is a cEt nucleoside and A comprises a 2'-(ara)-F sugar moiety. In certain embodiments, B is an α-L-LNA nucleoside and A comprises a 2'-(ara)-F sugar moiety.

In certain embodiments, at least one of A or B comprises a bicyclic sugar moiety, another of A or B comprises a 2'-substituted sugar moiety and W comprises a modified nucleobase. In certain embodiments, one of A or B is an LNA nucleoside, another of A or B comprises a 2'-substituted sugar moiety, and W comprises a modified nucleobase. In certain embodiments, one of A or B is a cEt nucleoside, another of A or B comprises a 2'-substituted sugar moiety, and C comprises a modified nucleobase. In certain embodiments, one of A or B is an α-L-LNA nucleoside, another of A or B comprises a 2'-substituted sugar moiety, and W comprises a modified nucleobase.

In certain embodiments, one of A or B comprises a bicyclic sugar moiety, another of A or B comprises a 2'-MOE sugar moiety, and W comprises a modified nucleobase. In certain embodiments, one of A or B is an LNA nucleoside, another of A or B comprises a 2'-MOE sugar moiety, and W comprises a modified nucleobase. In certain embodiments, one of A or B is a cEt nucleoside, another of A or B comprises a 2'-MOE sugar moiety, and W comprises a modified nucleobase. In certain embodiments, one of A or B is an α-L-LNA nucleoside, another of A or B comprises a 2'-MOE sugar moiety, and W comprises a modified nucleobase.

In certain embodiments, one of A or B comprises a bicyclic sugar moiety, another of A or B comprises a 2'-F sugar moiety, and W comprises a modified nucleobase. In certain embodiments, one of A or B is an LNA nucleoside, another of A or B comprises a 2'-F sugar moiety, and W comprises a modified nucleobase. In certain embodiments, one of A or B is a cEt nucleoside, another of A or B comprises a 2'-F sugar moiety, and W comprises a modified nucleobase. In certain embodiments, one of A or B is an α-L-LNA nucleoside, another of A or B comprises a 2'-F sugar moiety, and W comprises a modified nucleobase.

In certain embodiments, one of A or B comprises a bicyclic sugar moiety, another of A or B comprises a 2'-(ara)-F sugar moiety, and W comprises a modified nucleobase. In certain embodiments, one of A or B is an LNA nucleoside, another of A or B comprises a 2'-(ara)-F sugar moiety, and W comprises a modified nucleobase. In certain embodiments, one of A or B is a cEt nucleoside, another of A or B comprises a 2'-(ara)-F sugar moiety, and W comprises a modified nucleobase. In certain embodiments, one of A or B is an α-L-LNA nucleoside, another of A or B comprises a 2'-(ara)-F sugar moiety, and W comprises a modified nucleobase.

In certain embodiments, one of A or B comprises a bicyclic sugar moiety, another of A or B comprises a 2'-substituted sugar moiety, and W comprises a 2-thio-thymidine nucleobase. In certain embodiments, one of A or B is an LNA nucleoside, another of A or B comprises a 2'-substituted sugar moiety, and W comprises a 2-thio-thymidine nucleobase. In certain embodiments, one of A or B is a cEt nucleoside, another of A or B comprises a 2'-substituted sugar moiety, and W comprises a 2-thio-thymidine nucleobase. In certain embodiments, one of A or B is an α-L-LNA nucleoside, another of A or B comprises a 2'-substituted sugar moiety, and W comprises a 2-thio-thymidine nucleobase.

In certain embodiments, one of A or B comprises a bicyclic sugar moiety, another of A or B comprises a 2'-MOE sugar moiety, and W comprises a 2-thio-thymidine nucleobase. In certain embodiments, one of A or B is an LNA nucleoside, another of A or B comprises a 2'-MOE sugar moiety, and W comprises a 2-thio-thymidine nucleobase. In certain embodiments, one of A or B is a cEt nucleoside, another of A or B comprises a 2'-MOE sugar moiety, and W comprises a 2-thio-thymidine nucleobase. In certain embodiments, one of A or B is an α-L-LNA nucleoside, another of A or B comprises a 2'-MOE sugar moiety, and W comprises a 2-thio-thymidine nucleobase.

In certain embodiments, one of A or B comprises a bicyclic sugar moiety, another of A or B comprises a 2'-F sugar moiety, and W comprises a 2-thio-thymidine nucleobase. In certain embodiments, one of A or B is an LNA nucleoside, another of A or B comprises a 2'-F sugar moiety, and W comprises a 2-thio-thymidine nucleobase. In certain embodiments, one of A or B is a cEt nucleoside, another of A or B comprises a 2'-F sugar moiety, and W comprises a 2-thio-thymidine nucleobase. In certain embodiments, one of A or B is an α-L-LNA nucleoside, another of A or B comprises a 2'-F sugar moiety, and W comprises a 2-thio-thymidine nucleobase.

In certain embodiments, one of A or B comprises a bicyclic sugar moiety, another of A or B comprises a 2'-(ara)-F sugar moiety, and W comprises a 2-thio-thymidine nucleobase. In certain embodiments, one of A or B is an LNA nucleoside, another of A or B comprises a 2'-(ara)-F sugar moiety, and W comprises a 2-thio-thymidine nucleobase. In certain embodiments, one of A or B is a cEt nucleoside, another of A or B comprises a 2'-(ara)-F sugar moiety, and W comprises a 2-thio-thymidine nucleobase. In certain embodiments, one of A or B is an α-L-LNA nucleoside, another of A or B comprises a 2'-(ara)-F sugar moiety, and W comprises 2-thio-thymidine nucleobase.

In certain embodiments, one of A or B comprises a bicyclic sugar moiety, another of A or B comprises a 2'-MOE sugar moiety, and W comprises a 5-propyne uridine nucleobase. In certain embodiments, one of A or B is an LNA nucleoside, another of A or B comprises a 2'-MOE sugar moiety, and C comprises a 5-propyne uridine nucleobase. In certain embodiments, one of A or B is a cEt nucleoside, another of A or B comprises a 2'-MOE sugar moiety, and W comprises a 5-propyne uridine nucleobase. In certain embodiments, one of A or B is an α-L-LNA nucleoside, another of A or B comprises a 2'-MOE sugar moiety, and C comprises a 5-propyne uridine nucleobase.

In certain embodiments, one of A or B comprises a bicyclic sugar moiety, another of A or B comprises a 2'-F sugar moiety, and W comprises a 5-propyne uridine nucleobase. In certain embodiments, one of A or B is an LNA nucleoside, another of A or B comprises a 2'-F sugar moiety, and C comprises a 5-propyne uridine nucleobase. In certain embodiments, one of A or B is a cEt nucleoside, another of A or B comprises a 2'-F sugar moiety, and W comprises a 5-propyne uridine nucleobase. In certain embodiments, one of A or B is an α-L-LNA nucleoside, another of A or B comprises a 2'-F sugar moiety, and W comprises a 5-propyne uridine nucleobase.

In certain embodiments, one of A or B comprises a bicyclic sugar moiety, another of A or B comprises a 2'-(ara)-F sugar moiety, and W comprises a 5-propyne uridine nucleobase. In certain embodiments, one of A or B is an LNA nucleoside, another of A or B comprises a 2'-(ara)-F sugar moiety, and W comprises a 5-propyne uridine nucleobase. In certain embodiments, one of A or B is a cEt nucleoside, another of A or B comprises a 2'-(ara)-F sugar moiety, and W comprises a 5-propyne uridine nucleobase. In certain embodiments, one of A or B is an α-L-LNA nucleoside, another of A or B comprises a 2'-(ara)-F sugar moiety, and W comprises a 5-propyne uridine nucleobase.

In certain embodiments, one of A or B comprises a bicyclic sugar moiety, another of A or B comprises a 2'-MOE sugar moiety, and W comprises a sugar surrogate. In certain embodiments, one of A or B is an LNA nucleoside, another of A or B comprises a 2'-MOE sugar moiety, and W comprises a sugar surrogate. In certain embodiments, one of A or B is a cEt nucleoside, another of A or B comprises a 2'-MOE sugar moiety, and W comprises a sugar surrogate. In certain embodiments, one of A or B is an α-L-LNA nucleoside, another of A or B comprises a 2'-MOE sugar moiety, and W comprises a sugar surrogate.

In certain embodiments, one of A or B comprises a bicyclic sugar moiety, another of A or B comprises a 2'-F sugar moiety, and W comprises a sugar surrogate. In certain embodiments, one of A or B is an LNA nucleoside, another of A or B comprises a 2'-F sugar moiety, and W comprises a sugar surrogate. In certain embodiments, one of A or B is a cEt nucleoside, another of A or B comprises a 2'-F sugar moiety, and W comprises a sugar surrogate. In certain embodiments, one of A or B is an α-L-LNA nucleoside, another of A or B comprises a 2'-F sugar moiety, and W comprises a sugar surrogate.

In certain embodiments, one of A or B comprises a bicyclic sugar moiety, another of A or B comprises a 2'-(ara)-F sugar moiety, and W comprises a sugar surrogate. In certain embodiments, one of A or B is an LNA nucleoside, another of A or B comprises a 2'-(ara)-F sugar moiety, and W comprises a sugar surrogate. In certain embodiments, one of A or B is a cEt nucleoside, another of A or B comprises a 2'-(ara)-F sugar moiety, and W comprises a sugar surrogate. In certain embodiments, one of A or B is an α-L-LNA nucleoside, another of A or B comprises a 2'-(ara)-F sugar moiety, and W comprises sugar surrogate.

In certain embodiments, one of A or B comprises a bicyclic sugar moiety, another of A or B comprises a 2'-MOE sugar moiety, and W comprises a HNA sugar surrogate. In certain embodiments, one of A or B is an LNA nucleoside, another of A or B comprises a 2'-MOE sugar moiety, and W comprises a HNA sugar surrogate. In certain embodiments, one of A or B is a cEt nucleoside, another of A or B comprises a 2'-MOE sugar moiety, and W comprises a HNA sugar surrogate. In certain embodiments, one of A or B is an α-L-LNA nucleoside, another of A or B comprises a 2'-MOE sugar moiety, and W comprises a HNA sugar surrogate.

In certain embodiments, one of A or B comprises a bicyclic sugar moiety, another of A or B comprises a 2'-F sugar moiety, and W comprises a HNA sugar surrogate. In certain embodiments, one of A or B is an LNA nucleoside, another of A or B comprises a 2'-F sugar moiety, and W comprises a HNA sugar surrogate. In certain embodiments, one of A or B is a cEt nucleoside, another of A or B comprises a 2'-F sugar moiety, and W comprises a HNA sugar surrogate. In certain embodiments, one of A or B is an α-L-LNA nucleoside, another of A or B comprises a 2'-F sugar moiety, and W comprises a sugar HNA surrogate.

In certain embodiments, one of A or B comprises a bicyclic sugar moiety, another of A or B comprises a 2'-(ara)-F sugar moiety, and W comprises a HNA sugar surrogate. In certain embodiments, one of A or B is an LNA nucleoside, another of A or B comprises a 2'-(ara)-F sugar moiety, and W comprises a HNA sugar surrogate. In certain embodiments, one of A or B is a cEt nucleoside, another of A or B comprises a 2'-(ara)-F sugar moiety, and W comprises a HNA sugar surrogate. In certain embodiments, one of A or B is an α-L-LNA nucleoside, another of A or B comprises a 2'-(ara)-F sugar moiety, and W comprises a HNA sugar surrogate.

In certain embodiments, one of A or B comprises a bicyclic sugar moiety, another of A or B comprises a 2'-MOE sugar moiety, and W comprises a F-HNA sugar surrogate. In certain embodiments, one of A or B is an LNA nucleoside, another of A or B comprises a 2'-MOE sugar moiety, and W comprises a F-HNA sugar surrogate. In certain embodiments, one of A or B is a cEt nucleoside, another of A or B comprises a 2'-MOE sugar moiety, and W comprises a F-HNA sugar surrogate. In certain embodiments, one of A or B is an α-L-LNA nucleoside, another of A or B comprises a 2'-MOE sugar moiety, and W comprises a F-HNA sugar surrogate.

In certain embodiments, one of A or B comprises a bicyclic sugar moiety, another of A or B comprises a 2'-F sugar moiety, and W comprises a F-HNA sugar surrogate. In certain embodiments, one of A or B is an LNA nucleoside, another of A or B comprises a 2'-F sugar moiety, and W comprises a F-HNA sugar surrogate. In certain embodiments, one of A or B is a cEt nucleoside, another of A or B comprises a 2'-F sugar moiety, and W comprises a F-HNA sugar surrogate. In certain embodiments, one of A or B is an α-L-LNA nucleoside, another of A or B comprises a 2'-F sugar moiety, and W comprises a F-HNA sugar surrogate.

In certain embodiments, one of A or B comprises a bicyclic sugar moiety, another of A or B comprises a 2'-(ara)-F sugar moiety, and W comprises a F-HNA sugar surrogate. In certain embodiments, one of A or B is an LNA nucleoside, another of A or B comprises a 2'-(ara)-F sugar moiety, and W comprises a F-HNA sugar surrogate. In certain embodiments, one of A or B is a cEt nucleoside, another of A or B comprises a 2'-(ara)-F sugar moiety, and W comprises a F-HNA sugar surrogate. In certain embodiments, one of A or B is an α-L-LNA nucleoside, another of A or B comprises a 2'-(ara)-F sugar moiety, and W comprises a F-HNA sugar surrogate.

In certain embodiments, one of A or B comprises a bicyclic sugar moiety, another of A or B comprises a 2'-MOE sugar moiety, and W comprises a 5'-Me DNA sugar moiety. In certain embodiments, one of A or B is an LNA nucleoside, another of A or B comprises a 2'-MOE sugar moiety, and W comprises a 5'-Me DNA sugar moiety. In certain embodiments, one of A or B is a cEt nucleoside, another of A or B comprises a 2'-MOE sugar moiety, and W comprises a 5'-Me DNA sugar moiety. In certain embodiments, one of A or B is an α-L-LNA nucleoside, another of A or B comprises a 2'-MOE sugar moiety, and W comprises a 5'-Me DNA sugar moiety.

In certain embodiments, one of A or B comprises a bicyclic sugar moiety, another of A or B comprises a 2'-F sugar moiety, and W comprises a 5'-Me DNA sugar moiety. In certain embodiments, one of A or B is an LNA nucleoside, another of A or B comprises a 2'-F sugar moiety, and W comprises a 5'-Me DNA sugar moiety. In certain embodiments, one of A or B is a cEt nucleoside, another of A or B comprises a 2'-F sugar moiety, and W comprises a 5'-Me DNA sugar moiety. In certain embodiments, one of A or B is an α-L-LNA nucleoside, another of A or B comprises a 2'-F sugar moiety, and W comprises a 5'-Me DNA sugar moiety.

In certain embodiments, one of A or B comprises a bicyclic sugar moiety, another of A or B comprises a 2'-(ara)-F sugar moiety, and W comprises a 5'-Me DNA sugar moiety. In certain embodiments, one of A or B is an LNA nucleoside, another of A or B comprises a 2'-(ara)-F sugar moiety, and W comprises a 5'-Me DNA sugar moiety. In certain embodiments, one of A or B is a cEt nucleoside, another of A or B comprises a 2'-(ara)-F sugar moiety, and W comprises a 5'-Me DNA sugar moiety. In certain embodiments, one of A or B is an α-L-LNA nucleoside, another of A or B comprises a 2'-(ara)-F sugar moiety, and W comprises a 5'-Me DNA sugar moiety.

In certain embodiments, one of A or B comprises a bicyclic sugar moiety, another of A or B comprises a 2'-MOE sugar moiety, and W comprises a 5'-(R)-Me DNA sugar moiety. In certain embodiments, one of A or B is an LNA nucleoside, another of A or B comprises a 2'-MOE sugar moiety, and W comprises a 5'-(R)-Me DNA sugar moiety. In certain embodiments, one of A or B is a cEt nucleoside, another of A or B comprises a 2'-MOE sugar moiety, and W comprises a 5'-(R)-Me DNA sugar moiety. In certain embodiments, one of A or B is an α-L-LNA nucleoside, another of A or B comprises a 2'-MOE sugar moiety, and W comprises a 5'-(R)-Me DNA sugar moiety.

In certain embodiments, one of A or B comprises a bicyclic sugar moiety, another of A or B comprises a 2'-F sugar moiety, and W comprises a 5'-(R)-Me DNA sugar moiety. In certain embodiments, one of A or B is an LNA nucleoside, another of A or B comprises a 2'-F sugar moiety, and W comprises a 5'-(R)-Me DNA sugar moiety. In certain embodiments, one of A or B is a cEt nucleoside, another of A or B comprises a 2'-F sugar moiety, and W comprises a 5'-(R)-Me DNA sugar moiety. In certain embodiments, one of A or B is an α-L-LNA nucleoside, another of A or B comprises a 2'-F sugar moiety, and W comprises a 5'-(R)-Me DNA sugar moiety.

In certain embodiments, one of A or B comprises a bicyclic sugar moiety, another of A or B comprises a 2'-(ara)-F sugar moiety, and W comprises a 5'-(R)-Me DNA sugar moiety. In certain embodiments, one of A or B is an LNA nucleoside, another of A or B comprises a 2'-(ara)-F sugar moiety, and W comprises a 5'-(R)-Me DNA sugar moiety. In certain embodiments, one of A or B is a cEt nucleoside, another of A or B comprises a 2'-(ara)-F sugar moiety, and W comprises a 5'-(R)-Me DNA sugar moiety. In certain embodiments, one of A or B is an α-L-LNA nucleoside, another of A or B comprises a 2'-(ara)-F sugar moiety, and W comprises a 5'-(R)-Me DNA sugar moiety.

In certain embodiments, at least two of A, B or W comprises a 2'-substituted sugar moiety, and the other comprises a bicyclic sugar moiety. In certain embodiments, at least two of A, B or W comprises a bicyclic sugar moiety, and the other comprises a 2'-substituted sugar moiety.

d. Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range.

e. Certain Oligonucleotides

In certain embodiments, oligonucleotides of the present invention are characterized by their modification motif and overall length. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create a variety of oligonucleotides. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

f. Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxy-cholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3'end of an oligomeric compound, but before one or more terminal group nucleosides. In certain embodiments, conjugate groups are placed within a terminal group.

In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the motifs discussed above. Thus, for example, an oligomeric compound comprising an oligonucleotide having region of alternating nucleosides may comprise a terminal group.

B. Antisense Compounds

In certain embodiments, oligomeric compounds provided herein are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

a. Certain Antisense Activities and Mechanisms

In certain antisense activities, hybridization of an antisense compound results in recruitment of a protein that cleaves of the target nucleic acid. For example, certain antisense compounds result in RNase H mediated cleavage of target nucleic acid. RNase H is a cellular endonuclease that cleaves the RNA strand of an RNA:DNA duplex. The "DNA" in such an RNA:DNA duplex, need not be unmodified DNA. In certain embodiments, the invention provides antisense compounds that are sufficiently "DNA-like" to elicit RNase H activity. Such DNA-like antisense compounds include, but are not limited to gapmers having unmodified deoxyfuronose sugar moieties in the nucleosides of the gap and modified sugar moieties in the nucleosides of the wings.

Antisense activities may be observed directly or indirectly. In certain embodiments, observation or detection of an antisense activity involves observation or detection of a change in an amount of a target nucleic acid or protein encoded by such target nucleic acid; a change in the ratio of splice variants of a nucleic acid or protein; and/or a phenotypic change in a cell or animal.

In certain embodiments, compounds comprising oligonucleotides having a gapmer nucleoside motif described herein have desirable properties compared to non-gapmer oligonucleotides or to gapmers having other motifs. In certain circumstances, it is desirable to identify motifs resulting in a favorable combination of potent antisense activity and relatively low toxicity. In certain embodiments, compounds of the present invention have a favorable therapeutic index (measure of activity divided by measure of toxicity).

a. Certain Selective Antisense Compounds

In certain embodiments, antisense compounds provided are selective for a target relative to a non-target nucleic acid. In certain embodiments, the nucleobase sequences of the target and non-target nucleic acids differ by no more than 4 differentiating nucleobases in the targeted region. In certain embodiments, the nucleobase sequences of the target and non-target nucleic acids differ by no more than 3 differentiating nucleobases in the targeted region. In certain embodiments, the nucleobase sequences of the target and non-target nucleic acids differ by no more than 2 differentiating nucleobases in the targeted region. In certain embodiments, the nucleobase sequences of the target and non-target nucleic acids differ by a single differentiating nucleobase in the targeted region. In certain embodiments, the target and non-target nucleic acids are transcripts from different genes. In certain embodiments, the target and non-target nucleic acids are different alleles for the same gene. In certain embodiments, the introduction of a mismatch between an antisense compound and a non-target nucleic acid may alter the RNase H cleavage site of a target nucleic acid compared to a non-target nucleic acid. In certain embodiments, the target and non-target nucleic acids are not functionally related to one another (e.g., are transcripts from different genes). In certain embodiments, the target and not-target nucleic acids are allelic variants of one another. In certain embodiments, the allelic variant contains a single nucleotide polymorphism (SNP). In certain embodiments, a SNP is associated with a mutant allele. In certain embodiments, a mutant SNP is associated with a disease. In certain embodiments a mutant SNP is associated with a disease, but is not causative of the disease. In certain embodiments, mRNA and protein expression of a mutant allele is associated with disease.

Selectivity of antisense compounds is achieved, principally, by nucleobase complementarity. For example, if an antisense compound has no mismatches for a target nucleic acid and one or more mismatches for a non-target nucleic acid, some amount of selectivity for the target nucleic acid will result. In certain embodiments, provided herein are antisense compounds with enhanced selectivity (i.e. the ratio of activity for the target to the activity for non-target is greater). For example, in certain embodiments, a selective nucleoside comprises a particular feature or combination of features (e.g., chemical modification, motif, placement of selective nucleoside, and/or self-complementary region) that increases selectivity of an antisense compound compared to an antisense compound not having that feature or combination of features. In certain embodiments, such feature or combination of features increases antisense activity for the target. In certain embodiments, such feature or combination of features decreases activity for the target, but decreases activity for the non-target by a greater amount, thus resulting in an increase in selectivity.

Without being limited by mechanism, enhanced selectivity may result from a larger difference in the affinity of an antisense compound for its target compared to its affinity for the non-target and/or a larger difference in RNase H activity for the resulting duplexes. For example, in certain embodiments, a selective antisense compound comprises a modified nucleoside at that same position as a differentiating nucleobase (i.e., the selective nucleoside is modified). That modification may increase the difference in binding affinity of the antisense compound for the target relative to the non-target. In addition or in the alternative, the chemical modification may increase the difference in RNAse H activity for the duplex formed by the antisense compound and its target compared to the RNase activity for the duplex formed by the antisense compound and the non-target. For example, the modification may exaggerate a structure that is less compatible for RNase H to bind, cleave and/or release the non-target.

In certain embodiments, an antisense compound binds its intended target to form a target duplex. In certain embodiments, RNase H cleaves the target nucleic acid of the target duplex. In certain such embodiments, there is a primary cleavage site between two particular nucleosides of the target nucleic acid (the primary target cleavage site), which accounts for the largest amount of cleavage of the target nucleic acid. In certain embodiments, there are one or more secondary target cleavage sites. In certain embodiments, the same antisense compound hybridizes to a non-target to form a non-target duplex. In certain such embodiments, the non-target differs from the target by a single nucleobase within the target region, and so the antisense compound hybridizes with a single mismatch. Because of the mismatch, in certain embodiments, RNase H cleavage of the non-target may be reduced compared to cleavage of the target, but still occurs. In certain embodiments, though, the primary site of that cleavage of the non-target nucleic acid (primary non-target cleavage site) is different from that of the target. That is; the primary site is shifted due to the mismatch. In such a circumstance, one may use a modification placed in the antisense compound to disrupt RNase H cleavage at the primary non-target cleavage site. Such modification will result in reduced cleavage of the non-target, but will result little or no decrease in cleavage of the target. In certain embodiments, the modification is a modified sugar, nucleobase and/or linkage.

In certain embodiments, the primary non-target cleavage site is towards the 5'-end of the antisense compound, and the 5'-end of an antisense compound may be modified to prevent RNaseH cleavage. In this manner, it is thought that one having skill in the art may modify the 5'-end of an antisense compound, or modify the nucleosides in the gap region of the 5'-end of the antisense compound, or modify the 3'-most 5'-region nucleosides of the antisense compound to selectively inhibit RNaseH cleavage of the non-target nucleic acid duplex while retaining RNase H cleavage of the target nucleic acid duplex. In certain embodiments, 1-3 of the 3'-most 5'-region nucleosides of the antisense compound comprises a bicyclic sugar moiety.

For example, in certain embodiments the target nucleic acid may have an allelic variant, e.g. a non-target nucleic acid, containing a single nucleotide polymorphism. An antisense compound may be designed having a single nucleobase mismatch from the non-target nucleic acid, but which has full complementarity to the target nucleic acid. The mismatch between the antisense compound and the non-target nucleic acid may destabilize the antisense compound non-target nucleic acid duplex, and consequently the cleavage site of RNaseH may shift upstream towards the 5'-end of the antisense compound. Modification of the 5'-end of the antisense compound or the gap region near the 5'-end of the antisense compound, or one or more of the 3'-most nucleosides of the 5'-wing region, will then prevent RNaseH cleavage of the non-target nucleic acid. Since the target nucleic acid is fully complementary to the antisense compound, the antisense compound and the target nucleic acid will form a more stabilized antisense compound-target nucleic acid duplex and the cleavage site of RnaseH will be more downstream, towards the 3' end of the antisense compound. Accordingly, modifications at the 5'-end of the antisense compound will prevent RNaseH cleavage of the non-target nucleic acid, but will not substantially effect RNaseH cleavage of the target nucleic acid, and selectivity between a target nucleic acid and its allelic variant may be achieved. In certain embodiments, one or more of the 3'-most nucleosides of the 5'-wing region comprises a bicyclic sugar moiety. In certain embodiments, one or more of the 3'-most nucleosides of the 5'-wing region comprises a bicyclic sugar moiety selected from cEt and LNA. In certain embodiments, one or more of the 3'-most nucleosides of the 5'-wing region comprises cEt. In certain embodiments, one or more of the 3'-most nucleosides of the 5'-wing region comprises LNA.

In certain embodiments, the introduction of a mismatch between an antisense compound and a target nucleic acid may alter the RNase H cleavage site of a target nucleic acid compared to a non-target nucleic acid by shifting the RNaseH cleavage site downstream from the mismatch site and towards the 3'-end of the antisense compound. In certain embodiments where the cleavage site of a target nucleic acid compared to a non-target nucleic acid has shifted downstream towards the 3'-end of the antisense compound, the 3'-end of an antisense compound may be modified to prevent RNaseH cleavage. In this manner, it is thought that one having skill in the art may modify the 3'-end of an antisense compound, or modify the nucleosides in the gap region near the 3'-end of antisense compound, to selectively inhibit RNaseH cleavage of the non-target nucleic acid while retaining RNase H cleavage of the target nucleic acid.

For example, in certain embodiments the target nucleic acid may have an allelic variant, e.g. a non-target nucleic acid, containing a single nucleotide polymorphism. An antisense compound may be designed having a single nucleobase mismatch from the non-target nucleic acid, but which has full complementarity to target nucleic acid. The mismatch between the antisense compound and the non-target nucleic acid may destabilize the antisense compound-non-target nucleic acid duplex, and consequently the cleavage site of RNaseH may shift downstream towards the 3'-end of the antisense compound. Modification of the 3'-end of the antisense compound, or one or more of the 5'-most nucleosides of the 3'-wing region, or the gap region of the antisense compound near the 3'-end will then prevent RNaseH cleavage of the non-target nucleic acid. Since the target nucleic acid is fully complementary to the antisense compound, the antisense compound and the target nucleic acid will form a more stabilized antisense compound-target nucleic acid duplex and the cleavage site of RnaseH will be more upstream, towards the 5' end of the antisense compound. Accordingly, modifications at the 3'-end of the antisense compound will prevent RNaseH cleavage of the non-target nucleic acid, but will not substantially effect RNaseH cleavage of the target nucleic acid, and selectivity between a target nucleic acid and its allelic variant may be achieved. In certain embodiments, one or more of the 5'-most nucleosides of the 3'-wing region comprises a bicyclic sugar moiety. In certain embodiments, one or more of the 5'-most nucleosides of the 3'-wing region comprises a bicyclic sugar moiety selected from cEt and LNA. In certain embodiments, one or more of the 5'-most nucleosides of the 3'-wing region comprises cEt. In certain embodiments, one or more of the 5'-most nucleosides of the 3'-wing region comprises LNA.

In certain embodiments, the selectivity of antisense compounds having certain gaps, e.g. gaps of 7 nucleosides or longer, may be improved by the addition of one or more bicyclic nucleosides at the 3'-most 5'-wing nucleoside. In certain embodiments, the selectivity of antisense compounds having certain gaps, e.g. gaps of 7 nucleosides or longer, may be improved by the addition of two or more bicyclic nucleosides at the 3'-most 5'-wing nucleoside. In certain embodiments, the selectivity of antisense compounds having certain gaps, e.g. gaps of 7 nucleosides or longer, may be improved by the addition of one bicyclic nucleoside at the 3'-most 5'-wing nucleoside. In certain embodiments, the selectivity of antisense compounds having certain gaps, e.g. gaps of 7 nucleosides or longer, may be improved by the addition of two bicyclic nucleosides at the 3'-most 5'-wing nucleoside. In certain embodiments, the selectivity of antisense compounds having certain gaps, e.g. gaps of 7 nucleosides or longer, may be improved by the addition of three bicyclic nucleosides at the 3'-most 5'-wing nucleoside. In certain embodiments, the selectivity of antisense compounds having certain gaps, e.g. gaps of 7 nucleosides or longer, may be improved by the addition of four bicyclic nucleosides at the 3'-most 5'-wing nucleoside. In certain embodiments, the selectivity of antisense compounds having certain gaps, e.g. gaps of 7 nucleosides or longer, may be improved by the addition of five bicyclic nucleosides at the 3'-most 5'-wing nucleoside. In certain embodiments discussed above, the bicyclic nucleosides at the 3'-most 5'-wing nucleoside are selected from among cEt, cMOE, LNA, α-LNA, ENA and 2'-thio LNA. In certain embodiments discussed above, the bicyclic nucleosides at the 3'-most 5'-wing nucleoside comprise cEt. In certain embodiments discussed above, the bicyclic nucleosides at the 3'-most 5'-wing nucleoside comprise LNA.

In certain embodiments, the selectivity of antisense compounds having certain gaps, e.g. gaps of 7 nucleosides or longer, may be improved by the addition of one or more bicyclic nucleosides at the 3'-most 5'-wing nucleoside and the addition of one or more bicylic nucleosides at the 5'-most 3'-wing nucleoside. In certain embodiments, the selectivity of antisense compounds having certain gaps, e.g. gaps of 7 nucleosides or longer, may be improved by the addition of two or more bicyclic nucleosides at the 3'-most 5'-wing nucleoside and the addition of one or more bicylic nucleosides at the 5'-most 3'-wing nucleoside. In certain embodiments, the selectivity of antisense compounds having certain gaps, e.g. gaps of 7 nucleosides or longer, may be improved by the addition of one bicyclic nucleoside at the 3'-most 5'-wing nucleoside and the addition of one or more bicylic nucleosides at the 5'-most 3'-wing nucleoside. In certain embodiments, the selectivity of antisense compounds having certain gaps, e.g. gaps of 7 nucleosides or longer, may be improved by the addition of two bicyclic nucleosides at the 3'-most 5'-wing nucleoside and the addition of one or more bicylic nucleosides at the 5'-most 3'-wing nucleoside. In certain embodiments, the selectivity of antisense compounds having certain gaps, e.g. gaps of 7 nucleosides or longer, may be improved by the addition of three bicyclic nucleosides at the 3'-most 5'-wing nucleoside and the addition of one or more bicylic nucleosides at the 5'-most 3'-wing nucleoside. In certain embodiments, the selectivity of antisense compounds having certain gaps, e.g. gaps of 7 nucleosides or longer, may be improved by the addition of four bicyclic nucleosides at the 3'-most 5'-wing nucleoside and the addition of one or more bicylic nucleosides at the 5'-most 3'-wing nucleoside. In certain embodiments, the selectivity of antisense compounds having certain gaps, e.g. gaps of 7 nucleosides or longer, may be improved by the addition of four bicyclic nucleosides at the 3'-most 5'-wing nucleoside and the addition of one or more bicylic nucleosides at the 5'-most 3'-wing nucleoside.

In certain embodiments, the selectivity of antisense compounds having certain gaps, e.g. gaps of 7 nucleosides or shorter, may be improved by the addition of one or more bicyclic nucleosides at the 3'-most 5'-wing nucleoside. In certain embodiments, the selectivity of antisense compounds having certain gaps, e.g. gaps of 7 nucleosides or shorter, may be improved by the addition of two or more bicyclic nucleosides at the 3'-most 5'-wing nucleoside. In certain embodiments, the selectivity of antisense compounds having certain gaps, e.g. gaps of 7 nucleosides or shorter, may be improved by the addition of one bicyclic nucleoside at the 3'-most 5'-wing nucleoside. In certain embodiments, the selectivity of antisense compounds having certain gaps, e.g. gaps of 7 nucleosides or shorter, may be improved by the addition of two bicyclic nucleosides at the 3'-most 5'-wing nucleoside. In certain embodiments, the selectivity of antisense compounds having certain gaps, e.g. gaps of 7 nucleosides or shorter, may be improved by the addition of three bicyclic nucleosides at the 3'-most 5'-wing nucleoside. In certain embodiments, the selectivity of antisense compounds having certain gaps, e.g. gaps of 7 nucleosides or shorter, may be improved by the addition of four bicyclic nucleosides at the 3'-most 5'-wing nucleoside. In certain embodiments, the selectivity of antisense compounds having certain gaps, e.g. gaps of 7 nucleosides or shorter, may be improved by the addition of five bicyclic nucleosides at the 3'-most 5'-wing nucleoside. In certain embodiments discussed above, the bicyclic nucleosides at the 3'-most 5'-wing nucleoside are selected from among cEt, cMOE, LNA, α-LNA, ENA and 2'-thio LNA. In certain embodiments discussed above, the bicyclic nucleosides at the 3'-most 5'-wing nucleoside comprise cEt. In certain embodiments discussed above, the bicyclic nucleosides at the 3'-most 5'-wing nucleoside comprise LNA.

Antisense compounds having certain specified motifs have enhanced selectivity, including, but not limited to motifs described above. In certain embodiments, enhanced selectivity is achieved by oligonucleotides comprising any one or more of:

a modification motif comprising a long 5'-wing (longer than 5, 6, or 7 nucleosides);

a modification motif comprising a long 3'-wing (longer than 5, 6, or 7 nucleosides);

a modification motif comprising a short gap region (shorter than 8, 7, or 6 nucleosides); and a modification motif comprising an interrupted gap region (having no uninterrupted stretch of unmodified 2'-deoxynucleosides longer than 7, 6 or 5).

i. Certain Selective Nucleobase Sequence Elements

In certain embodiments, selective antisense compounds comprise nucleobase sequence elements. Such nucleobase sequence elements are independent of modification motifs. Accordingly, oligonucleotides having any of the motifs (modification motifs, nucleoside motifs, sugar motifs, nucleobase modification motifs, and/or linkage motifs) may also comprise one or more of the following nucleobase sequence elements.

ii. Alignment of Differentiating Nucleobase/Target-Selective Nucleoside

In certain embodiments, a target region and a region of a non-target nucleic acid differ by 1-4 differentiating nucleobase. In such embodiments, selective antisense compounds have a nucleobase sequence that aligns with the non-target nucleic acid with 1-4 mismatches. A nucleoside of the antisense compound that corresponds to a differentiating nucleobase of the target nucleic acid is referred to herein as a target-selective nucleoside. In certain embodiments, selective antisense compounds having a gapmer motif align with a non-target nucleic acid, such that a target-selective nucleoside is positioned in the gap. In certain embodiments, a target-selective nucleoside is the $1^{st}$ nucleoside of the gap from the 5' end. In certain embodiments, a target-selective nucleoside is the $2^{nd}$ nucleoside of the gap from the 5' end. In certain embodiments, a target-selective nucleoside is the $3^{rd}$ nucleoside of the gap from the 5'-end. In certain embodiments, a target-selective nucleoside is the $4^{th}$ nucleoside of the gap from the 5'-end. In certain embodiments, a target-selective nucleoside is the $5^{th}$ nucleoside of the gap from the 5'-end. In certain embodiments, a target-selective nucleoside is the $6^{rd}$ nucleoside of the gap from the 5'-end. In certain embodiments, a target-selective nucleoside is the $8^{th}$ nucleoside of the gap from the 3'-end. In certain embodiments, a target-selective nucleoside is the $7^{th}$ nucleoside of the gap from the 3'-end. In certain embodiments, a target-selective nucleoside is the $6^{th}$ nucleoside of the gap from the 3'-end. In certain embodiments, a target-selective nucleoside is the $5^{th}$ nucleoside of the gap from the 3'-end. In certain embodiments, a target-selective nucleoside is the $4^{th}$ nucleoside of the gap from the 3'-end. In certain embodiments, a target-selective nucleoside is the $3^{rd}$ nucleoside of the gap from the 3'-end. In certain embodiments, a target-selective nucleoside is the $2^{nd}$ nucleoside of the gap from the 3'-end.

In certain embodiments, a target-selective nucleoside comprises a modified nucleoside. In certain embodiments, a target-selective nucleoside comprises a modified sugar. In certain embodiments, a target-selective nucleoside comprises a sugar surrogate. In certain embodiments, a target-selective nucleoside comprises a sugar surrogate selected from among HNA and F-HNA. In certain embodiments, a target-selective nucleoside comprises a 2'-substituted sugar moiety. In certain embodiments, a target-selective nucleoside comprises a 2'-substituted sugar moiety selected from among MOE, F and (ara)-F. In certain embodiments, a target-selective nucleoside comprises a 5'-substituted sugar moiety. In certain embodiments, a target-selective nucleoside comprises a 5'-substituted sugar moiety selected from 5'-(R)-Me DNA. In certain embodiments, a target-selective nucleoside comprises a bicyclic sugar moiety. In certain embodiments, a target-selective nucleoside comprises a bicyclic sugar moiety selected from among cEt, and α-L-LNA. In certain embodiments, a target-selective nucleoside comprises a modified nucleobase. In certain embodiments, a target-selective nucleoside comprises a modified nucleobase selected from among 2-thio-thymidine and 5-propyne uridine.

iii. Mismatches to the Target Nucleic Acid

In certain embodiments, selective antisense compounds comprise one or more mismatched nucleobases relative to the target nucleic acid. In certain such embodiments, antisense activity against the target is reduced by such mismatch, but activity against the non-target is reduced by a greater amount. Thus, in certain embodiments selectivity is improved. Any nucleobase other than the differentiating nucleobase is suitable for a mismatch. In certain embodiments, however, the mismatch is specifically positioned within the gap of an oligonucleotide having a gapmer motif. In certain embodiments, a mismatch relative to the target nucleic acid is at positions 1, 2, 3, 4, 5, 6, 7, or 8 from the 5'-end of the gap region. In certain embodiments, a mismatch relative to the target nucleic acid is at positions 9, 8, 7, 6, 5, 4, 3, 2, 1 of the antisense compounds from the 3'-end of the gap region. In certain embodiments, a mismatch relative to the target nucleid acid is at positions 1, 2, 3, or 4 of the antisense compounds from the 5'-end of the wing region. In certain embodiments, a mismatch relative to the target nucleid acid is at positions 4, 3, 2, or 1 of the antisense compounds from the 3'-end of the wing region.

iv. Self Complementary Regions

In certain embodiments, selective antisense compounds comprise a region that is not complementary to the target. In certain embodiments, such region is complementary to another region of the antisense compound. Such regions are referred to herein as self-complementary regions. For example, in certain embodiments, an antisense compound has a first region at one end that is complementary to a second region at the other end. In certain embodiments, one of the first and second regions is complementary to the target nucleic acid. Unless the target nucleic acid also includes a self-complementary region, the other of the first and second region of the antisense compound will not be complementary to the target nucleic acid. For illustrative purposes, certain antisense compounds have the following nucleobase motif:

```
ABCXXXXXXXXXXC'B'A';

ABCXXXXXXX(X/C')(X/B')(X/A');

(X/A)(X/B)(X/C)XXXXXXXXXXC'B'A'
``` where each of A, B, and C are any nucleobase; A', B', and C' are the complementary bases to A, B, and C, respectively; each X is a nucleobase complementary to the target nucleic acid; and two letters in parentheses (e.g., (X/C')) indicates that the nucleobase is complementary to the target nucleic acid and to the designated nucleoside within the antisense oligonucleotide.

Without being bound to any mechanism, in certain embodiments, such antisense compounds are expected to form self-structure, which is disrupted upon contact with a target nucleic acid. Contact with a non-target nucleic acid is expected to disrupt the self-structure to a lesser degree, thus increasing selectivity compared to the same antisense compound lacking the self-complementary regions.

v. Combinations of Features

Though it is clear to one of skill in the art, the above motifs and other elements for increasing selectivity may be used alone or in combination. For example, a single antisense compound may include any one, two, three, or more of: self-complementary regions, a mismatch relative to the target nucleic acid, a short nucleoside gap, an interrupted gap, and specific placement of the selective nucleoside.

C. Certain Target Nucleic Acids

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a non-coding RNA. In certain such embodiments, the target non-coding RNA is selected from: a long-non-coding RNA, a short non-coding RNA, an intronic RNA molecule, a snoRNA, a scaRNA, a microRNA (including pre-microRNA and mature microRNA), a ribosomal RNA, and promoter directed RNA. In certain embodiments, the target nucleic acid encodes a protein. In certain such embodiments, the target nucleic acid is selected from: an mRNA and a pre-mRNA, including intronic, exonic and untranslated regions. In certain embodiments, oligomeric compounds are at least partially complementary to more than one target nucleic acid. For example, antisense compounds of the present invention may mimic microRNAs, which typically bind to multiple targets.

In certain embodiments, the target nucleic acid is a nucleic acid other than a mature mRNA. In certain embodiments, the target nucleic acid is a nucleic acid other than a mature mRNA or a microRNA. In certain embodiments, the target nucleic acid is a non-coding RNA other than a microRNA. In certain embodiments, the target nucleic acid is a non-coding RNA other than a microRNA or an intronic region of a pre-mRNA. In certain embodiments, the target nucleic acid is a long non-coding RNA. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target nucleic acid is selected from among non-coding RNA, including exonic regions of pre-mRNA. In certain embodiments, the target nucleic acid is a ribosomal RNA (rRNA). In certain embodiments, the target nucleic acid is a non-coding RNA associated with splicing of other pre-mRNAs. In certain embodiments, the target nucleic acid is a nuclear-retained non-coding RNA.

In certain embodiments, antisense compounds described herein are complementary to a target nucleic acid comprising a single-nucleotide polymorphism. In certain such embodiments, the antisense compound is capable of modulating expression of one allele of the single-nucleotide polymorphism-containing-target nucleic acid to a greater or lesser extent than it modulates another allele. In certain embodiments an antisense compound hybridizes to a single-nucleotide polymorphism-containing-target nucleic acid at the single-nucleotide polymorphism site.

a. Single-Nucleotide Polymorphism

In certain embodiments, the invention provides selective antisense compounds that have greater activity for a target nucleic acid than for a homologous or partially homologous non-target nucleic acid. In certain such embodiments, the target and non-target nucleic acids are not functionally related to one another (e.g., are transcripts from different genes). In certain embodiments, the target and not-target nucleic acids are allelic variants of one another. Certain embodiments of the present invention provide methods, compounds, and compositions for selectively inhibiting mRNA and protein expression of an allelic variant of a particular gene or DNA sequence. In certain embodiments, the allelic variant contains a single nucleotide polymorphism (SNP). In certain embodiments, a SNP is associated with a mutant allele. In certain embodiments, a mutant SNP is associated with a disease. In certain embodiments a mutant SNP is associated with a disease, but is not causative of the disease. In certain embodiments, mRNA and protein expression of a mutant allele is associated with disease.

In certain embodiments, the expressed gene product of a mutant allele results in aggregation of the mutant proteins causing disease. In certain embodiments, the expressed gene product of a mutant allele results in gain of function causing disease. In certain embodiments, genes with an autosomal dominant mutation resulting in a toxic gain of function of the protein are the APP gene encoding amyloid precursor protein involved in Alzheimer's disease (Gene, 371: 68, 2006); the PrP gene encoding prion protein involved in Creutzfeldt-Jakob disease and in fatal familial insomnia (Nat. Med. 1997, 3: 1009); GFAP gene encoding glial fibrillary acidic protein involved in Alexander disease (J. Neurosci. 2006, 26:111623); alpha-synuclein gene encoding alpha-synuclein protein involved in Parkinson's disease (J. Clin. Invest. 2003, 111: 145); SOD-1 gene encoding the SOD-1 protein involved in amyotrophic lateral sclerosis (Science 1998, 281: 1851); atrophin-1 gene encoding atrophin-1 protein involved in dentato-rubral and pallido-luysian atrophy (DRPA) (Trends Mol. Med. 2001, 7: 479); SCA1 gene encoding ataxin-1 protein involved in spino-cerebellar ataxia-1 (SCA1) (Protein Sci. 2003, 12: 953); PLP gene encoding proteolipid protein involved in Pelizaeus-Merzbacher disease (NeuroMol Med. 2007, 4: 73); DYT1 gene encoding torsinA protein involved in Torsion dystonia (Brain Res. 2000, 877: 379); and alpha-B crystalline gene encoding alpha-B crystalline protein involved in protein aggregation diseases, including cardiomyopathy (Cell 2007, 130: 427); alpha1-antitrypsin gene encoding alpha1-antitrypsin protein involved in chronic obstructive pulmonary disease (COPD), liver disease and hepatocellular carcinoma (New Engl J Med. 2002, 346: 45); Ltk gene encoding leukocyte tyrosine kinase protein involved in systemic lupus erythematosus (Hum. Mol. Gen. 2004, 13: 171); PCSK9 gene encoding PCSK9 protein involved in hypercholesterolemia (Hum Mutat. 2009, 30: 520); prolactin receptor gene encoding prolactin receptor protein involved in breast tumors (Proc. Natl. Assoc. Sci. 2008, 105: 4533); CCL5 gene encoding the chemokine CCL5 involved in COPD and asthma (Eur. Respir. J. 2008, 32: 327); PTPN22 gene encoding PTPN22 protein involved in Type 1 diabetes, Rheumatoid arthritis, Graves disease, and SLE (Proc. Natl. Assoc. Sci. 2007, 104: 19767); androgen receptor gene encoding the androgen receptor protein involved in spinal and bulbar muscular atrophy or Kennedy's disease (J Steroid Biochem. Mol. Biol. 2008, 108: 245); CHMP4B gene encoding chromatin modifying protein-4B involved in progressive childhood posterior subcapsular cataracts (Am. J. Hum. Genet 2007, 81: 596); FXR/NR1H4 gene encoding Farnesoid X receptor protein involved in cholesterol gallstone disease, arthrosclerosis and diabetes (Mol. Endocrinol. 2007, 21: 1769); ABCA1 gene encoding ABCA1 protein involved in cardiovascular disease (Transl. Res. 2007, 149: 205); CaSR gene encoding the calcium sensing receptor protein involved in primary hypercalciuria (Kidney Int. 2007, 71: 1155); alpha-globin gene encoding alpha-globin protein involved in alpha-thallasemia (Science 2006, 312: 1215); httlpr gene encoding HTTLPR protein involved in obsessive compulsive disorder (Am. J. Hum. Genet. 2006, 78: 815); AVP gene encoding arginine vasopressin protein in stress-related disorders such as anxiety disorders and comorbid depression (CNS Neurol. Disord. Drug Targets 2006, 5: 167); GNAS gene encoding G proteins involved in congenital visual defects, hypertension, metabolic syndrome (Trends Pharmacol. Sci. 2006, 27: 260); APAF1 gene encoding APAF1 protein involved in a predisposition to major depression (Mol. Psychiatry 2006, 11: 76); TGF-beta1 gene encoding TGF-beta1 protein involved in breast cancer and prostate cancer (Cancer Epidemiol. Biomarkers Prev. 2004, 13: 759); AChR gene encoding acetylcholine receptor involved in congenital myasthenic syndrome (Neurology 2004, 62: 1090); P2Y12 gene encoding adenosine diphosphate (ADP) receptor protein involved in risk of peripheral arterial disease (Circulation 2003, 108: 2971); LQT1 gene encoding LQT1 protein involved in atrial fibrillation (Cardiology 2003, 100: 109); RET protooncogene encoding RET protein involved in sporadic pheochromocytoma (J. Clin. Endocrinol. Metab. 2003, 88: 4911); filamin A gene encoding filamin A protein involved in various congenital malformations (Nat. Genet. 2003, 33: 487); TARDBP gene encoding TDP-43 protein involved in amyotrophic lateral sclerosis (Hum. Mol. Gene.t 2010, 19: 671); SCA3 gene encoding ataxin-3 protein involved in Machado-Joseph disease (PLoS One 2008, 3: e3341); SCAT gene encoding ataxin-7 protein involved in spino-cerebellar ataxia-7 (PLoS One 2009, 4: e7232); and HTT gene encoding huntingtin protein involved in Huntington's disease (Neurobiol Dis. 1996, 3:183); and the CA4 gene encoding carbonic anhydrase 4 protein, CRX gene encoding cone-rod homeobox transcription factor protein, FSCN2 gene encoding retinal fascin homolog 2 protein, IMPDH1 gene encoding inosine monophosphate dehydrogenase 1 protein, NR2E3 gene encoding nuclear receptor subfamily 2 group E3 protein, NRL gene encoding neural retina leucine zipper protein, PRPF3 (RP18) gene encoding pre-mRNA splicing factor 3 protein, PRPF8 (RP13) gene encoding pre-mRNA splicing factor 8 protein, PRPF31 (RP11) gene encoding pre-mRNA splicing factor 31 protein, RDS gene encoding peripherin 2 protein, ROM1 gene encoding rod outer membrane protein 1 protein, RHO gene encoding rhodopsin protein, RP1 gene encoding RP1 protein, RPGR gene encoding retinitis pigmentosa GTPase regulator protein, all of which are involved in Autosomal Dominant Retinitis Pigmentosa disease (Adv Exp Med Biol. 2008, 613:203)

In certain embodiments, the mutant allele is associated with any disease from the group consisting of Alzheimer's disease, Creutzfeldt-Jakob disease, fatal familial insomnia, Alexander disease, Parkinson's disease, amyotrophic lateral sclerosis, dentato-rubral and pallido-luysian atrophy DRPA, spino-cerebellar ataxia, Torsion dystonia, cardiomyopathy, chronic obstructive pulmonary disease (COPD), liver disease, hepatocellular carcinoma, systemic lupus erythematosus, hypercholesterolemia, breast cancer, asthma, Type 1 diabetes, Rheumatoid arthritis, Graves disease, SLE, spinal and bulbar muscular atrophy, Kennedy's disease, progressive childhood posterior subcapsular cataracts, cholesterol gallstone disease, arthrosclerosis, cardiovascular disease, primary hypercalciuria, alpha-thallasemia, obsessive compulsive disorder, Anxiety, comorbid depression, congenital visual defects, hypertension, metabolic syndrome, prostate cancer, congenital myasthenic syndrome, peripheral arterial disease, atrial fibrillation, sporadic pheochromocytoma, congenital malformations, Machado-Joseph disease, Huntington's disease, and Autosomal Dominant Retinitis Pigmentosa disease.

D. Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water.

In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain.

E. Administration

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump. In certain embodiments, parenteral administration is by injection.

In certain embodiments, compounds and compositions are delivered to the CNS. In certain embodiments, compounds and compositions are delivered to the cerebrospinal fluid. In certain embodiments, compounds and compositions are administered to the brain parenchyma. In certain embodiments, compounds and compositions are delivered to an animal by intrathecal administration, or intracerebroventricular administration. Broad distribution of compounds and compositions, described herein, within the central nervous system may be achieved with intraparenchymal administration, intrathecal administration, or intracerebroventricular administration.

In certain embodiments, parenteral administration is by injection. The injection may be delivered with a syringe or a pump. In certain embodiments, the injection is a bolus injection. In certain embodiments, the injection is administered directly to a tissue, such as striatum, caudate, cortex, hippocampus and cerebellum.

Therefore, in certain embodiments, delivery of a compound or composition described herein can affect the pharmacokinetic profile of the compound or composition. In certain embodiments, injection of a compound or composition described herein, to a targeted tissue improves the pharmacokinetic profile of the compound or composition as compared to infusion of the compound or composition. In a certain embodiment, the injection of a compound or composition improves potency compared to broad diffusion, requiring less of the compound or composition to achieve similar pharmacology. In certain embodiments, similar pharmacology refers to the amount of time that a target mRNA and/or target protein is down-regulated (e.g. duration of action). In certain embodiments, methods of specifically localizing a pharmaceutical agent, such as by bolus injection, decreases median effective concentration (EC50) by a factor of about 50 (e.g. 50 fold less concentration in tissue is required to achieve the same or similar pharmacodynamic effect). In certain embodiments, methods of specifically localizing a pharmaceutical agent, such as by bolus injection, decreases median effective concentration (EC50) by a factor of 20, 25, 30, 35, 40, 45 or 50. In certain embodiments the pharmaceutical agent in an antisense compound as further described herein. In certain embodiments, the targeted tissue is brain tissue. In certain embodiments the targeted tissue is striatal tissue. In certain embodiments, decreasing EC50 is desirable because it reduces the dose required to achieve a pharmacological result in a patient in need thereof.

In certain embodiments, an antisense oligonucleotide is delivered by injection or infusion once every month, every two months, every 90 days, every 3 months, every 6 months, twice a year or once a year.

F. Certain Combination Therapies

In certain embodiments, one or more pharmaceutical compositions are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions as described herein. In certain embodiments, one or more pharmaceutical compositions are co-administered with another pharmaceutical agent to treat an undesired effect of that other pharmaceutical agent. In certain embodiments, one or more pharmaceutical compositions are co-administered with another pharmaceutical agent to produce a combinational effect. In certain embodiments, one or more pharmaceutical compositions are co-administered with another pharmaceutical agent to produce a synergistic effect.

In certain embodiments, one or more pharmaceutical compositions and one or more other pharmaceutical agents are administered at the same time. In certain embodiments, one or more pharmaceutical compositions and one or more other pharmaceutical agents are administered at different times. In certain embodiments, one or more pharmaceutical compositions and one or more other pharmaceutical agents are prepared together in a single formulation. In certain embodiments, one or more pharmaceutical compositions and one or more other pharmaceutical agents are prepared separately.

In certain embodiments, pharmaceutical agents that may be co-administered with a pharmaceutical composition of include antipsychotic agents, such as, e.g., haloperidol, chlorpromazine, clozapine, quetapine, and olanzapine; antidepressant agents, such as, e.g., fluoxetine, sertraline hydrochloride, venlafaxine and nortriptyline; tranquilizing agents such as, e.g., benzodiazepines, clonazepam, paroxetine, venlafaxin, and beta-blockers; mood-stabilizing agents such as, e.g., lithium, valproate, lamotrigine, and carbamazepine; paralytic agents such as, e.g., Botulinum toxin; and/or other experimental agents including, but not limited to, tetrabenazine (Xenazine), creatine, conezyme Q10, trehalose, docosahexanoic acids, ACR16, ethyl-EPA, atomoxetine, citalopram, dimebon, memantine, sodium phenylbutyrate, ramelteon, ursodiol, zyprexa, xenasine, tiapride, riluzole, amantadine, [123]MNI-420, atomoxetine, tetrabenazine, digoxin, detromethorphan, warfarin, alprozam, ketoconazole, omeprazole, and minocycline.

G. Certain Instances of Acute CNS Toxicity

In certain embodiments, compounds and compositions, including modified oligonucleotides, are delivered to the CNS. In certain embodiments, compounds and compositions, including modified oligonucleotides, are delivered to the CNS via intracerebroventricular administration or intracerebroventricular bolus administration. In certain embodiments, one or more modified oligonucleotides may exhibit high potency and high selectivity toward a nucleic acid target, but may possess certain degrees of acute toxicity when delivered into the CNS via intracerebroventricular administration. In certain embodiments, introduction of one or more modifications to the internucleoside linkages of the modified oligonucleotide ameliorates or reduces acute toxicity associated with CNS delivery via intracerebroventricular administration. In certain embodiments, introduction of one or more phosphodiester internucleoside linkages into the modified oligonucleotide ameliorates or reduces acute toxicity associated with CNS delivery via intracerebroventricular administration. In certain embodiments, introduction of one or more phosphodiester internucleoside linkages into the 5'-region of the modified oligonucleotide ameliorates or reduces acute toxicity associated with CNS delivery via intracerebroventricular administration. In certain embodiments, introduction of one or more phosphodiester internucleoside linkages into the 3'-region of the modified oligonucleotide ameliorates or reduces acute toxicity associated with CNS delivery via intracerebroventricular administration. In certain embodiments, introduction of one or more phosphodiester internucleoside linkages into both the 5'-region and the 3'-region of the modified oligonucleotide ameliorates or reduces acute toxicity associated with CNS delivery via intracerebroventricular administration. In certain embodiments, introduction of one or more phosphodiester internucleoside linkages and one or more phosphorothioate internucleoside linkages into the modified oligonucleotide ameliorates or reduces acute toxicity associated with CNS delivery via intracerebroventricular administration.

In certain embodiments, introduction of one or more modifications to the nucleosides of the modified oligonucleotide ameliorates or reduces acute toxicity associated with CNS delivery via intracerebroventricular administration. In certain embodiments, introduction of one or more modifications to the 5'-region nucleosides of the modified oligonucleotide ameliorates or reduces acute toxicity associated with CNS delivery via intracerebroventricular administration. In certain embodiments, introduction of one or more modifications to the 3'-region nucleosides of the modified oligonucleotide ameliorates or reduces acute toxicity associated with CNS delivery via intracerebroventricular administration. In certain embodiments, introduction of one or more modifications to both the 5'-region and the 3'-region nucleosides of the modified oligonucleotide ameliorates or reduces acute toxicity associated with CNS delivery via intracerebroventricular administration. In certain embodiments, introduction of one or more modifications to the 5'-region or the 3'-region nucleosides, or to both the 5'-region and the 3'-region nucleosides serves to shorten the central region between the 5'-region and the 3'-region which ameliorates or reduces acute toxicity associated with CNS delivery via intracerebroventricular administration. In certain embodiments, the central region comprises 10 nucleobases. In certain embodiments the central region comprises 9 nucleobases. In certain embodiments, the central region comprises 8 nucleobases. In certain embodiments the central region comprises 7 nucleobases. In certain embodiments, the central region comprises 6 nucleobases. In certain embodiments the central region comprises 5 nucleobases.

In certain embodiments, introduction of one or more modifications to the nucleosides of the modified oligonucleotide in addition to the introduction of one or more modifications to the internucleoside linkages of the modified oligonucleotide ameliorates or reduces acute toxicity associated with CNS delivery via intracerebroventricular administration. In certain embodiments, introduction of one or more phosphodiester internucleoside linkages into the modified oligonucleotide and shortening of the central region of the modified oligonucleotide ameliorates or reduces acute toxicity associated with CNS delivery via intracerebroventricular administration.

NONLIMITING DISCLOSURE AND INCORPORATION BY REFERENCE

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^{me}$CGAUCG," wherein $^{me}$C indicates a cytosine base comprising a methyl group at the 5-position.

EXAMPLES

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

To allow assessment of the relative effects of nucleobase sequence and chemical modification, throughout the examples, oligomeric compounds are assigned a "Sequence Code." Oligomeric compounds having the same Sequence Code have the same nucleobase sequence. Oligomeric compounds having different Sequence Codes have different nucleobase sequences.

Example 1

Oligonucleotides Designed to Target A

Oligonucleotides, shown in the table below, were designed to target Target A. Each "E" is a 2'MOE modified nucleoside, each "K" is a cEt modified nucleoside, each "D" is an unmodified deoxynucleoside, each "X" comprises a 2-thiothymidine, each "s" is a phosphorothioate internucleoside linkage, and each "o" is a phosphodiester internucleoside linkage.

TABLE 14

Modified Oligonucleotides Designed to Target A

| 5'-wing region | Central gap region | 3'-wing region |
| --- | --- | --- |
| $E_s E_o E_o E_o E_o K_s$ | $D_s D_s D_s D_s D_s D_s D_s$ | $K_s E_s E$ |
| $E_s E_o E_o E_o E_o K_s$ | $D_s D_s D_s D_s D_s D_s$ | $E_s E_s E$ |
| $E_s K_o E_o K_s$ | $D_s D_s D_s D_s D_s D_s D_s D_s$ | $K_o E_s K_s E$ |
| $E_s E_o E_o E_o E_s D_s K_s$ | $D_s D_s D_s D_s D_s D_s D_s$ | $E_o E_o E_s E_s E$ |
| $E_s E_s E_o E_o E_s K_s$ | $D_s D_s D_s D_s D_s D_s$ | $E_o E_o E_o E_s E_s E$ |
| $E_s E_o E_o E_s K_s$ | $D_s D_s D_s D_s D_s D_s$ | $E_s E_o E_o E_o E_s E_s E$ |
| $E_s E_o E_s K_s$ | $D_s D_s D_s D_s D_s D_s$ | $E_s E_o E_o E_o E_o E_s E_s E$ |
| $E_s E_o K_s$ | $D_s D_s D_s D_s D_s D_s$ | $E_s E_s E_o E_o E_o E_o E_s E_s E$ |
| $E_s K_s$ | $D_s D_s D_s D_s D_s D_s$ | $E_s E_s E_o E_o E_o E_o E_o E_s E_s E$ |
| $E_s E_s E_o E_o E_o E_o E_s K_s$ | $D_s D_s D_s D_s D_s D_s$ | $E_o E_s E_s E$ |

TABLE 14-continued

Modified Oligonucleotides Designed to Target A

| 5'-wing region | Central gap region | 3'-wing region |
|---|---|---|
| $E_s E_s E_o E_o E_o E_o$ $E_o E_s K_s$ | $D_s D_s D_s D_s D_s D_s D_s$ | $E_s E_s E$ |
| $E_s E_o K_o K_s$ | $D_s D_s D_s D_s D_s D_s D_s$ | $K_o K_o E_s E_s E$ |
| $E_s K_s$ | $D_s D_s D_s D_s D_s D_s D_s D_s$ | $K_o K_o K_s E$ |
| $E_s E_o E_o E_s K_s$ | $D_s D_s D_s D_s D_s D_s$ | $K_s E_o E_o E_s E$ |
| $E_s E_s E_o K_o K_s$ | $D_s D_s D_s D_s D_s D_s$ | $K_o K_o E_s E_s E$ |
| $E_s E_o K_o K_s$ | $D_s D_s D_s D_s D_s D_s D_s$ | $K_o K_o E_s E_s E$ |
| $E_s K_o E_o K_s$ | $D_s D_s D_s D_s D_s D_s D_s$ | $K_o E_o K_s E_s E$ |
| $E_s E_o K_o K_s$ | $D_s D_s D_s D_s D_s D_s D_s$ | $K_o K_o E_s E_s E$ |
| $E_s K_s$ | $D_s D_s D_s D_s D_s D_s D_s$ | $E_s E_s E_o K_s K$ |
| $K_s$ | $D_s D_s D_s D_s D_s D_s D_s D_s$ | $E_s E_o K_o E_s K_s E$ |
| $K_s$ | $D_s D_s D_s D_s D_s D_s D_s$ | $E_s E_s E_o K_o E_s K_s E$ |
| $K_s$ | $D_s D_s D_s D_s D_s D_s D_s D_s$ | $E_s E_o K_o E_s K_s E$ |
| $K_s$ | $D_s D_s D_s D_s D_s D_s D_s$ | $E_s E_s E_o K_o E_s K_s E$ |
| $K_s$ | $D_s D_s D_s D_s D_s D_s D_s$ | $K_s E_s E_o E_o K_s E_s E$ |
| $K_s$ | $D_s D_s D_s D_s D_s D_s D_s D_s$ | $K_s E_o E_o K_s E_s E_s E$ |
| $E_s E_s K_s$ | $D_s D_s D_s D_s D_s D_s D_s$ | $E_o E_s K_s E$ |
| $E_s E_s K_s$ | $D_s D_s D_s D_s D_s D_s D_s D_s$ | $E_o E_s K_s E$ |
| $E_s E_s K_s$ | $D_s D_s D_s D_s D_s D_s D_s$ | $E_o E_o E_s K_s E$ |
| $E_s E_s K_s$ | $D_s D_s D_s D_s D_s D_s D_s$ | $E_s E_o E_o K_s E_s K$ |
| $E_s E_s K_s$ | $D_s D_s D_s D_s D_s D_s D_s$ | $K_o E_s E_s E$ |
| $E_s E_s K_s$ | $D_s D_s D_s D_s D_s D_s D_s$ | $K_s E_o E_o E_s K_s E$ |
| $E_s K_s$ | $D_s D_s D_s D_s D_s D_s$ | $E_s E_s E_s E_o K_o E_s K_s E$ |
| $E_s K_s$ | $D_s D_s D_s D_s D_s D_s D_s$ | $K_s E_s E_o E_o K_s E_s E$ |
| $E_s K_s$ | $D_s D_s D_s D_s D_s D_s D_s$ | $E_s E_o E_o K_s E_s K$ |
| $E_s E_s K_s$ | $D_s D_s D_s D_s D_s D_s D_s D_s$ | $E_o E_o K_s E_s K$ |
| $E_s K_s$ | $D_s D_s D_s D_s D_s D_s D_s$ | $E_s E_s E_o K_o E_s K_s E$ |
| $K_s$ | $D_s D_s D_s D_s D_s D_s D_s D_s$ | $E_s E_o K_o E_s K_s E_s E$ |
| $E_s K_s$ | $D_s D_s D_s D_s D_s D_s D_s$ | $E_s E_s E_o K_o E_s K_s E$ |
| $E_s K_s K_s$ | $D_s X_s D_s D_s D_s D_s D_s D_s$ | $K_s K_s E$ |
| $E_s K_o K_o K_s$ | $D_s X_s D_s D_s D_s D_s D_s D_s$ | $K_o E_s K_s E$ |
| $E_s K_s E_s K_s$ | $D_s X_s D_s D_s D_s D_s D_s D_s$ | $K_s E_s E_s E$ |
| $E_s E_s E_s K_s$ | $D_s X_s D_s D_s D_s D_s D_s D_s$ | $K_s E_s E_s E$ |
| $E_s K_s E_s K_s$ | $D_s X_s D_s D_s D_s D_s D_s D_s$ | $K_s E_s K_s E$ |
| $E_s K_s$ | $D_s D_s D_s D_s D_s D_s D_s D_s$ | $E_s E_o K_s K$ |
| $E_s K_s$ | $D_s D_s D_s D_s D_s D_s D_s D_s$ | $K_s E_o K_s E$ |
| $K_s$ | $D_s D_s D_s D_s D_s D_s D_s D_s$ | $E_s E_o K_s E_s K$ |
| $K_s$ | $D_s D_s D_s D_s D_s D_s D_s D_s$ | $K_s E_o E_s K_s K$ |
| $E_s E_s K_s$ | $D_s D_s D_s D_s D_s D_s D_s$ | $K_o K_o E_s E_s K$ |
| $E_s E_s K_s$ | $D_s D_s D_s D_s D_s D_s D_s D_s$ | $K_s E_o E_s K_s E$ |
| $E_s K_s$ | $D_s D_s D_s D_s D_s D_s D_s D_s$ | $E_s E_o K_o E_s K_s E$ |
| $E_s K_s$ | $D_s D_s D_s D_s D_s D_s D_s$ | $E_s E_s E_o K_o E_s K_s E$ |
| $E_s K_s$ | $D_s D_s D_s D_s D_s D_s D_s D_s$ | $K_s E_o E_o K_s E_s E$ |
| $E_s K_s$ | $D_s D_s D_s D_s D_s D_s D_s D_s$ | $E_o E_o K_s E_s K$ |
| $E_s K_s$ | $D_s D_s D_s D_s D_s D_s D_s$ | $E_s E_s E_o E_o K_s E_s K$ |
| $E_s K_s$ | $D_s D_s D_s D_s D_s D_s D_s D_s$ | $E_s E_o K_o E_s K_s E$ |

Example 2

In Vivo Analysis of Oligonucleotides Designed to Target A

Oligonucleotides, shown in the table below, were designed to target one region of Target A. Mice were separated into groups of 4 mice. Each mouse in each group of mice was administered a single 300 μg ICV dose of each of the oligonucleotides in the table below. At 3 hours post injection, each mouse was evaluated according to 7 different criteria. The 7 criteria are (1) the mouse was bright, alert, and responsive; (2) the mouse was standing or hunched without stimuli; (3) the mouse shows any movement without stimuli (4) the mouse demonstrates forward movement after its lifted; (5) the mouse demonstrates any movement after its lifted; (6) the mouse responds to a tail pinch; (7) regular breathing. For each of the 7 different criteria, each mouse was given a sub-score of 0 if it met the criteria or 1 if it did not. After all of the 7 criteria were evaluated, the sub-scores were summed for each mouse and then averaged for each group. For example, if a mouse was bright, alert, and responsive 3 hours after the 300 μg ICV dose, and met all other other criteria, it would get a summed score of 0. If another mouse was not bright, alert, and responsive 3 hours after the 300 μg ICV dose but met all other criteria, it would receive a score of 1. Saline treated mice generally receive a score of 0. A score at the top end of the range would be suggestive of acute toxicity. In the table below, a subscript 'k' indicates an (S)-cEt modification; a subscript 'e' indicates a MOE modification; a subscript 'd' indicates a 2'-deoxynucleoside; a subscript 'g' indicates a 3'-fluoro-HNA nucleoside; a subscript 'f' indicates a 2'-fluoro modification; and 'N' indicates a masked nucleoside. Subscripts 's' and 'o' refer to phosphorothioate and phosphodiester internucleoside bonds, respectively. Oligonucleotides with the same sequence identifiers have the same nucleobase sequences.

TABLE 15

300 μg ICV Bolus Study With Mice

| ISIS NO. | Sequence (5' to 3') | Sugar Motif | Score at 3 hours post injection | Sequence Identifier | SEQ ID NO |
|---|---|---|---|---|---|
| A1 | $N_{es}N_{es}N_{es}N_{ks}N_{ks}N_{ds}N_{ds}N_{ds}N_{ds}N_{ds}N_{ds}N_{ds}N_{ks}N_{ks}N_e$ | 5-7-3 | .3 | 1 | 1 |
| A2 | $N_{es}N_{es}N_{es}N_{es}N_{ks}N_{ks}N_{ds}N_{ds}N_{ds}N_{ds}N_{ds}N_{ds}N_{ds}N_{ks}N_{ks}N_{es}N_{ks}N_e$ | 6-7-4 | 0 | 2 | 2 |
| A3 | $N_{es}N_{es}N_{es}N_{ks}N_{ks}N_{ds}N_{ds}N_{ds}N_{ds}N_{ds}N_{ds}N_{ds}N_{ks}N_{ks}N_{es}N_{es}N_e$ | 5-7-5 | .3 | 2 | 3 |
| A4 | $N_{es}N_{ks}N_{es}N_{ks}N_{es}N_{ks}N_{ds}N_{ds}N_{ds}N_{ds}N_{ds}N_{ds}N_{ds}N_{ks}N_{es}N_{ks}N_e$ | 6-7-4 | 1 | 2 | 2 |
| A5 | $N_{ks}N_{ks}N_{ks}N_{ks}N_{ks}N_{ds}N_{ds}N_{ds}N_{ds}N_{ds}N_{ds}N_{ds}N_{ks}N_{ks}N_{ks}N_{ks}N_k$ | 5-7-5 | 1.3 | 2 | 3 |
| A6 | $N_{es}N_{ks}N_{ks}N_{ds}N_{gs}N_{ds}N_{ds}N_{ds}N_{ds}N_{ds}N_{ds}N_{ds}N_{ks}N_{ks}N_e$ | 3-1-1-7-3 | 1.5 | 1 | 4 |
| A7 | $N_{es}N_{ks}N_{ks}N_{ds}N_{ks}N_{ds}N_{ds}N_{ds}N_{ds}N_{ds}N_{ds}N_{ds}N_{ks}N_{ks}N_e$ | 3-1-1-7-3 | 1.8 | 1 | 4 |
| A8 | $N_{ks}N_{ks}N_{es}N_{ks}N_{ks}N_{ds}N_{ds}N_{ds}N_{ds}N_{ds}N_{ds}N_{ds}N_{ds}N_{ks}N_{ks}N_{es}N_{ks}N_k$ | 5-9-5 | 2 | 3 | 5 |
| A9 | $N_{es}N_{ks}N_{ds}N_{ds}N_{ds}N_{ds}N_{ds}N_{ds}N_{ds}N_{ds}N_{ds}N_{ks}N_{ks}N_{ks}N_e$ | 2-9-4 | 3.5 | 4 | 6 |

TABLE 15-continued

300 µg ICV Bolus Study With Mice

| ISIS NO. | Sequence (5' to 3') | Sugar Motif | Score at 3 hours post injection | Sequence Identifier | SEQ ID NO |
|---|---|---|---|---|---|
| A10 | $N_{es}N_{es}N_{es}N_{ks}N_{ks}N_{ds}N_{ds}N_{ds}N_{ds}N_{ds}N_{ds}N_{ds}N_{ks}N_{ks}N_{es}N_{es}N_{e}$ | 5-7-5 | 4.5 | 5 | 3 |
| A11 | $N_{es}N_{ks}N_{ds}N_{ds}N_{ds}N_{ds}N_{ds}N_{ds}N_{ds}N_{ds}N_{ds}N_{ds}N_{ks}N_{ks}N_{ks}N_{e}$ | 2-9-4 | 4.3 | 6 | 6 |
| A12 | $N_{es}N_{ks}N_{ds}N_{ds}N_{ds}N_{ds}N_{ds}N_{ds}N_{ds}N_{ds}N_{ds}N_{ds}N_{ks}N_{ks}N_{ks}N_{e}$ | 2-9-4 | 6 | 7 | 6 |
| A13 | $N_{es}N_{ks}N_{ks}N_{ks}N_{ds}N_{ds}N_{ds}N_{ds}N_{ds}N_{ds}N_{ds}N_{ds}N_{ds}N_{ds}N_{ks}N_{e}$ | 4-9-2 | ND | 4 | 7 |
| A14 | $N_{es}N_{ks}N_{ds}N_{ds}N_{ds}N_{ds}N_{ds}N_{ds}N_{ds}N_{ds}N_{ds}N_{ds}N_{ko}N_{ko}N_{ks}N_{e}$ | 2-9-4 | 0.5 | 7 | 6 |
| A15 | $N_{es}N_{ko}N_{ko}N_{ko}N_{ks}N_{ks}N_{ds}N_{ds}N_{ds}N_{ds}N_{ds}N_{ds}N_{ds}N_{ko}N_{ko}N_{ks}N_{e}$ | 6-7-4 | 0 | 2 | 2 |
| A16 | $N_{es}N_{ks}N_{es}N_{ks}N_{ds}N_{ds}N_{ds}N_{ds}N_{ds}N_{ds}N_{ds}N_{ds}N_{ds}N_{ks}N_{es}N_{ks}N_{e}$ | 4-9-4 | 0 | 2 | 8 |
| A17 | $N_{es}N_{ks}N_{es}N_{ks}N_{ds}N_{ds}N_{ds}N_{ds}N_{ds}N_{ds}N_{ds}N_{ds}N_{ds}N_{ks}N_{es}N_{ks}N_{e}$ | 4-9-4 | 2.5 | 2 | 8 |
| A18 | $N_{es}N_{es}N_{es}N_{es}N_{ks}N_{ks}N_{ds}N_{ds}N_{ds}N_{ks}N_{ds}N_{ds}N_{ds}N_{ks}N_{es}N_{ks}N_{e}$ | 6-7-4 | 0 | 2 | 2 |
| A19 | $N_{ks}N_{ko}N_{ko}N_{ko}N_{ks}N_{ds}N_{ds}N_{ds}N_{ds}N_{ds}N_{ds}N_{ds}N_{ko}N_{ko}N_{ko}N_{ks}N_{k}$ | 5-7-5 | 0 | 5 | 3 |
| A20 | $N_{ks}N_{ko}N_{ko}N_{ko}N_{ko}N_{ds}N_{ds}N_{ds}N_{ds}N_{ds}N_{ds}N_{ds}N_{ko}N_{ko}N_{ko}N_{ko}N_{k}$ | 5-7-5 | 0 | 2 | 3 |
| A21 | $N_{es}N_{es}N_{es}N_{es}N_{ds}N_{ks}N_{ds}N_{ds}N_{ds}N_{ds}N_{ds}N_{ds}N_{ds}N_{ks}N_{ks}N_{es}N_{e}$ | 4-1-1-7-4 | 0 | 2 | 9 |
| A22 | $N_{es}N_{es}N_{es}N_{es}N_{ds}N_{ks}N_{ds}N_{ds}N_{ds}N_{ds}N_{ds}N_{ds}N_{ds}N_{ks}N_{es}N_{es}N_{e}$ | 4-1-1-7-4 | 0.5 | 2 | 9 |
| A23 | $N_{es}N_{es}N_{es}N_{es}N_{ds}N_{ks}N_{ds}N_{ds}N_{ds}N_{ds}N_{ds}N_{ds}N_{ds}N_{es}N_{es}N_{es}N_{e}$ | 4-1-1-7-4 | 0.8 | 2 | 9 |
| A24 | $N_{es}N_{es}N_{es}N_{ks}N_{ds}N_{ds}N_{ds}N_{ds}N_{ds}N_{ds}N_{ds}N_{ds}N_{ds}N_{ks}N_{es}N_{ks}N_{e}$ | 4-9-4 | 1.5 | 2 | 8 |
| A25 | $N_{es}N_{ks}N_{es}N_{ks}N_{ds}N_{ds}N_{ds}N_{ds}N_{ds}N_{ds}N_{ds}N_{ds}N_{ds}N_{ks}N_{es}N_{es}N_{e}$ | 4-9-4 | 1.5 | 2 | 8 |
| A26 | $N_{es}N_{es}N_{es}N_{ks}N_{ds}N_{ds}N_{ds}N_{ds}N_{ds}N_{ds}N_{ds}N_{ds}N_{ds}N_{ks}N_{es}N_{es}N_{e}$ | 4-9-4 | 2.3 | 2 | 8 |
| A27 | $N_{es}N_{ks}N_{es}N_{ks}N_{ds}N_{ds}N_{ds}N_{ds}N_{ds}N_{ds}N_{fs}N_{ds}N_{ds}N_{ks}N_{es}N_{ks}N_{e}$ | 4-9-4 | 2.8 | 2 | 8 |

In the table above, the oligonucleotides with mixed PO/PS backbones (Isis No.'s A14, A15, A19, and A20) have scores ranging from 0.0 to 0.5, whereas the oligonucleotides with full PS backbones have scores ranging from 0.0 to 6.0. The average score for full PS oligonucleotides with 7 nucleotide gaps is 1.00, and the median score is 0.65. The average score for full PS oligonucleotides with 9 nucleotide gaps is 2.64, and the median score is 2.40. Thus, this example shows that in certain embodiments, mixed PO/PS backbone and short gap containing oligonucleotides mitigated the acute toxicity induced by their full PS and long gap containing counterparts.

Example 3

In Vivo Analysis of Oligonucleotides Designed to Target B

Oligonucleotides, shown in the table below, were designed to target one region of Target B. Mice were separated into groups of 4 mice. Each mouse in each group of mice was administered a single 300 µg ICV dose of each of the oligonucleotides in the table below. At 3 hours post injection, each mouse was evaluated according to 7 different criteria. The 7 criteria are (1) the mouse was bright, alert, and responsive; (2) the mouse was standing or hunched without stimuli; (3) the mouse shows any movement without stimuli (4) the mouse demonstrates forward movement after its lifted; (5) the mouse demonstrates any movement after its lifted; (6) the mouse responds to a tail pinch; (7) regular breathing. For each of the 7 different criteria, each mouse was given a sub-score of 0 if it met the criteria or 1 if it did not. After all of the 7 criteria were evaluated, the sub-scores were summed for each mouse and then averaged for each group. For example, if a mouse was bright, alert, and responsive 3 hours after the 300 µg ICV dose, and met all other criteria, it would get a summed score of 0. If another mouse was not bright, alert, and responsive 3 hours after the 300 µg ICV dose but met all other criteria, it would receive a score of 1. See Example 2 for table legend.

TABLE 16

300 µg ICV Bolus Study With Mice

| ISIS NO. | Sequence (5' to 3') | Motif | Score at 3 hours post injection | Sequence Identifier | SEQ ID NO |
|---|---|---|---|---|---|
| B1 | $N_{es}N_{es}N_{es}N_{es}N_{es}N_{ds}N_{ds}N_{ds}N_{ds}N_{ds}N_{ds}N_{ds}N_{ds}N_{ds}N_{ds}N_{es}N_{es}N_{es}N_{es}N_{e}$ | eeeee-d10-eeeee | 4.3 | 8 | 10 |
| B2 | $N_{es}N_{eo}N_{eo}N_{eo}N_{ks}N_{ds}N_{ds}N_{ds}N_{ds}N_{ds}N_{ds}N_{ds}N_{ko}N_{eo}N_{eo}N_{es}N_{e}$ | eeeek-d7-keeee | 2 | 9 | 3 |
| B3 | $N_{es}N_{eo}N_{eo}N_{eo}N_{ks}N_{ds}N_{ds}N_{ds}N_{ds}N_{ds}N_{ds}N_{ds}N_{ko}N_{eo}N_{eo}N_{es}N_{e}$ | eeeek-d7-keeee | 1.3 | 10 | 3 |
| B4 | $N_{es}N_{eo}N_{eo}N_{eo}N_{ks}N_{ds}N_{ds}N_{ds}N_{ds}N_{ds}N_{ds}N_{ds}N_{ko}N_{eo}N_{eo}N_{es}N_{e}$ | eeeek-d7-keeee | 1.8 | 11 | 3 |
| B5 | $N_{es}N_{eo}N_{eo}N_{eo}N_{ks}N_{ds}N_{ds}N_{ds}N_{ds}N_{ds}N_{ds}N_{ds}N_{ko}N_{eo}N_{eo}N_{es}N_{e}$ | eeeek-d7-keeee | 1 | 12 | 3 |
| B6 | $N_{es}N_{eo}N_{eo}N_{ko}N_{ks}N_{ds}N_{ds}N_{ds}N_{ds}N_{ds}N_{ds}N_{ds}N_{ko}N_{ko}N_{eo}N_{es}N_{e}$ | eeekk-d7-kkeee | 1.8 | 9 | 3 |
| B7 | $N_{es}N_{eo}N_{eo}N_{ko}N_{ks}N_{ds}N_{ds}N_{ds}N_{ds}N_{ds}N_{ds}N_{ds}N_{ko}N_{ko}N_{eo}N_{es}N_{e}$ | eeek-d7-kkeee | 0.5 | 10 | 3 |
| B8 | $N_{es}N_{eo}N_{eo}N_{ko}N_{ks}N_{ds}N_{ds}N_{ds}N_{ds}N_{ds}N_{ds}N_{ds}N_{ko}N_{ko}N_{eo}N_{es}N_{e}$ | eeek-d7-kkeee | 2.3 | 11 | 3 |
| B9 | $N_{es}N_{eo}N_{eo}N_{ko}N_{ks}N_{ds}N_{ds}N_{ds}N_{ds}N_{ds}N_{ds}N_{ds}N_{ko}N_{ko}N_{eo}N_{es}N_{e}$ | eeekk-d7-kkeee | 0 | 12 | 3 |
| B10 | $N_{es}N_{eo}N_{ko}N_{eo}N_{ks}N_{ds}N_{ds}N_{ds}N_{ds}N_{ds}N_{ds}N_{ds}N_{ko}N_{eo}N_{ko}N_{es}N_{e}$ | eekek-d7-kekee | 3 | 9 | 3 |
| B11 | $N_{es}N_{eo}N_{ko}N_{eo}N_{ks}N_{ds}N_{ds}N_{ds}N_{ds}N_{ds}N_{ds}N_{ds}N_{ko}N_{eo}N_{ko}N_{es}N_{e}$ | eekek-d7-kekee | 0 | 11 | 3 |
| B12 | $N_{es}N_{ko}N_{eo}N_{eo}N_{ks}N_{ds}N_{ds}N_{ds}N_{ds}N_{ds}N_{ds}N_{ds}N_{ko}N_{eo}N_{eo}N_{ks}N_{e}$ | ekeek-d7-keeke | 1.8 | 9 | 3 |
| B13 | $N_{es}N_{ko}N_{eo}N_{eo}N_{ks}N_{ds}N_{ds}N_{ds}N_{ds}N_{ds}N_{ds}N_{ds}N_{ko}N_{eo}N_{eo}N_{ks}N_{e}$ | ekeek-d7-keeke | 0.3 | 10 | 3 |
| B14 | $N_{es}N_{ko}N_{eo}N_{eo}N_{ks}N_{ds}N_{ds}N_{ds}N_{ds}N_{ds}N_{ds}N_{ds}N_{ko}N_{eo}N_{eo}N_{ks}N_{e}$ | ekeek-d7-keeke | 2.3 | 11 | 3 |
| B15 | $N_{es}N_{ko}N_{eo}N_{eo}N_{ks}N_{ds}N_{ds}N_{ds}N_{ds}N_{ds}N_{ds}N_{ds}N_{ko}N_{eo}N_{eo}N_{ks}N_{e}$ | ekeek-d7-keeke | 0.8 | 12 | 3 |

This example shows that, in certain embodiments, oligonucleotides with mixed PO/PS backbones and short 7 nucleotide gaps mitigated the acute toxicity induced by a full PS, 10 nucleotide gap oligonucleotide (Isis No. B1).

Example 4

In Vivo Analysis of Oligonucleotides Designed to Target C

Oligonucleotides, shown in Table 17 below, were designed to target Target C. Mice were separated into groups of 4 mice. Each mouse in each group of mice was administered a single 300 µg ICV dose of each of the oligonucleotides in Table 17. The mice were then observed and evaluated according to Example 2 above. See Example 2 for table legend.

TABLE 17

300 µg ICV Bolus Study With Mice

| ISIS NO. | Sequence (5' to 3') | Backbone | Score at 3 hours post injection | Std Dev | Sequence Identifier | SEQ ID NO |
|---|---|---|---|---|---|---|
| C1 | $N_{es}N_{es}N_{es}N_{es}N_{es}N_{ds}N_{ds}N_{ds}N_{ds}N_{ds}N_{ds}N_{ds}N_{ds}N_{ds}N_{ds}N_{es}N_{es}N_{es}N_{es}N_{e}$ | PS | 2.25 | 1.30 | 13 | 10 |
| C2 | $N_{es}N_{eo}N_{eo}N_{eo}N_{es}N_{ds}N_{ds}N_{ds}N_{ds}N_{ds}N_{ds}N_{ds}N_{ds}N_{ds}N_{ds}N_{eo}N_{eo}N_{eo}N_{es}N_{e}$ | PO/PS | 0.00 | 0.00 | 13 | 10 |
| C3 | $N_{es}N_{es}N_{es}N_{es}N_{es}N_{ds}N_{ds}N_{ds}N_{ds}N_{ds}N_{ds}N_{ds}N_{ds}N_{ds}N_{ds}N_{es}N_{es}N_{es}N_{es}N_{e}$ | PS | 3.25 | 0.43 | 14 | 10 |
| C4 | $N_{es}N_{eo}N_{eo}N_{eo}N_{es}N_{ds}N_{ds}N_{ds}N_{ds}N_{ds}N_{ds}N_{ds}N_{ds}N_{ds}N_{ds}N_{eo}N_{eo}N_{eo}N_{es}N_{e}$ | PO/PS | 0.00 | 0.00 | 14 | 10 |
| C5 | $N_{es}N_{es}N_{es}N_{es}N_{es}N_{ds}N_{ds}N_{ds}N_{ds}N_{ds}N_{ds}N_{ds}N_{ds}N_{ds}N_{ds}N_{es}N_{es}N_{es}N_{es}N_{e}$ | PS | 6.00 | 0.00 | 15 | 10 |
| C6 | $N_{es}N_{eo}N_{eo}N_{eo}N_{es}N_{ds}N_{ds}N_{ds}N_{ds}N_{ds}N_{ds}N_{ds}N_{ds}N_{ds}N_{ds}N_{eo}N_{eo}N_{eo}N_{es}N_{e}$ | PO/PS | 3.50 | 0.50 | 15 | 10 |
| C7 | $N_{es}N_{es}N_{es}N_{es}N_{es}N_{ds}N_{ds}N_{ds}N_{ds}N_{ds}N_{ds}N_{ds}N_{ds}N_{ds}N_{ds}N_{es}N_{es}N_{es}N_{es}N_{e}$ | PS | 6.00 | 0.00 | 16 | 10 |
| C8 | $N_{es}N_{eo}N_{eo}N_{eo}N_{es}N_{ds}N_{ds}N_{ds}N_{ds}N_{ds}N_{ds}N_{ds}N_{ds}N_{ds}N_{ds}N_{eo}N_{eo}N_{eo}N_{es}N_{e}$ | PO/PS | 3.75 | 0.83 | 16 | 10 |
| C9 | $N_{es}N_{es}N_{es}N_{es}N_{es}N_{ds}N_{ds}N_{ds}N_{ds}N_{ds}N_{ds}N_{ds}N_{ds}N_{ds}N_{ds}N_{es}N_{es}N_{es}N_{es}N_{e}$ | PS | 6.00 | 0.00 | 17 | 10 |
| C10 | $N_{es}N_{eo}N_{eo}N_{eo}N_{es}N_{ds}N_{ds}N_{ds}N_{ds}N_{ds}N_{ds}N_{ds}N_{ds}N_{ds}N_{ds}N_{eo}N_{eo}N_{eo}N_{es}N_{e}$ | PO/PS | 3.00 | 0.00 | 17 | 10 |

In the table above, the difference between each pair of oligonucleotides with the same sequence identifier is the backbone motif. In each pair, the mixed PO/PS oligonucleotide induced less acute toxicity than its full PS counterpart. Thus, in certain embodiments, mixed PO/PS backbone oligonucleotides mitigated the acute toxicity induced by their full PS counterparts.

Example 5

In Vivo Analysis of Oligonucleotides Designed to Target C

Oligonucleotides, shown in Tables 18 and 19 below, were designed to target Target C. Mice were separated into groups of 4 mice. Each mouse in each group of mice was administered a single 300 µg ICV dose of each of the oligonucleotides in Tables 18 and 19. The mice were then observed and evaluated according to Example 2 above. See Example 2 for table legend.

TABLE 18

300 µg ICV Bolus Study With Oligonucleotides Containing 10 Nucleotide Gaps

| ISIS NO. | Sequence (5' to 3') | Score at 3 hours post injection | Std Dev | Sequence Identifier | SEQ ID NO |
|---|---|---|---|---|---|
| PBS | | 0.00 | 0.00 | | |
| C11 | $N_{es}N_{es}N_{es}N_{es}N_{es}N_{ds}N_{ds}N_{ds}N_{ds}N_{ds}N_{ds}N_{ds}N_{ds}N_{ds}N_{ds}N_{es}N_{es}N_{es}N_{es}N_{e}$ | 5.25 | 0.50 | 18 | 10 |
| C12 | $N_{es}N_{es}N_{es}N_{es}N_{es}N_{ds}N_{ds}N_{ds}N_{ds}N_{ds}N_{ds}N_{ds}N_{ds}N_{ds}N_{ds}N_{es}N_{es}N_{es}N_{es}N_{e}$ | 6.25 | 0.50 | 19 | 10 |
| C5 | $N_{es}N_{es}N_{es}N_{es}N_{es}N_{ds}N_{ds}N_{ds}N_{ds}N_{ds}N_{ds}N_{ds}N_{ds}N_{ds}N_{ds}N_{es}N_{es}N_{es}N_{es}N_{e}$ | 6.00 | 0.00 | 15 | 10 |
| C13 | $N_{es}N_{es}N_{es}N_{es}N_{es}N_{ds}N_{ds}N_{ds}N_{ds}N_{ds}N_{ds}N_{ds}N_{ds}N_{ds}N_{ds}N_{es}N_{es}N_{es}N_{es}N_{e}$ | 6.00 | 0.00 | 20 | 10 |
| C14 | $N_{es}N_{es}N_{es}N_{es}N_{es}N_{ds}N_{ds}N_{ds}N_{ds}N_{ds}N_{ds}N_{ds}N_{ds}N_{ds}N_{ds}N_{es}N_{es}N_{es}N_{es}N_{e}$ | 4.75 | 0.50 | 21 | 10 |
| C7 | $N_{es}N_{es}N_{es}N_{es}N_{es}N_{ds}N_{ds}N_{ds}N_{ds}N_{ds}N_{ds}N_{ds}N_{ds}N_{ds}N_{ds}N_{es}N_{es}N_{es}N_{es}N_{e}$ | 5.25 | 0.50 | 16 | 10 |
| C15 | $N_{es}N_{es}N_{es}N_{es}N_{es}N_{ds}N_{ds}N_{ds}N_{ds}N_{ds}N_{ds}N_{ds}N_{ds}N_{ds}N_{ds}N_{es}N_{es}N_{es}N_{es}N_{e}$ | 0.00 | 0.00 | 22 | 10 |
| C9 | $N_{es}N_{es}N_{es}N_{es}N_{es}N_{ds}N_{ds}N_{ds}N_{ds}N_{ds}N_{ds}N_{ds}N_{ds}N_{ds}N_{ds}N_{es}N_{es}N_{es}N_{es}N_{e}$ | 5.00 | 1.15 | 17 | 10 |
| C3 | $N_{es}N_{es}N_{es}N_{es}N_{es}N_{ds}N_{ds}N_{ds}N_{ds}N_{ds}N_{ds}N_{ds}N_{ds}N_{ds}N_{ds}N_{es}N_{es}N_{es}N_{es}N_{e}$ | 2.25 | 0.50 | 14 | 10 |
| C1 | $N_{es}N_{es}N_{es}N_{es}N_{es}N_{ds}N_{ds}N_{ds}N_{ds}N_{ds}N_{ds}N_{ds}N_{ds}N_{ds}N_{ds}N_{es}N_{es}N_{es}N_{es}N_{e}$ | 0.50 | 0.58 | 13 | 10 |
| C16 | $N_{es}N_{es}N_{es}N_{es}N_{es}N_{ds}N_{ds}N_{ds}N_{ds}N_{ds}N_{ds}N_{ds}N_{ds}N_{ds}N_{ds}N_{es}N_{es}N_{es}N_{es}N_{e}$ | 3.75 | 2.87 | 23 | 10 |
| C17 | $N_{es}N_{es}N_{es}N_{es}N_{es}N_{ds}N_{ds}N_{ds}N_{ds}N_{ds}N_{ds}N_{ds}N_{ds}N_{ds}N_{ds}N_{es}N_{es}N_{es}N_{es}N_{e}$ | 4.50 | 3.00 | 24 | 10 |

TABLE 19

300 µg ICV Bolus Study With Oligonucleotides Containing 8 Nucleotide Gaps

| ISIS NO. | Sequence (5' to 3') | Score at 3 hours post injection | Std Dev | Sequence Identifier | SEQ ID NO |
|---|---|---|---|---|---|
| PBS | | 0.00 | 0.00 | | |
| C18 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 1.25 | 0.50 | 25 | 11 |
| C19 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 1.50 | 0.58 | 26 | 11 |
| C20 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 0.25 | 0.50 | 27 | 11 |
| C21 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 3.75 | 0.96 | 28 | 11 |
| C22 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 0.00 | 0.00 | 29 | 11 |
| C23 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 0.00 | 0.00 | 30 | 11 |
| C24 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 2.25 | 0.50 | 31 | 11 |
| C25 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 0.00 | 0.00 | 32 | 11 |
| C26 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 0.00 | 0.00 | 33 | 11 |
| C27 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 0.00 | 0.00 | 34 | 11 |
| C28 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 3.75 | 0.50 | 35 | 11 |
| C29 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 0.00 | 0.00 | 36 | 11 |
| C30 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 0.25 | 0.50 | 37 | 11 |
| C31 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 3.75 | 1.26 | 38 | 11 |
| C32 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 4.75 | 0.50 | 39 | 11 |
| C33 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 0.00 | 0.00 | 40 | 11 |
| C34 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 0.00 | 0.00 | 41 | 11 |
| C35 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 2.75 | 2.22 | 42 | 11 |
| C36 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 4.25 | 2.22 | 43 | 11 |
| C37 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 0.00 | 0.00 | 44 | 11 |
| C38 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 0.00 | 0.00 | 45 | 11 |
| C39 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 3.25 | 1.50 | 46 | 11 |
| C40 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 0.00 | 0.00 | 47 | 11 |
| C41 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 4.00 | 2.83 | 48 | 11 |
| C42 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 0.00 | 0.00 | 49 | 11 |
| C43 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 0.00 | 0.00 | 50 | 11 |
| C44 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 0.00 | 0.00 | 51 | 11 |
| C45 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 0.00 | 0.00 | 52 | 11 |
| C46 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 0.00 | 0.00 | 53 | 11 |
| C47 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 3.75 | 0.50 | 54 | 11 |
| C48 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 0.00 | 0.00 | 55 | 11 |
| C49 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 2.25 | 1.89 | 56 | 11 |
| C50 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 6.50 | 0.58 | 57 | 11 |
| C51 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 3.50 | 1.00 | 58 | 11 |
| C52 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 1.00 | 1.41 | 59 | 11 |
| C53 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 0.75 | 0.50 | 60 | 11 |

TABLE 19-continued

300 µg ICV Bolus Study With Oligonucleotides Containing 8 Nucleotide Gaps

| ISIS NO. | Sequence (5' to 3') | Score at 3 hours post injection | Std Dev | Sequence Identifier | SEQ ID NO |
|---|---|---|---|---|---|
| C54 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 1.00 | 1.41 | 61 | 11 |
| C55 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 1.25 | 1.89 | 62 | 11 |
| C56 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 5.50 | 1.29 | 63 | 11 |
| C57 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 0.00 | 0.00 | 64 | 11 |
| C58 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 0.25 | 0.50 | 65 | 11 |
| C59 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 3.75 | 1.50 | 66 | 11 |
| C60 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 0.00 | 0.00 | 67 | 11 |
| C61 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 3.25 | 2.06 | 68 | 11 |
| C62 | $N_{es}N_{eo}N_{ko}N_{ks}N_{ds}N_{ds}N_{ds}N_{ds}N_{ds}N_{ds}N_{ds}N_{ds}N_{ko}N_{ko}N_{es}N_{es}N_{e}$ | 0.50 | 1.00 | 69 | 11 |

The average score for the oligonucleotides having full PS internucleoside linkages and with 10 2'-deoxynucleotide gaps in Table 18 is 4.13, and the median score is 4.88. The average score for the oligonucleotides having mixed PO/PS internucleoside linkages and with 8 nucleotide 2'-deoxygaps in Table 19 is 1.53, and the median score is 0.50. Additionally, the average score for the PO/PS oligonucleotides with 10 nucleotide gaps in Table 17 (Isis No.'s C2, C4, C6, C8, and C10) is 2.05, and the median score is 3.00. Thus, these examples show that in certain embodiments, oligonucleotides having mixed PO/PS internucleoside linkages and short gaps had less acute toxicity than oligonucleotides directed to the same target and having full PS internucleoside linkages and longer 2'-deoxynucleoside gaps.

What is claimed is:

1. An oligomeric compound comprising a modified oligonucleotide consisting of 15 linked nucleosides, wherein the modified oligonucleotide has a sugar motif comprising:
a 5'-region consisting of 2 linked 5'-region nucleosides, wherein each 5'-region nucleoside is a modified nucleoside;
a 3'-region consisting of 4 linked 3'-region nucleosides, wherein the 3'-region has a BBBA motif, wherein A is a modified nucleoside of a first type and each B is a modified nucleoside of a second type; and
a central region between the 5'-region and the 3'-region consisting of 9 linked central region nucleosides, wherein each central region nucleoside is an unmodified 2'-deoxynucleoside, and
wherein the oligomeric compound comprises one or more phosphorothioate internucleoside linkages; wherein the 3'-most internucleoside linkage is a phosphorothioate internucleoside linkage, and both the $2^{nd}$ and $3^{rd}$ internucleoside linkages from the 3'-end of the modified oligonucleotide are phosphodiester internucleoside linkages.

2. The oligomeric compound of claim 1, wherein each 5'-region nucleoside is an RNA-like nucleoside.

3. The oligomeric compound of claim 1, wherein at least one modified 5'-region nucleoside comprises a modified sugar moiety.

4. The oligomeric compound of claim 1, wherein at least one modified 5'-region nucleoside comprises a bicyclic sugar moiety.

5. The oligomeric compound of claim 1, wherein at least one modified 5'-region nucleoside comprises a 2'-substituted sugar moiety comprising a 2' substituent selected from halogen, optionally substituted allyl, optionally substituted amino, azido, optionally substituted SH, CN, OCN, $CF_3$, $OCF_3$, O, S, or $N(R_m)$-alkyl; O, S, or $N(R_m)$-alkenyl; O, S or $N(R_m)$-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, and $O(CH_2)_2$ $SCH_3$, O—$(CH_2)_2$—O—$N(R_m)(R_n)$ or O—$CH_2$—C (=O)—$N(R_m)(R_n)$, wherein each $R_m$ and $R_n$ is, independently, H, an amino protecting group or substituted or unsubstituted $C_1$-$C_{10}$ alkyl; wherein each optionally substituted group is optionally substituted with a substituent group independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

6. The oligomeric compound of claim 4, wherein at least one modified 5'-region nucleoside comprises a 2'-substituted sugar moiety comprising a 2' substituent selected from halogen, optionally substituted allyl, optionally substituted amino, azido, optionally substituted SH, CN, OCN, $CF_3$, $OCF_3$, O, S, or $N(R_m)$-alkyl; O, S, or $N(R_m)$-alkenyl; O, S or $N(R_m)$-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, and $O(CH_2)_2$ $SCH_3$, O—$(CH_2)_2$—O—$N(R_m)(R_n)$ or O—$CH_2$—C (=O)—$N(R_m)(R_n)$, wherein each $R_m$ and $R_n$ is, independently, H, an amino protecting group or substituted or unsubstituted $C_1$-$C_{10}$ alkyl; wherein each optionally substituted group is optionally substituted with a substituent group independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

7. The oligomeric compound of claim 1, wherein the 5'-most internucleoside linkage is a phosphorothioate internucleoside linkage.

8. The oligomeric compound of claim 1, wherein the 3'-most internucleoside linkage of the central region of the sugar motif is a phosphorothioate internucleoside linkage.

9. The oligomeric compound of claim 4, wherein the bicyclic sugar moiety has a 2'-4' bridge, wherein the 2'-4' bridge is selected from —O—$CH_2$—; and —O—CH ($CH_3$)—.

10. The oligomeric compound of claim 4, wherein exactly one 5'-region nucleoside comprises a bicyclic sugar moiety and the other 5'-region nucleoside comprises a 2'-substituted sugar moiety, wherein the 2'-substitutent group is selected from F, $OCH_3$, and $OCH_2CH_2OCH_3$.

11. The oligomeric compound of claim 1, wherein each "B" is a nucleoside comprising a bicyclic sugar moiety, and each "A" is a nucleoside comprising a 2'-substituted sugar moiety.

12. The oligomeric compound of claim 11, wherein each bicyclic sugar moiety has a 2'-4' bridge, wherein the 2'-4' bridge is selected from —O—$CH_2$—; and —O—CH ($CH_3$)—.

13. The oligomeric compound of claim 11, wherein each 2'-substituted sugar moiety has a 2'-substitutent group selected from F, OCH$_3$, and OCH$_2$CH$_2$OCH$_3$.

14. The oligomeric compound of claim 1, wherein each nucleobase is selected from adenine, thymine, guanosine, cytosine, and 5-methyl cytosine.

15. The oligomeric compound of claim 1, wherein each remaining internucleoside linkage is a phosphorothioate internucleoside linkage.

* * * * *